US010167447B2

(12) United States Patent
Yao et al.

(10) Patent No.: US 10,167,447 B2
(45) Date of Patent: Jan. 1, 2019

(54) SUPPORTS AND METHODS FOR PROMOTING INTEGRATION OF CARTILAGE TISSUE EXPLANTS

(71) Applicant: Zimmer, Inc., Warsaw, IN (US)

(72) Inventors: Jian Q. Yao, Shanghai (CN); Hali Wang, The Hills, TX (US)

(73) Assignee: Zimmer, Inc., Warsaw, IN (US)

( * ) Notice: Subject to any disclaimer, the term of this patent is extended or adjusted under 35 U.S.C. 154(b) by 79 days.

(21) Appl. No.: 14/299,314

(22) Filed: Jun. 9, 2014

(65) Prior Publication Data

US 2014/0335612 A1    Nov. 13, 2014

Related U.S. Application Data

(62) Division of application No. 13/799,452, filed on Mar. 13, 2013, now abandoned.

(60) Provisional application No. 61/740,787, filed on Dec. 21, 2012.

(51) Int. Cl.
*C12N 5/077* (2010.01)
*A61L 27/38* (2006.01)
*A61L 27/36* (2006.01)
*A61L 27/54* (2006.01)

(52) U.S. Cl.
CPC ........ *C12N 5/0655* (2013.01); *A61L 27/3612* (2013.01); *A61L 27/3852* (2013.01); *A61L 27/54* (2013.01); *A61L 2300/414* (2013.01); *A61L 2300/426* (2013.01); *A61L 2300/43* (2013.01); *A61L 2430/06* (2013.01); *C12N 2500/90* (2013.01); *C12N 2501/10* (2013.01); *C12N 2501/20* (2013.01); *C12N 2501/30* (2013.01)

(58) Field of Classification Search
None
See application file for complete search history.

(56) References Cited

U.S. PATENT DOCUMENTS

| | | |
|---|---|---|
| 1,347,622 A | 7/1920 | Deininger |
| 2,533,004 A | 12/1950 | Ferry et al. |
| 2,621,145 A | 12/1952 | Sano |
| 3,302,289 A | 2/1967 | Spaulding |
| 3,400,199 A | 9/1968 | Balassa |
| 3,474,146 A | 10/1969 | Baker et al. |
| 3,476,855 A | 11/1969 | Balassa |
| 3,478,146 A | 11/1969 | Balassa |
| 3,772,432 A | 11/1973 | Balassal |
| RE28,093 E | 7/1974 | Balassa et al. |
| 3,966,908 A | 6/1976 | Balassa |
| 4,440,680 A | 4/1984 | Cioca |
| 4,453,939 A | 6/1984 | Zimmerman et al. |
| 4,479,271 A | 10/1984 | Bolesky et al. |
| 4,522,096 A | 6/1985 | Niven, Jr. |
| 4,566,138 A | 1/1986 | Lewis et al. |
| 4,587,766 A | 5/1986 | Miyatake et al. |
| 4,609,551 A | 9/1986 | Caplan et al. |
| 4,627,879 A | 12/1986 | Rose et al. |
| 4,640,834 A | 2/1987 | Eibl et al. |
| 4,641,651 A | 2/1987 | Card |
| 4,642,120 A | 2/1987 | Nevo et al. |
| 4,656,137 A | 4/1987 | Balassa |
| 4,660,755 A | 4/1987 | Farling |
| 4,714,457 A | 12/1987 | Alterbaum |
| 4,773,418 A | 9/1988 | Hettich |
| 4,818,633 A | 4/1989 | Dinwoodie et al. |
| 4,846,835 A | 7/1989 | Grande |
| 4,851,354 A | 7/1989 | Winston et al. |
| 4,863,474 A | 9/1989 | Brown et al. |
| 4,863,475 A | 9/1989 | Andersen et al. |
| 4,904,259 A | 2/1990 | Itay |
| 4,911,720 A | 3/1990 | Collier |
| 4,928,603 A | 5/1990 | Rose et al. |
| 4,952,403 A | 8/1990 | Vallee et al. |
| 4,963,489 A | 10/1990 | Naughton et al. |
| 4,997,444 A | 3/1991 | Farling |
| 4,997,445 A | 3/1991 | Hodorek |
| 5,002,071 A | 3/1991 | Harrell |
| 5,002,582 A | 3/1991 | Guire et al. |
| 5,013,324 A | 5/1991 | Zolman et al. |
| 5,018,285 A | 5/1991 | Zolman et al. |
| 5,030,215 A | 7/1991 | Morse et al. |
| 5,032,508 A | 7/1991 | Naughton et al. |
| 5,041,138 A | 8/1991 | Vacanti et al. |
| 5,053,050 A | 10/1991 | Itay |
| 5,067,963 A | 11/1991 | Khouri et al. |
| 5,067,964 A | 11/1991 | Richmond et al. |
| 5,069,881 A | 12/1991 | Clarkin |
| 5,080,674 A | 1/1992 | Jacobs et al. |
| 5,092,887 A | 3/1992 | Gendler |
| 5,130,418 A | 7/1992 | Thompson |
| 5,139,527 A | 8/1992 | Redl et al. |
| 5,189,148 A | 2/1993 | Akiyama et al. |
| 5,198,308 A | 3/1993 | Shetty et al. |
| 5,206,023 A | 4/1993 | Hunziker |

(Continued)

FOREIGN PATENT DOCUMENTS

| | | |
|---|---|---|
| AU | 199871003 B2 | 10/1998 |
| AU | 2006282754 A2 | 3/2007 |

(Continued)

OTHER PUBLICATIONS

US 8,382,851, 02/2013, Gage et al. (withdrawn)

(Continued)

*Primary Examiner* — Thomas J. Visone
*Assistant Examiner* — Evelyn Y Pyla
(74) *Attorney, Agent, or Firm* — Schwegman Lundberg & Woessner, P.A.

(57) ABSTRACT

The present disclosure provides tissue supports and methods for preparing a cartilage composition for repairing cartilage defects, which is prepared by expanding and integrating small cartilage tissue pieces derived from donor or engineered tissue. The methods and supports described herein promote cell migration and integration of neighboring tissue pieces in culture to form the cartilage composition. Methods of cartilage repair using the cartilage composition are also described.

5 Claims, 18 Drawing Sheets

(56) References Cited

U.S. PATENT DOCUMENTS

| | | |
|---|---|---|
| 5,217,954 A | 6/1993 | Foster et al. |
| 5,219,363 A | 6/1993 | Crowninshield et al. |
| 5,226,914 A | 7/1993 | Caplan et al. |
| 5,236,457 A | 8/1993 | Devanathan |
| 5,254,471 A | 10/1993 | Mori et al. |
| 5,269,785 A | 12/1993 | Bonutti |
| 5,270,300 A | 12/1993 | Hunziker |
| 5,281,422 A | 1/1994 | Badylak et al. |
| 5,282,861 A | 2/1994 | Kaplan |
| 5,290,552 A | 3/1994 | Sierra et al. |
| 5,290,558 A | 3/1994 | O'Leary et al. |
| 5,312,417 A | 5/1994 | Wilk |
| 5,323,954 A | 6/1994 | Shetty et al. |
| 5,326,357 A | 7/1994 | Kandel |
| 5,345,927 A | 9/1994 | Bonutti |
| 5,356,629 A | 10/1994 | Sander et al. |
| 5,368,858 A | 11/1994 | Hunziker |
| 5,372,821 A | 12/1994 | Badylak et al. |
| 5,387,243 A | 2/1995 | Devanathan |
| 5,403,317 A | 4/1995 | Bonutti |
| 5,405,607 A | 4/1995 | Epstein |
| 5,410,016 A | 4/1995 | Hubbell et al. |
| 5,443,454 A | 8/1995 | Tanabe et al. |
| 5,443,510 A | 8/1995 | Shetty |
| 5,443,512 A | 8/1995 | Parr et al. |
| 5,445,833 A | 8/1995 | Badylak et al. |
| 5,456,723 A | 10/1995 | Steinemann |
| 5,456,828 A | 10/1995 | Tersi et al. |
| 5,461,953 A | 10/1995 | Mccormick |
| 5,475,052 A | 12/1995 | Rhee et al. |
| 5,482,929 A | 1/1996 | Fukunaga et al. |
| 5,496,375 A | 3/1996 | Sisk et al. |
| 5,504,300 A | 4/1996 | Devanathan et al. |
| 5,510,396 A | 4/1996 | Prewett et al. |
| 5,514,536 A | 5/1996 | Taylor |
| 5,516,532 A | 5/1996 | Atala et al. |
| 5,516,533 A | 5/1996 | Badylak et al. |
| 5,535,810 A | 7/1996 | Compton et al. |
| 5,545,222 A | 8/1996 | Bonutti |
| 5,549,704 A | 8/1996 | Sutter |
| 5,549,904 A | 8/1996 | Juergensen et al. |
| 5,554,389 A | 9/1996 | Badylak et al. |
| 5,556,429 A | 9/1996 | Felt |
| 5,565,519 A | 10/1996 | Rhee et al. |
| 5,571,187 A | 11/1996 | Devanathan |
| 5,577,517 A | 11/1996 | Bonutti |
| 5,578,492 A | 11/1996 | Fedun |
| 5,585,007 A | 12/1996 | Antanavich et al. |
| 5,605,887 A | 2/1997 | Pines et al. |
| 5,612,028 A | 3/1997 | Sackier et al. |
| 5,618,925 A | 4/1997 | Dupont et al. |
| 5,624,463 A | 4/1997 | Stone et al. |
| 5,639,280 A | 6/1997 | Warner et al. |
| 5,643,192 A | 7/1997 | Hirsh |
| 5,650,494 A | 7/1997 | Cerletti et al. |
| 5,654,166 A | 8/1997 | Kurth |
| 5,655,546 A | 8/1997 | Halpern |
| 5,656,587 A | 8/1997 | Sporn et al. |
| 5,662,710 A | 9/1997 | Bonutti |
| 5,669,544 A | 9/1997 | Schulze et al. |
| 5,672,284 A | 9/1997 | Devanathan et al. |
| 5,673,840 A | 10/1997 | Schulze et al. |
| 5,673,841 A | 10/1997 | Schulze et al. |
| 5,680,982 A | 10/1997 | Schulze et al. |
| 5,681,353 A | 10/1997 | Li et al. |
| 5,692,668 A | 12/1997 | Schulze et al. |
| 5,694,951 A | 12/1997 | Bonutti |
| 5,695,998 A | 12/1997 | Badylak et al. |
| 5,709,854 A | 1/1998 | Griffith-Cima et al. |
| 5,713,374 A | 2/1998 | Pachence et al. |
| 5,714,371 A | 2/1998 | Ramanathan et al. |
| 5,723,010 A | 3/1998 | Yui et al. |
| 5,723,011 A | 3/1998 | Devanathan et al. |
| 5,723,331 A | 3/1998 | Tubo et al. |
| 5,734,959 A | 3/1998 | Krebs et al. |
| 5,735,875 A | 4/1998 | Bonutti et al. |
| 5,736,132 A | 4/1998 | Juergensen et al. |
| 5,736,396 A | 4/1998 | Bruder et al. |
| 5,749,968 A | 5/1998 | Melanson et al. |
| 5,753,485 A | 5/1998 | Dwulet |
| 5,755,791 A | 5/1998 | Whitson et al. |
| 5,769,899 A | 6/1998 | Schwartz et al. |
| 5,770,194 A | 6/1998 | Edwardson et al. |
| 5,782,835 A | 7/1998 | Hart et al. |
| 5,782,915 A | 7/1998 | Stone |
| 5,786,217 A | 7/1998 | Tubo et al. |
| 5,788,662 A | 8/1998 | Antanavich et al. |
| 5,795,571 A | 8/1998 | Cederholm-Williams et al. |
| 5,795,780 A | 8/1998 | Cederholm-Williams et al. |
| 5,811,094 A | 9/1998 | Caplan et al. |
| 5,824,093 A | 10/1998 | Ray et al. |
| 5,826,776 A | 10/1998 | Schulze et al. |
| 5,827,217 A | 10/1998 | Silver et al. |
| 5,830,741 A | 11/1998 | Dwulet et al. |
| 5,842,477 A | 12/1998 | Naughton et al. |
| 5,853,746 A | 12/1998 | Hunziker |
| 5,853,976 A | 12/1998 | Hesse et al. |
| 5,864,016 A | 1/1999 | Eibl et al. |
| 5,866,415 A | 2/1999 | Villeneuve |
| 5,866,630 A | 2/1999 | Mitra et al. |
| 5,876,208 A | 3/1999 | Mitra et al. |
| 5,876,451 A | 3/1999 | Yui et al. |
| 5,876,452 A | 3/1999 | Athanasiou et al. |
| 5,879,398 A | 3/1999 | Swarts et al. |
| 5,888,219 A | 3/1999 | Bonutti |
| 5,888,491 A | 3/1999 | Mitra et al. |
| 5,890,898 A | 4/1999 | Wada et al. |
| 5,891,455 A | 4/1999 | Sittinger et al. |
| 5,899,936 A | 5/1999 | Goldstein |
| 5,902,741 A | 5/1999 | Purchio et al. |
| 5,919,702 A | 7/1999 | Purchio et al. |
| 5,921,987 A | 7/1999 | Stone |
| 5,922,027 A | 7/1999 | Stone |
| 5,922,846 A | 7/1999 | Cerletti et al. |
| 5,926,685 A | 7/1999 | Krebs et al. |
| 5,928,945 A | 7/1999 | Seliktar et al. |
| 5,935,131 A | 8/1999 | Bonutti |
| 5,944,754 A | 8/1999 | Vacanti |
| 5,944,755 A | 8/1999 | Stone |
| 5,948,384 A | 9/1999 | Filler |
| 5,952,215 A | 9/1999 | Dwulet et al. |
| 5,962,405 A | 10/1999 | Seelich |
| 5,964,752 A | 10/1999 | Stone |
| 5,964,805 A | 10/1999 | Stone |
| 5,968,556 A | 10/1999 | Atala et al. |
| 5,985,315 A | 11/1999 | Patat et al. |
| 5,989,269 A | 11/1999 | Vibe-hansen et al. |
| 5,989,888 A | 11/1999 | Dwulet et al. |
| 6,022,361 A | 2/2000 | Epstein et al. |
| 6,025,334 A | 2/2000 | Dupont et al. |
| 6,045,990 A | 4/2000 | Baust et al. |
| 6,048,966 A | 4/2000 | Edwardson et al. |
| 6,051,249 A | 4/2000 | Samuelsen |
| 6,060,053 A | 5/2000 | Atala |
| 6,077,989 A | 6/2000 | Kandel et al. |
| 6,080,194 A | 6/2000 | Pachence et al. |
| 6,080,579 A | 6/2000 | Hanley et al. |
| 6,083,383 A | 7/2000 | Huang et al. |
| 6,087,553 A | 7/2000 | Cohen et al. |
| 6,107,085 A | 8/2000 | Coughlin et al. |
| 6,110,209 A | 8/2000 | Stone |
| 6,110,210 A | 8/2000 | Norton et al. |
| 6,110,212 A | 8/2000 | Gregory |
| 6,110,482 A | 8/2000 | Khouri et al. |
| 6,120,514 A | 9/2000 | Vibe-hansen et al. |
| 6,129,761 A | 10/2000 | Hubbell |
| 6,132,465 A | 10/2000 | Ray et al. |
| 6,132,472 A | 10/2000 | Bonutti |
| 6,140,123 A | 10/2000 | Demetriou et al. |
| 6,140,452 A | 10/2000 | Felt et al. |
| 6,143,214 A | 11/2000 | Barlow |
| 6,150,163 A | 11/2000 | McPherson et al. |
| 6,152,142 A | 11/2000 | Tseng |
| 6,162,241 A | 12/2000 | Coury et al. |

(56) References Cited

U.S. PATENT DOCUMENTS

| | | |
|---|---|---|
| 6,171,610 B1 | 1/2001 | Vacanti et al. |
| 6,174,313 B1 | 1/2001 | Bonutti |
| 6,179,871 B1 | 1/2001 | Halpern |
| 6,183,737 B1 | 2/2001 | Zaleske et al. |
| 6,187,329 B1 | 2/2001 | Agrawal et al. |
| 6,197,575 B1 | 3/2001 | Griffith et al. |
| 6,200,330 B1 | 3/2001 | Benderev et al. |
| 6,203,526 B1 | 3/2001 | McBeth et al. |
| 6,224,893 B1 | 5/2001 | Langer et al. |
| 6,235,316 B1 | 5/2001 | Adkisson |
| 6,242,247 B1 | 6/2001 | Reiser et al. |
| 6,248,114 B1 | 6/2001 | Ysebaert |
| 6,264,659 B1 | 7/2001 | Ross et al. |
| 6,271,320 B1 | 8/2001 | Keller et al. |
| 6,274,090 B1 | 8/2001 | Coelho et al. |
| 6,280,993 B1 | 8/2001 | Yamato et al. |
| 6,294,656 B1 | 9/2001 | Mittl et al. |
| 6,306,169 B1 | 10/2001 | Lee et al. |
| 6,306,177 B1 | 10/2001 | Felt et al. |
| 6,312,668 B2 | 11/2001 | Mitra et al. |
| 6,322,563 B1 | 11/2001 | Cummings et al. |
| 6,327,257 B1 | 12/2001 | Khalifa |
| 6,336,930 B1 | 1/2002 | Stalcup et al. |
| 6,338,878 B1 | 1/2002 | Overton et al. |
| 6,358,266 B1 | 3/2002 | Bonutti |
| 6,361,565 B1 | 3/2002 | Bonutti |
| 6,368,298 B1 | 4/2002 | Beretta et al. |
| 6,368,784 B1 | 4/2002 | Murray |
| 6,370,920 B1 | 4/2002 | Overton et al. |
| 6,378,527 B1 | 4/2002 | Hungerford et al. |
| 6,395,327 B1 | 5/2002 | Shetty |
| 6,417,320 B1 | 7/2002 | Otto et al. |
| 6,423,063 B1 | 7/2002 | Bonutti |
| 6,425,704 B2 | 7/2002 | Voiers et al. |
| 6,436,143 B1 | 8/2002 | Ross et al. |
| 6,437,018 B1 | 8/2002 | Gertzman et al. |
| 6,443,988 B2 | 9/2002 | Felt et al. |
| 6,444,228 B1 | 9/2002 | Baugh et al. |
| 6,447,514 B1 | 9/2002 | Stalpcup et al. |
| 6,464,713 B2 | 10/2002 | Bonutti |
| 6,468,289 B1 | 10/2002 | Bonutti |
| 6,468,527 B2 | 10/2002 | Austin et al. |
| 6,472,162 B1 | 10/2002 | Coelho et al. |
| 6,475,764 B1 | 11/2002 | Burtscher et al. |
| 6,482,235 B1 | 11/2002 | Lambrecht et al. |
| 6,485,723 B1 | 11/2002 | Badylak et al. |
| 6,492,163 B1 | 12/2002 | Yoo et al. |
| 6,497,903 B1 | 12/2002 | Hennink et al. |
| 6,503,267 B2 | 1/2003 | Bonutti et al. |
| 6,503,277 B2 | 1/2003 | Bonutti |
| 6,504,079 B2 | 1/2003 | Tucker et al. |
| 6,511,958 B1 | 1/2003 | Atkinson et al. |
| 6,514,514 B1 | 2/2003 | Atkinson et al. |
| 6,514,522 B2 | 2/2003 | Domb |
| 6,528,052 B1 | 3/2003 | Smith et al. |
| 6,530,956 B1 * | 3/2003 | Mansmann ......... A61F 2/30756 623/18.11 |
| 6,533,817 B1 | 3/2003 | Norton et al. |
| 6,534,084 B1 | 3/2003 | Vyakarnam et al. |
| 6,534,591 B2 | 3/2003 | Rhee et al. |
| 6,543,455 B2 | 4/2003 | Bonutti |
| 6,544,472 B1 | 4/2003 | Compton et al. |
| 6,551,355 B1 | 4/2003 | Lewandrowski et al. |
| 6,559,119 B1 | 5/2003 | Burgess et al. |
| 6,575,982 B1 | 6/2003 | Bonutti |
| 6,576,265 B1 | 6/2003 | Spievack |
| 6,579,538 B1 | 6/2003 | Spievack |
| 6,582,960 B1 | 6/2003 | Martin et al. |
| 6,592,531 B2 | 7/2003 | Bonutti et al. |
| 6,596,180 B2 | 7/2003 | Baugh et al. |
| 6,599,515 B1 | 7/2003 | Delmotte |
| 6,607,534 B2 | 8/2003 | Bonutti |
| 6,610,033 B1 | 8/2003 | Melanson et al. |
| 6,620,169 B1 | 9/2003 | Peterson et al. |
| 6,626,859 B2 | 9/2003 | Von Segesser |
| 6,626,945 B2 | 9/2003 | Simon et al. |
| 6,626,950 B2 | 9/2003 | Brown et al. |
| 6,630,000 B1 | 10/2003 | Bonutti |
| 6,632,246 B1 | 10/2003 | Simon et al. |
| 6,632,648 B1 | 10/2003 | Kampinga et al. |
| 6,637,437 B1 | 10/2003 | Hungerford et al. |
| 6,638,309 B2 | 10/2003 | Bonutti |
| 6,645,316 B1 | 11/2003 | Brouwer et al. |
| 6,645,764 B1 | 11/2003 | Adkisson |
| 6,649,168 B2 | 11/2003 | Arvinte et al. |
| 6,652,532 B2 | 11/2003 | Bonutti |
| 6,652,872 B2 | 11/2003 | Nevo et al. |
| 6,652,883 B2 | 11/2003 | Goupil et al. |
| 6,653,062 B1 | 11/2003 | DePablo et al. |
| 6,662,805 B2 | 12/2003 | Frondoza et al. |
| 6,663,616 B1 | 12/2003 | Roth et al. |
| 6,676,971 B2 | 1/2004 | Goupil et al. |
| 6,685,987 B2 | 2/2004 | Shetty |
| 6,697,143 B2 | 2/2004 | Freeman |
| 6,705,790 B2 | 3/2004 | Quintero et al. |
| 6,713,772 B2 | 3/2004 | Goodman et al. |
| 6,719,803 B2 | 4/2004 | Bonutti |
| 6,719,901 B2 | 4/2004 | Dolecek et al. |
| 6,730,299 B1 | 5/2004 | Tayot et al. |
| 6,733,515 B1 | 5/2004 | Edwards et al. |
| 6,736,853 B2 | 5/2004 | Bonutti |
| 6,737,072 B1 | 5/2004 | Angele |
| 6,740,186 B2 | 5/2004 | Hawkins et al. |
| 6,743,232 B2 | 6/2004 | Overaker et al. |
| 6,773,458 B1 | 8/2004 | Brauker et al. |
| 6,773,713 B2 | 8/2004 | Bonassar et al. |
| 6,776,938 B2 | 8/2004 | Bonnutti |
| 6,797,006 B2 | 9/2004 | Hodorek |
| 6,800,663 B2 | 10/2004 | Asgarzadeh et al. |
| 6,818,008 B1 | 11/2004 | Cates et al. |
| 6,830,762 B2 | 12/2004 | Baugh et al. |
| 6,833,408 B2 | 12/2004 | Sehl et al. |
| 6,835,198 B2 | 12/2004 | Bonutti |
| 6,835,277 B2 | 12/2004 | Park |
| 6,840,960 B2 | 1/2005 | Bubb |
| 6,852,330 B2 | 2/2005 | Bowman et al. |
| 6,860,904 B2 | 3/2005 | Bonutti |
| 6,884,428 B2 | 4/2005 | Binette et al. |
| 6,886,568 B2 | 5/2005 | Frondoza et al. |
| 6,893,466 B2 | 5/2005 | Trieu |
| 6,905,517 B2 | 6/2005 | Bonutti et al. |
| 6,919,067 B2 | 7/2005 | Filler et al. |
| 6,919,172 B2 | 7/2005 | DePablo et al. |
| 6,921,633 B2 | 7/2005 | Baust et al. |
| 6,942,880 B1 | 9/2005 | Dolecek et al. |
| 6,949,252 B2 | 9/2005 | Mizuno et al. |
| 6,965,014 B1 | 11/2005 | Delmotte et al. |
| 6,979,307 B2 | 12/2005 | Beretta et al. |
| 6,990,982 B1 | 1/2006 | Bonutti |
| 6,991,652 B2 | 1/2006 | Burg |
| 7,009,039 B2 | 3/2006 | Yayon et al. |
| 7,045,601 B2 | 5/2006 | Metzner et al. |
| 7,067,123 B2 | 6/2006 | Gomes et al. |
| 7,081,125 B2 | 7/2006 | Edwards et al. |
| 7,083,964 B2 | 8/2006 | Kurfurst |
| 7,087,227 B2 | 8/2006 | Adkisson |
| RE39,321 E | 10/2006 | MacPhee et al. |
| 7,134,437 B2 | 11/2006 | Bonutti |
| 7,147,471 B2 | 12/2006 | Frey et al. |
| 7,160,725 B2 * | 1/2007 | Warzecha ..................... 435/377 |
| 7,217,294 B2 | 5/2007 | Kusanagi et al. |
| 7,235,255 B2 | 6/2007 | Austin et al. |
| 7,273,756 B2 | 9/2007 | Adkisson et al. |
| 7,276,235 B2 | 10/2007 | Metzner et al. |
| 7,276,481 B2 | 10/2007 | Golembo et al. |
| 7,299,805 B2 | 11/2007 | Bonutti |
| 7,316,822 B2 | 1/2008 | Binette et al. |
| 7,375,077 B2 | 5/2008 | Mao |
| 7,468,192 B2 | 12/2008 | Mizuno et al. |
| 7,488,348 B2 | 2/2009 | Truncale et al. |
| 7,537,780 B2 | 5/2009 | Mizuno et al. |
| 7,720,533 B2 | 5/2010 | Behravesh |
| 7,824,711 B2 | 11/2010 | Kizer et al. |
| 7,838,040 B2 | 11/2010 | Malinin |

(56) References Cited

U.S. PATENT DOCUMENTS

| | | |
|---|---|---|
| 7,875,296 B2 | 1/2011 | Binette et al. |
| 7,879,604 B2 | 2/2011 | Seyedin et al. |
| RE42,208 E | 3/2011 | Truncale et al. |
| 7,897,384 B2 | 3/2011 | Binette et al. |
| 7,901,457 B2 | 3/2011 | Truncale et al. |
| 7,901,461 B2 | 3/2011 | Harmon et al. |
| 8,017,394 B2 | 9/2011 | Adkisson, IV et al. |
| 8,025,901 B2 | 9/2011 | Kao et al. |
| 8,137,702 B2 | 3/2012 | Binette et al. |
| 8,163,549 B2 | 4/2012 | Yao et al. |
| 8,480,757 B2 | 7/2013 | Gage et al. |
| 8,497,121 B2 | 7/2013 | Yao et al. |
| 8,518,433 B2 | 8/2013 | Kizer et al. |
| 8,524,268 B2 | 9/2013 | Kizer et al. |
| 8,652,507 B2 | 2/2014 | Kizer et al. |
| 8,765,165 B2 | 7/2014 | Kizer et al. |
| 8,784,863 B2 | 7/2014 | Kizer et al. |
| 8,834,914 B2 | 9/2014 | Kizer et al. |
| 9,138,318 B2 | 9/2015 | Yao et al. |
| 2001/0004710 A1 | 6/2001 | Felt et al. |
| 2001/0006634 A1 | 7/2001 | Zaleske et al. |
| 2001/0014473 A1 | 8/2001 | Rieser et al. |
| 2001/0014475 A1 | 8/2001 | Frondoza et al. |
| 2001/0051834 A1 | 12/2001 | Frondoza et al. |
| 2001/0055621 A1 | 12/2001 | Baugh et al. |
| 2002/0004038 A1 | 1/2002 | Baugh et al. |
| 2002/0009805 A1 | 1/2002 | Nevo et al. |
| 2002/0012705 A1 | 1/2002 | Domb |
| 2002/0028192 A1 | 3/2002 | Dimitrijevich et al. |
| 2002/0029055 A1 | 3/2002 | Bonutti |
| 2002/0045940 A1 | 4/2002 | Giannetti et al. |
| 2002/0055755 A1 | 5/2002 | Bonutti |
| 2002/0062151 A1 | 5/2002 | Altman et al. |
| 2002/0064512 A1 | 5/2002 | Petersen et al. |
| 2002/0082623 A1 | 6/2002 | Osther et al. |
| 2002/0095160 A1 | 7/2002 | Bonutti |
| 2002/0099401 A1 | 7/2002 | Bonuttie |
| 2002/0099448 A1 | 7/2002 | Hiles et al. |
| 2002/0106625 A1 | 8/2002 | Hung et al. |
| 2002/0110544 A1* | 8/2002 | Goldberg ............ C12N 5/0655 424/93.7 |
| 2002/0123142 A1 | 9/2002 | Hungerford et al. |
| 2002/0128683 A1 | 9/2002 | Epstein |
| 2002/0133235 A1 | 9/2002 | Hungerford et al. |
| 2002/0150550 A1 | 10/2002 | Petersen |
| 2002/0151974 A1 | 10/2002 | Bonassar et al. |
| 2002/0159982 A1 | 10/2002 | Bonassar et al. |
| 2002/0159985 A1 | 10/2002 | Baugh et al. |
| 2002/0183850 A1 | 12/2002 | Felt et al. |
| 2002/0198490 A1 | 12/2002 | Wirt et al. |
| 2002/0198599 A1 | 12/2002 | Haldimann |
| 2003/0004578 A1 | 1/2003 | Brown et al. |
| 2003/0009147 A1 | 1/2003 | Bonutti |
| 2003/0009235 A1 | 1/2003 | Manrique et al. |
| 2003/0039695 A1 | 2/2003 | Geistlich et al. |
| 2003/0040113 A1 | 2/2003 | Mizuno et al. |
| 2003/0065389 A1 | 4/2003 | Petersen |
| 2003/0069605 A1 | 4/2003 | Bonutti et al. |
| 2003/0077244 A1 | 4/2003 | Petersen |
| 2003/0099620 A1 | 5/2003 | Zaleske et al. |
| 2003/0114936 A1 | 6/2003 | Sherwood et al. |
| 2003/0134032 A1 | 7/2003 | Chaouk et al. |
| 2003/0151974 A1 | 8/2003 | Kutty et al. |
| 2003/0153078 A1 | 8/2003 | Libera et al. |
| 2003/0176602 A1 | 9/2003 | Schmidt et al. |
| 2003/0181939 A1 | 9/2003 | Bonutti |
| 2003/0187387 A1 | 10/2003 | Wirt et al. |
| 2003/0195628 A1 | 10/2003 | Bao et al. |
| 2003/0199979 A1 | 10/2003 | Mcguckin, Jr. |
| 2003/0211073 A1 | 11/2003 | Goupil et al. |
| 2003/0220649 A1 | 11/2003 | Bao et al. |
| 2003/0223956 A1 | 12/2003 | Goupil et al. |
| 2004/0007890 A1 | 1/2004 | Blodgett, Jr. |
| 2004/0030404 A1 | 2/2004 | Noll et al. |
| 2004/0030406 A1 | 2/2004 | Ochi et al. |
| 2004/0033212 A1 | 2/2004 | Thomson et al. |
| 2004/0042960 A1 | 3/2004 | Frey et al. |
| 2004/0044408 A1 | 3/2004 | Hungerford et al. |
| 2004/0048796 A1 | 3/2004 | Hariri et al. |
| 2004/0059416 A1 | 3/2004 | Murray et al. |
| 2004/0064192 A1 | 4/2004 | Bubb |
| 2004/0064193 A1 | 4/2004 | Evans et al. |
| 2004/0073308 A1 | 4/2004 | Kuslich et al. |
| 2004/0078073 A1 | 4/2004 | Bonutti |
| 2004/0078077 A1 | 4/2004 | Bienette et al. |
| 2004/0078090 A1 | 4/2004 | Binette et al. |
| 2004/0092946 A1 | 5/2004 | Bagga et al. |
| 2004/0097714 A1 | 5/2004 | Maubois et al. |
| 2004/0097829 A1 | 5/2004 | McRury et al. |
| 2004/0117033 A1 | 6/2004 | Frondoza et al. |
| 2004/0127987 A1 | 7/2004 | Evans et al. |
| 2004/0134502 A1 | 7/2004 | Mizuno et al. |
| 2004/0138522 A1 | 7/2004 | Haarstad et al. |
| 2004/0151705 A1 | 8/2004 | Mizuno et al. |
| 2004/0172045 A1 | 9/2004 | Eriksson et al. |
| 2004/0175690 A1 | 9/2004 | Mishra et al. |
| 2004/0176787 A1 | 9/2004 | Mishra et al. |
| 2004/0181240 A1 | 9/2004 | Tseng et al. |
| 2004/0191900 A1 | 9/2004 | Mizuno et al. |
| 2004/0193181 A1 | 9/2004 | Bonutti |
| 2004/0219182 A1 | 11/2004 | Gomes et al. |
| 2004/0228901 A1 | 11/2004 | Trieu et al. |
| 2004/0230303 A1 | 11/2004 | Gomes et al. |
| 2004/0230309 A1 | 11/2004 | DiMauro et al. |
| 2005/0026133 A1 | 2/2005 | Nakatsuji et al. |
| 2005/0032015 A1 | 2/2005 | Mcsurdy, Jr. |
| 2005/0038520 A1 | 2/2005 | Bienette et al. |
| 2005/0043805 A1 | 2/2005 | Chudik |
| 2005/0043814 A1 | 2/2005 | Kusanagi et al. |
| 2005/0054595 A1 | 3/2005 | Bienette et al. |
| 2005/0064042 A1 | 3/2005 | Vunjak-novakovic et al. |
| 2005/0079159 A1 | 4/2005 | Shastri et al. |
| 2005/0152882 A1 | 4/2005 | Kizer et al. |
| 2005/0095235 A1 | 5/2005 | Austin et al. |
| 2005/0095666 A1 | 5/2005 | Jhavar et al. |
| 2005/0113736 A1 | 5/2005 | Orr et al. |
| 2005/0113937 A1 | 5/2005 | Binette et al. |
| 2005/0119754 A1 | 6/2005 | Trieu et al. |
| 2005/0123520 A1 | 6/2005 | Eavey et al. |
| 2005/0124038 A1 | 6/2005 | Aguiar et al. |
| 2005/0125077 A1 | 6/2005 | Harmon et al. |
| 2005/0136046 A1 | 6/2005 | Pines et al. |
| 2005/0137600 A1 | 6/2005 | Jacobs et al. |
| 2005/0139656 A1 | 6/2005 | Arnouse |
| 2005/0152886 A1 | 7/2005 | Baugh et al. |
| 2005/0152961 A1 | 7/2005 | Austin et al. |
| 2005/0171470 A1 | 8/2005 | Kucklick et al. |
| 2005/0175657 A1 | 8/2005 | Hunter et al. |
| 2005/0175704 A1 | 8/2005 | Petersen |
| 2005/0175711 A1 | 8/2005 | Kralovec et al. |
| 2005/0177249 A1 | 8/2005 | Kladakis et al. |
| 2005/0186247 A1 | 8/2005 | Hunter et al. |
| 2005/0186283 A1 | 8/2005 | Geistlich et al. |
| 2005/0186673 A1 | 8/2005 | Geistlich et al. |
| 2005/0192532 A1 | 9/2005 | Kucklick et al. |
| 2005/0196387 A1 | 9/2005 | Seyedin et al. |
| 2005/0196460 A1 | 9/2005 | Malinin |
| 2005/0203342 A1 | 9/2005 | Kucklick et al. |
| 2005/0209601 A1 | 9/2005 | Bowman et al. |
| 2005/0209602 A1 | 9/2005 | Bowman et al. |
| 2005/0222687 A1 | 10/2005 | Vunjak-novakovic et al. |
| 2005/0226856 A1 | 10/2005 | Ahlfors |
| 2005/0234298 A1 | 10/2005 | Kucklick et al. |
| 2005/0234485 A1 | 10/2005 | Seegert et al. |
| 2005/0244454 A1 | 11/2005 | Elson et al. |
| 2005/0250697 A1 | 11/2005 | Maubois et al. |
| 2005/0250698 A1 | 11/2005 | Maubois et al. |
| 2005/0251268 A1 | 11/2005 | Truncale |
| 2005/0265980 A1 | 12/2005 | Chen et al. |
| 2005/0267584 A1 | 12/2005 | Burdulis, Jr. et al. |
| 2005/0273129 A1 | 12/2005 | Michels et al. |
| 2005/0287218 A1 | 12/2005 | Chaouk et al. |
| 2005/0288796 A1 | 12/2005 | Awad et al. |
| 2006/0008530 A1 | 1/2006 | Seyedin et al. |

(56) References Cited

U.S. PATENT DOCUMENTS

| | | |
|---|---|---|
| 2006/0009779 A1 | 1/2006 | Collins et al. |
| 2006/0019389 A1 | 1/2006 | Yayon et al. |
| 2006/0024373 A1 | 2/2006 | Shahar et al. |
| 2006/0024826 A1 | 2/2006 | Bonassar et al. |
| 2006/0029679 A1 | 2/2006 | Dolecek |
| 2006/0041270 A1 | 2/2006 | Lenker et al. |
| 2006/0073588 A1 | 4/2006 | Adkisson et al. |
| 2006/0078872 A1 | 4/2006 | Taguchi et al. |
| 2006/0099706 A1 | 5/2006 | Massey et al. |
| 2006/0111738 A1 | 5/2006 | Wenchell |
| 2006/0111778 A1 | 5/2006 | Michalow |
| 2006/0128016 A1 | 6/2006 | Tokushima et al. |
| 2006/0134093 A1 | 6/2006 | Ronfard |
| 2006/0134094 A2 | 6/2006 | Delmotte et al. |
| 2006/0147547 A1 | 7/2006 | Yayon |
| 2006/0153815 A1 | 7/2006 | Seyda et al. |
| 2006/0183224 A1 | 8/2006 | Aerts et al. |
| 2006/0195188 A1 | 8/2006 | O'Driscoll et al. |
| 2006/0210643 A1 | 9/2006 | Truncale et al. |
| 2006/0216822 A1 | 9/2006 | Mizuno et al. |
| 2006/0228391 A1 | 10/2006 | Seyedin et al. |
| 2006/0240064 A9 | 10/2006 | Hunter et al. |
| 2006/0240555 A1 | 10/2006 | Ronfard |
| 2006/0251631 A1 | 11/2006 | Adkisson, IV et al. |
| 2006/0264966 A1 | 11/2006 | Armstrong |
| 2006/0275273 A1 | 12/2006 | Seyedin et al. |
| 2006/0281173 A1 | 12/2006 | Fakuda et al. |
| 2006/0292131 A1 | 12/2006 | Binette et al. |
| 2007/0014867 A1 | 1/2007 | Kusanagi et al. |
| 2007/0031471 A1 | 2/2007 | Peyman |
| 2007/0038299 A1 | 2/2007 | Stone |
| 2007/0041952 A1 | 2/2007 | Guilak et al. |
| 2007/0077236 A1 | 4/2007 | Osther |
| 2007/0087032 A1 | 4/2007 | Chang et al. |
| 2007/0098759 A1 | 5/2007 | Malinin |
| 2007/0106394 A1 | 5/2007 | Chen |
| 2007/0128155 A1 | 6/2007 | Seyedin et al. |
| 2007/0184550 A1 | 8/2007 | Miyauchi et al. |
| 2007/0191781 A1 | 8/2007 | Richards et al. |
| 2007/0212389 A1 | 9/2007 | Weiss et al. |
| 2007/0213660 A1 | 9/2007 | Richards et al. |
| 2007/0250164 A1 | 10/2007 | Troxel |
| 2007/0292945 A1 | 12/2007 | Lin et al. |
| 2007/0299517 A1 | 12/2007 | Davisson |
| 2008/0009942 A1 | 1/2008 | Mizuno et al. |
| 2008/0031934 A1 | 2/2008 | MacPhee et al. |
| 2008/0033331 A1 | 2/2008 | MacPhee et al. |
| 2008/0033332 A1 | 2/2008 | MacPhee et al. |
| 2008/0033333 A1 | 2/2008 | MacPhee et al. |
| 2008/0039940 A1 | 2/2008 | Hashimoto et al. |
| 2008/0039954 A1 | 2/2008 | Long et al. |
| 2008/0051624 A1 | 2/2008 | Bonutti |
| 2008/0065210 A1 | 3/2008 | McKay |
| 2008/0071385 A1 | 3/2008 | Binette et al. |
| 2008/0081369 A1 | 4/2008 | Adkisson, IV et al. |
| 2008/0103564 A1 | 5/2008 | Burkinshaw et al. |
| 2008/0113007 A1 | 5/2008 | Kurihara et al. |
| 2008/0153157 A1 | 6/2008 | Yao et al. |
| 2008/0154370 A1 | 6/2008 | Mathies |
| 2008/0199429 A1 | 8/2008 | Hollander et al. |
| 2008/0274157 A1 | 11/2008 | Vunjak-Novakovic et al. |
| 2008/0299214 A1 | 12/2008 | Seyedin et al. |
| 2009/0012629 A1 | 1/2009 | Yao et al. |
| 2009/0069901 A1 | 3/2009 | Truncale et al. |
| 2009/0143867 A1 | 6/2009 | Gage et al. |
| 2009/0149893 A1 | 6/2009 | Semler et al. |
| 2009/0155229 A1 | 6/2009 | Yayon |
| 2009/0181092 A1 | 7/2009 | Thorne et al. |
| 2009/0181093 A1 | 7/2009 | Thorne et al. |
| 2009/0181892 A1 | 7/2009 | Thorne et al. |
| 2009/0214614 A1 | 8/2009 | Everland et al. |
| 2009/0291112 A1 | 11/2009 | Truncale |
| 2009/0319045 A1 | 12/2009 | Truncale et al. |
| 2010/0015202 A1 | 1/2010 | Semler et al. |
| 2010/0086594 A1 | 4/2010 | Amit et al. |
| 2010/0121311 A1 | 5/2010 | Seegert et al. |
| 2010/0168856 A1 | 7/2010 | Long et al. |
| 2010/0209397 A1 | 8/2010 | Maor |
| 2010/0209408 A1 | 8/2010 | Stephen A. et al. |
| 2010/0274362 A1 | 10/2010 | Yayon et al. |
| 2010/0303765 A1 | 12/2010 | Athanasiou et al. |
| 2010/0322994 A1 | 12/2010 | Kiser et al. |
| 2011/0009963 A1 | 1/2011 | Binnette et al. |
| 2011/0052705 A1 | 3/2011 | Malinin |
| 2011/0070271 A1 | 3/2011 | Truncale et al. |
| 2011/0091517 A1 | 4/2011 | Binette et al. |
| 2011/0097381 A1 | 4/2011 | Binette et al. |
| 2011/0166669 A1 | 7/2011 | Truncale et al. |
| 2011/0177134 A1 | 7/2011 | Harmon et al. |
| 2011/0196508 A1 | 8/2011 | Truncale et al. |
| 2011/0256095 A1 | 10/2011 | Seyedin et al. |
| 2012/0009224 A1 | 1/2012 | Kizer et al. |
| 2012/0009270 A1 | 1/2012 | Kizer et al. |
| 2012/0107384 A1 | 5/2012 | Yao et al. |
| 2012/0156265 A1 | 6/2012 | Binette et al. |
| 2012/0183586 A1 | 7/2012 | Yao et al. |
| 2012/0232588 A1* | 9/2012 | Stocchero ........ A61B 17/06166 606/228 |
| 2012/0239146 A1 | 9/2012 | Kizer et al. |
| 2013/0330415 A1 | 12/2013 | Yao et al. |
| 2014/0178343 A1 | 6/2014 | Yao et al. |

FOREIGN PATENT DOCUMENTS

| | | |
|---|---|---|
| AU | 2008240191 B2 | 1/2014 |
| CA | 2261292 C | 2/1998 |
| CA | 2285382 A1 | 10/1998 |
| CA | 2261292 A1 | 1/1999 |
| CA | 2441994 A1 | 10/2002 |
| CA | 2445356 A1 | 4/2004 |
| CA | 2445356 C | 4/2004 |
| CA | 2445558 A1 | 4/2004 |
| CA | 2445558 C | 4/2004 |
| CA | 2449227 A1 | 5/2004 |
| CA | 2449227 C | 5/2004 |
| CA | 2522133 A1 | 11/2004 |
| CA | 2522133 C | 11/2004 |
| CA | 2475905 A1 | 2/2005 |
| CA | 2475905 C | 2/2005 |
| CA | 2480712 A1 | 3/2005 |
| CA | 2487029 A1 | 5/2005 |
| CA | 2487042 A1 | 6/2005 |
| CA | 2496184 A1 | 8/2005 |
| CA | 2563082 A1 | 11/2005 |
| CA | 2570521 A1 | 3/2006 |
| CA | 2631520 A1 | 6/2007 |
| CA | 2708147 A1 | 6/2009 |
| CA | 2717725 A1 | 9/2009 |
| CA | 2684040 C | 12/2016 |
| EP | 0006216 A1 | 1/1980 |
| EP | 0133934 A2 | 3/1985 |
| EP | 0341007 A2 | 11/1989 |
| EP | 0493387 B1 | 10/1993 |
| EP | 0592242 A1 | 4/1994 |
| EP | 0641007 A2 | 3/1995 |
| EP | 0654078 B1 | 5/1995 |
| EP | 0669138 A2 | 8/1995 |
| EP | 0610423 B1 | 5/1997 |
| EP | 0877632 B1 | 9/1997 |
| EP | 0867193 A2 | 9/1998 |
| EP | 0920490 A2 | 6/1999 |
| EP | 01010356 A1 | 6/2000 |
| EP | 1132061 A2 | 9/2001 |
| EP | 1142581 A2 | 10/2001 |
| EP | 867193 B1 | 12/2002 |
| EP | 1264607 A1 | 12/2002 |
| EP | 1003568 B1 | 4/2003 |
| EP | 0592242 B1 | 7/2003 |
| EP | 0906069 B1 | 2/2004 |
| EP | 1410810 A1 | 4/2004 |
| EP | 1410811 A1 | 4/2004 |
| EP | 1433423 A1 | 6/2004 |
| EP | 1471140 A1 | 10/2004 |
| EP | 1506790 A1 | 2/2005 |

(56) References Cited

FOREIGN PATENT DOCUMENTS

| | | |
|---|---|---|
| EP | 1512739 A1 | 3/2005 |
| EP | 1535578 A1 | 6/2005 |
| EP | 1535633 A1 | 6/2005 |
| EP | 1537883 A2 | 6/2005 |
| EP | 1538196 A1 | 6/2005 |
| EP | 1537883 A3 | 8/2005 |
| EP | 1561481 A2 | 8/2005 |
| EP | 1599126 A2 | 11/2005 |
| EP | 1387703 B1 | 7/2006 |
| EP | 1303184 B1 | 9/2006 |
| EP | 1410810 B1 | 1/2007 |
| EP | 1788077 A1 | 5/2007 |
| EP | 1561481 A3 | 3/2008 |
| EP | 1537883 B1 | 4/2008 |
| EP | 1618178 B1 | 7/2008 |
| EP | 1410811 B1 | 10/2008 |
| EP | 1433423 B1 | 12/2008 |
| EP | 2335650 A1 | 6/2011 |
| EP | 2338441 A1 | 6/2011 |
| EP | 2338442 A1 | 6/2011 |
| EP | 2338533 A1 | 6/2011 |
| EP | 1691727 B1 | 7/2011 |
| EP | 2101681 B1 | 8/2011 |
| EP | 1958651 B1 | 10/2011 |
| EP | 1561481 B1 | 3/2012 |
| EP | 1753860 B1 | 4/2012 |
| EP | 2335650 B1 | 10/2012 |
| EP | 2338441 B1 | 1/2013 |
| EP | 2338442 B1 | 1/2013 |
| GB | 2105198 A | 3/1983 |
| GB | 2175507 A | 12/1986 |
| GB | 2404607 A | 9/2005 |
| JP | 59135054 A | 8/1984 |
| JP | 10036534 A | 2/1998 |
| JP | 2001519700 T | 10/2001 |
| JP | 2002233567 A | 8/2002 |
| JP | 2003180699 A | 7/2003 |
| JP | 2004136096 A | 5/2004 |
| JP | 2006230749 A | 9/2006 |
| JP | 2003102755 A | 4/2008 |
| WO | WO-8002501 A1 | 11/1980 |
| WO | WO-8505274 A1 | 12/1985 |
| WO | WO-9000060 A1 | 1/1990 |
| WO | WO-9101711 A1 | 2/1991 |
| WO | WO-9209697 A1 | 6/1992 |
| WO | WO-9603112 A1 | 2/1996 |
| WO | WO-9603160 A1 | 2/1996 |
| WO | WO-9639170 A1 | 12/1996 |
| WO | WO-9711090 A1 | 3/1997 |
| WO | WO-9726847 A1 | 7/1997 |
| WO | WO-1997026847 A1 | 7/1997 |
| WO | WO-9804681 A2 | 2/1998 |
| WO | WO-9844874 A1 | 10/1998 |
| WO | WO-9907417 A1 | 2/1999 |
| WO | WO-9951164 A1 | 10/1999 |
| WO | WO-0006216 A1 | 2/2000 |
| WO | WO-06041723 A1 | 3/2000 |
| WO | WO-0029484 A1 | 5/2000 |
| WO | WO-06059198 A1 | 5/2000 |
| WO | WO-0048837 A1 | 8/2000 |
| WO | WO-0056251 A1 | 9/2000 |
| WO | WO-0062832 A1 | 10/2000 |
| WO | WO-0074741 A2 | 12/2000 |
| WO | WO-0074741 A3 | 12/2000 |
| WO | WO-0102030 A2 | 1/2001 |
| WO | WO-0105443 A1 | 1/2001 |
| WO | WO-0110356 A2 | 2/2001 |
| WO | WO-0123014 A2 | 4/2001 |
| WO | WO-2001023014 A1 | 4/2001 |
| WO | WO-0167961 A1 | 9/2001 |
| WO | WO-0168811 A2 | 9/2001 |
| WO | WO-0168811 A3 | 9/2001 |
| WO | WO-0185225 A2 | 11/2001 |
| WO | WO-0197872 A1 | 12/2001 |
| WO | WO-0185225 A3 | 3/2002 |
| WO | WO-0224244 A2 | 3/2002 |
| WO | WO-02067856 A2 | 9/2002 |
| WO | WO-02076285 A2 | 10/2002 |
| WO | WO-02080991 A2 | 10/2002 |
| WO | WO-02089868 A1 | 11/2002 |
| WO | WO-03077794 A2 | 9/2003 |
| WO | WO-03093433 A2 | 11/2003 |
| WO | WO-03100417 A1 | 12/2003 |
| WO | WO-2004028547 A1 | 4/2004 |
| WO | WO-2004028584 A1 | 4/2004 |
| WO | WO-03093433 A3 | 7/2004 |
| WO | WO-2004078032 A2 | 9/2004 |
| WO | WO-2004078032 A3 | 9/2004 |
| WO | WO-2004078035 A2 | 9/2004 |
| WO | WO-2004078955 A1 | 9/2004 |
| WO | WO-2004096983 A2 | 11/2004 |
| WO | WO-2004105576 A2 | 12/2004 |
| WO | WO-2004110308 A2 | 12/2004 |
| WO | WO-2004110512 A2 | 12/2004 |
| WO | WO-2005011765 A1 | 2/2005 |
| WO | WO-2005018491 A2 | 3/2005 |
| WO | WO-2004110512 A3 | 5/2005 |
| WO | WO-2005044326 A1 | 5/2005 |
| WO | WO-2005058207 A1 | 6/2005 |
| WO | WO-2005060987 A1 | 7/2005 |
| WO | WO-2005061018 A1 | 7/2005 |
| WO | WO-2005061019 A2 | 7/2005 |
| WO | WO-2005065079 A2 | 7/2005 |
| WO | WO-2005081870 A2 | 9/2005 |
| WO | WO-2005092208 A1 | 10/2005 |
| WO | WO-2005092405 A1 | 10/2005 |
| WO | WO-2005110278 A2 | 11/2005 |
| WO | WO-2005113751 A1 | 12/2005 |
| WO | WO-2006002253 A2 | 1/2006 |
| WO | WO-2006002253 A3 | 1/2006 |
| WO | WO-2006017176 A2 | 2/2006 |
| WO | WO-2006033698 A2 | 3/2006 |
| WO | WO-2006039484 A2 | 4/2006 |
| WO | WO-2006068972 A2 | 6/2006 |
| WO | WO-2006033698 A3 | 7/2006 |
| WO | WO-2006090372 A2 | 8/2006 |
| WO | WO-2006090372 A3 | 8/2006 |
| WO | WO-2006113642 A1 | 11/2006 |
| WO | WO-2006121612 A1 | 11/2006 |
| WO | WO-2005081870 A3 | 12/2006 |
| WO | WO-2006039484 A3 | 1/2007 |
| WO | WO-2007025290 A2 | 3/2007 |
| WO | WO-2007054939 A2 | 5/2007 |
| WO | WO-2007067637 A2 | 6/2007 |
| WO | WO-2007089942 A2 | 8/2007 |
| WO | WO-2007089948 A2 | 8/2007 |
| WO | WO-2007102149 A2 | 9/2007 |
| WO | WO-2007025290 A3 | 10/2007 |
| WO | WO-2007115336 A2 | 10/2007 |
| WO | WO-2007143726 A2 | 12/2007 |
| WO | WO-2007089948 A3 | 1/2008 |
| WO | WO-2008019127 A2 | 2/2008 |
| WO | WO-2008019128 A2 | 2/2008 |
| WO | WO-2008019129 A2 | 2/2008 |
| WO | WO-2008021127 A2 | 2/2008 |
| WO | WO-2008079194 A1 | 7/2008 |
| WO | WO-2008079613 A1 | 7/2008 |
| WO | WO-2008106254 A2 | 9/2008 |
| WO | WO-2008128075 A1 | 10/2008 |
| WO | WO-2009039469 A1 | 3/2009 |
| WO | WO-2009076164 A2 | 6/2009 |
| WO | WO-2009111069 A1 | 9/2009 |
| WO | WO-2010078040 A1 | 7/2010 |

OTHER PUBLICATIONS

Farr et al., Zimmer Technical Memo, 2010, retrieved from the internet: www.zimmer.com/content/dam/zimmer-web/documents/en-US/pdf/medical-professionals/reimbursement/product/DeNovo_Chondral_Defect_Repair_White_Paper_05_2010.pdf.*

Bush et al., OsteoArthritis and Cartilage (2003), vol. 11, pp. 242-251, The volume and morphology of chondrocytes within non-degradable and degenerate human articular cartilage.*

(56) References Cited

OTHER PUBLICATIONS

Gomoll et al., Cartilage (2011) vol. 2, Issue 4, pp. 389-393, Preoperative Measurement of Cartilage Defects by MRI Underestimates Lesion Size.*
Moyad et al., Cartilage (2011), vol. 2, Issue 3, pp. 226-236, Cartilage Injuries in the Adult Knee: Evaluation and Management.*
Pernodet et al., Pore size of agarose gels by atomic force microscopy, Electrophoresis, 1997, vol. 18, pp. 55-58.*
Adkisson et al., The Potential of Human Allogeneic Juvenile Chondrocytes for Restoration of Articular Cartilage, The A,merican Journal of Sports Medicine, vol. 38, No. 7, 2010, pp. 1324-1333.*
Schon et al., Validation of a high-throughput microtissue fabrication process for 3D assembly of tissue engineered cartilage constructs, Cell Tissue Res., 2012, vol. 347: 629-642.*
Explant definition, Merriam-Webster, retrieved from the internet (Jul. 16, 2018):www.merriam-webster.com/dictionary/explant.*
"U.S. Appl. No. 12/101,553, Final Office Action dated May 5, 2015", 8 pgs.
"U.S. Appl. No. 12/101,553, Non Final Office Action dated Nov. 19, 2014", 8 pgs.
"U.S. Appl. No. 12/101,553, Response filed Feb. 12, 2015 to Non Final Office Action dated Nov. 19, 2014", 14 pgs.
"U.S. Appl. No. 13/327,265, Non Final Office Action dated Nov. 19, 2014", 10 pgs.
"U.S. Appl. No. 13/327,265, Response filed Feb. 12, 2015 to Non-Final Office Action dated Nov. 19, 2014", 13 pgs.
"U.S. Appl. No. 13/951,762, Final Office Action dated Nov. 12, 2014", 6 pgs.
"U.S. Appl. No. 13/951,762, Response filed Sep. 9, 2014 to Non-Final Office Action dated Jun. 9, 2014", 12 pgs.
"Canadian Application Serial No. 2,684,040, Office Action dated Mar. 12, 2015", 3 pgs.
"European Application Serial No. 08745639.8, Examination Notification Art. 94(3) dated Apr. 30, 2015", 5 pgs.
"European Application Serial No. 08745639.8, Examination Notification Art. 94(3) dated Oct. 24, 2014", 4 pgs.
"U.S. Appl. No. 10/374,772, 1.132 Declaration of Julia Hwang filed Jan. 5, 2009", 3 pgs.
"U.S. Appl. No. 10/374,772, Response filed Jan. 6, 2009 to Non-Final Office Action dated Sep. 2, 2008", 5 pgs.
"U.S. Appl. No. 10/874,402, Final Office Action dated Feb. 22, 2011", 10 pgs.
"U.S. Appl. No. 10/874,402, Final Office Action dated Apr. 17, 2009", 17 pgs.
"U.S. Appl. No. 10/874,402, Final Office Action dated Apr. 19, 2010", 13 pgs.
"U.S. Appl. No. 10/874,402, Non Final Office Action dated Apr. 10, 2008", 9 pgs.
"U.S. Appl. No. 10/874,402, Non Final Office Action dated Sep. 22, 2010", 11 pgs.
"U.S. Appl. No. 10/874,402, Non Final Office Action dated Oct. 27, 2009", 15 pgs.
"U.S. Appl. No. 11/010,779, Examiner Interview Summary dated Apr. 5, 2010", 4 pgs.
"U.S. Appl. No. 11/010,779, Examiner Interview Summary dated Dec. 7, 2009", 3 pgs.
"U.S. Appl. No. 11/010,779, Non Final Office Action dated Feb. 17, 2010", 4 pgs.
"U.S. Appl. No. 11/010,779, Non Final Office Action dated Apr. 15, 2009", 8 pgs.
"U.S. Appl. No. 11/010,779, Notice of Allowance dated Jul. 8, 2010", 4 pgs.
"U.S. Appl. No. 11/010,779, Response filed Feb. 12, 2009 to Restriction Requirement dated Jan. 12, 2009", 3 pgs.
"U.S. Appl. No. 11/010,779, Response filed Apr. 19, 2010 to Non Final Office Action dated Feb. 17, 2010", 13 pgs.
"U.S. Appl. No. 11/010,779, Response filed Jul. 15, 2009 to Non Final Office Action dated Apr. 15, 2009", 16 pgs.
"U.S. Appl. No. 11/010,779, Response filed Dec. 3, 2009 to Non Final Office Action dated Apr. 15, 2009", 13 pgs.
"U.S. Appl. No. 11/010,779, Restriction Requirement dated Jan. 12, 2009", 16 pgs.
"U.S. Appl. No. 11/413,419, Final Office Action dated Aug. 25, 2009", 13 pgs.
"U.S. Appl. No. 11/413,419, Non Final Office Action dated Jun. 26, 2008", 12 pgs.
"U.S. Appl. No. 11/613,250, Advisory Action dated Jul. 9, 2008", 13 pgs.
"U.S. Appl. No. 11/613,250, Final Office Action dated Apr. 15, 2008", 9 pgs.
"U.S. Appl. No. 11/613,250, Non Final Office Action dated Mar. 28, 2011", 9 pgs.
"U.S. Appl. No. 11/613,250, Non Final Office Action dated May 28, 2009", 12 pgs.
"U.S. Appl. No. 11/613,250, Non Final Office Action dated Sep. 20, 2007", 17 pgs.
"U.S. Appl. No. 11/613,250, Non Final Office Action dated Sep. 21, 2010", 15 pgs.
"U.S. Appl. No. 11/613,250, Non Final Office Action dated Oct. 16, 2008", 11 pgs.
"U.S. Appl. No. 11/613,250, Non Final Office Action dated Dec. 23, 2009", 15 pgs.
"U.S. Appl. No. 11/613,250, Notice of Allowance dated Dec. 23, 2011", 9 pgs.
"U.S. Appl. No. 11/613,250, Response filed Jan. 16, 2009 to Non Final Office Action dated Oct. 16, 2008", 9 pgs.
"U.S. Appl. No. 11/613,250, Response filed Jan. 19, 2011 to Non Final Office Action dated Sep. 21, 2010", 13 pgs.
"U.S. Appl. No. 11/613,250, Response filed Mar. 23, 2010 to Non Final Office Action dated Dec. 23, 2009", 9 pgs.
"U.S. Appl. No. 11/613,250, Response filed Jun. 16, 2008 to Final Office Action dated Apr. 15, 2008", 19 pgs.
"U.S. Appl. No. 11/613,250, Response filed Aug. 28, 2009 to Non Final Office Action dated May 28, 2009", 12 pgs.
"U.S. Appl. No. 11/613,250, Response filed Sep. 28, 2011 to Non Final Office Action dated Mar. 28, 2011", 9 pgs.
"U.S. Appl. No. 11/613,250, Response filed Dec. 20, 2007 to Non Final Office Action dated Sep. 20, 2007", 19 pgs.
"U.S. Appl. No. 11/613,319, Advisory Action dated Jan. 19, 2010", 3 pgs.
"U.S. Appl. No. 11/613,319, Final Office Action dated Jun. 18, 2012", 11 pgs.
"U.S. Appl. No. 11/613,319, Final Office Action dated Oct. 26, 2009", 7 pgs.
"U.S. Appl. No. 11/613,319, Information Disclosure Statement mailed Mar. 20, 2007", 9 pgs.
"U.S. Appl. No. 11/613,319, Informational Disclosure Statement mailed Jun. 30, 2008", 6 pgs.
"U.S. Appl. No. 11/613,319, Information Disclosure Statement mailed Sep. 3, 2010", 5 pgs.
"U.S. Appl. No. 11/613,319, Informational Disclosure Statement mailed Dec. 20, 2007", 6 pgs.
"U.S. Appl. No. 11/613,319, Non Final Office Action dated Mar. 13, 2009", 7 pgs.
"U.S. Appl. No. 11/613,319, Non Final Office Action dated Dec. 29, 2011", 9 pgs.
"U.S. Appl. No. 11/613,319, Response filed Jan. 26, 2009 to Restriction Requirement dated Dec. 26, 2008", 7 pgs.
"U.S. Appl. No. 11/613,319, Response filed Jan. 26, 2010 to Advisory Action dated Jan. 19, 2010", 9 pgs.
"U.S. Appl. No. 11/613,319, Response filed Mar. 29, 2012 to Non Final Office Action dated Dec. 29, 2011", 15 pgs.
"U.S. Appl. No. 11/613,319, Response filed Jun. 11, 2009 to Non Final Office Action dated Mar. 13, 2009", 8 pgs.
"U.S. Appl. No. 11/613,319, Response filed Sep. 17, 2012 to Final Office Action dated Jun. 18, 2012", 19 pgs.
"U.S. Appl. No. 11/613,319, Response filed Dec. 7, 2009 to Final Office Action dated Oct. 26, 2009", 8 pgs.
"U.S. Appl. No. 11/613,319, Restriction Requirement dated Dec. 26, 2008", 6 pgs.
"U.S. Appl. No. 11/613,456, Advisory Action dated Aug. 11, 2009", 3 pgs.

(56) References Cited

OTHER PUBLICATIONS

"U.S. Appl. No. 11/613,456, Final Office Action dated Jun. 4, 2009", 7 pgs.
"U.S. Appl. No. 11/613,456, Non Final Office Action dated Jan. 23, 2009", 6 pgs.
"U.S. Appl. No. 11/613,456, Non Final Office Action dated Sep. 11, 2009", 5 pgs.
"U.S. Appl. No. 11/613,456, Notice of Allowance dated Jan. 19, 2010", 5 pgs.
"U.S. Appl. No. 11/613,456, Response filed Apr. 3, 2009 to Non Final Office Action dated Jan. 23, 2009", 8 pgs.
"U.S. Appl. No. 11/613,456, Response filed Aug. 4, 2009 to Final Office Action dated Jun. 4, 2009", 9 pgs.
"U.S. Appl. No. 11/613,456, Response filed Nov. 6, 2008 to Restriction Requirement dated Oct. 7, 2008", 7 pgs.
"U.S. Appl. No. 11/613,456, Response filed Dec. 7, 2009 to Non Final Office Action dated Sep. 11, 2009", 9 pgs.
"U.S. Appl. No. 11/613,456, Restriction Requirement dated Oct. 7, 2008", 6 pgs.
"U.S. Appl. No. 12/063,291, Final Office Action dated Mar. 15, 2012", 10 pgs.
"U.S. Appl. No. 12/063,291, Final Office Action dated Mar. 22, 2011", 8 pgs.
"U.S. Appl. No. 12/063,291, Non Final Office Action dated Sep. 15, 2010", 6 pgs.
"U.S. Appl. No. 12/063,291, Notice of Allowance dated Mar. 4, 2013", 7 pgs.
"U.S. Appl. No. 12/063,291, Notice of Allowance dated Aug. 8, 2012", 9 pgs.
"U.S. Appl. No. 12/063,291, Notice of Allowance dated Oct. 11, 2012", 8 pgs.
"U.S. Appl. No. 12/063,291, Preliminary Amendment filed Feb. 8, 2008", 9 pgs.
"U.S. Appl. No. 12/063,291, Response filed Jan. 21, 2011 to Non Final Office Action dated Sep. 15, 2010", 12 pgs.
"U.S. Appl. No. 12/063,291, Response filed Jul. 16, 2012 to Final Office Action dated Mar. 15, 2012", 13 pgs.
"U.S. Appl. No. 12/063,291, Response filed Sep. 22, 2011 to Final Office Action dated Mar. 22, 2011", 10 pgs.
"U.S. Appl. No. 12/101,553, Final Office Action dated Sep. 14, 2012", 9 pgs.
"U.S. Appl. No. 12/101,553, Final Office Action dated Dec. 28, 2012", 9 pgs.
"U.S. Appl. No. 12/101,553, Non Final Office Action dated Nov. 9, 2011", 8 pgs.
"U.S. Appl. No. 12/101,553, Response filed Mar. 13, 2013 to Final Office Action dated Dec. 28, 2012", 15 pgs.
"U.S. Appl. No. 12/101,553, Response filed May 9, 2012 to Non Final Office Action dated Nov. 9, 2011", 14 pgs.
"U.S. Appl. No. 12/101,553, Response filed Aug. 15, 2011 to Restriction Requirement dated Jul. 13, 2011", 11 pgs.
"U.S. Appl. No. 12/101,553, Restriction Requirement dated Jul. 13, 2011", 17 pgs.
"U.S. Appl. No. 12/751,230, Non Final Office Action dated Sep. 1, 2010", 9 pgs.
"U.S. Appl. No. 12/751,230, Preliminary Amendment filed Mar. 31, 2010", 7 pgs.
"U.S. Appl. No. 12/751,230, Response filed Jul. 30, 2010 to Restriction Requirement dated Jul. 21, 2010", 5 pgs.
"U.S. Appl. No. 12/751,230, Restriction Requirement dated Jul. 21, 2010", 53 pgs.
"U.S. Appl. No. 12/861,404, Final Office Action dated Dec. 6, 2013", 7 pgs.
"U.S. Appl. No. 12/861,404, Non Final Office Action dated May 16, 2012", 7 pgs.
"U.S. Appl. No. 12/861,404, Preliminary Amendment filed Aug. 23, 2010", 6 pgs.
"U.S. Appl. No. 12/861,404, Response filed Jan. 10, 2014 to Final Office Action dated Dec. 6, 2013", 6 pgs.

"U.S. Appl. No. 12/861,404, Response filed Apr. 1, 2013 to Non Final Office Action dated May 16, 2012", 6 pgs.
"U.S. Appl. No. 12/976,689, Non Final Office Action dated May 17, 2012", 7 pgs.
"U.S. Appl. No. 12/976,689, Response filed Apr. 1, 2013 to Non Final Office Action dated May 17, 2012", 7 pgs.
"U.S. Appl. No. 12/976,704, Non Final Office Action dated Sep. 12, 2013", 10 pgs.
"U.S. Appl. No. 12/976,704, Response filed Dec. 10, 2013 to Non-Final Office Action dated Sep. 12, 2013", 7 pgs.
"U.S. Appl. No. 12/976,711, Examiner Interview Summary dated Apr. 8, 2013", 3 pgs.
"U.S. Appl. No. 12/976,711, Examiner Interview Summary dated Jul. 25, 2013", 3 pgs.
"U.S. Appl. No. 12/976,711, Examiner Interview Summary dated Nov. 15, 2012", 3 pgs.
"U.S. Appl. No. 12/976,711, Final Office Action dated Apr. 17, 2013", 6 pgs.
"U.S. Appl. No. 12/976,711, Non Final Office Action dated Aug. 1, 2013", 5 pgs.
"U.S. Appl. No. 12/976,711, Non Final Office Action dated Dec. 12, 2012", 9 pgs.
"U.S. Appl. No. 12/976,711, Notice of Allowance dated Aug. 23, 2013", 6 pgs.
"U.S. Appl. No. 12/976,711, Response filed Apr. 2, 2013 to Non Final Office Action dated Dec. 12, 2012", 8 pgs.
"U.S. Appl. No. 12/976,711, Response filed Jul. 22, 2013 to Final Office Action dated Apr. 17, 2013", 6 pgs.
"U.S. Appl. No. 12/976,711, Response filed Aug. 9, 2013 to Non Final Office Action dated Aug. 1, 2013", 6 pgs.
"U.S. Appl. No. 12/976,711, Response filed Aug. 29, 2012 to Restriction Requirement dated May 29, 2012", 4 pgs.
"U.S. Appl. No. 12/976,711, Response filed Dec. 3, 2012 to Restriction Requirement dated Oct. 4, 2012", 6 pgs.
"U.S. Appl. No. 12/976,711, Supplemental Notice of Allowability dated Nov. 21, 2013", 2 pgs.
"U.S. Appl. No. 12/976,711, Supplemental Notice of Allowability dated Dec. 20, 2013", 2 pgs.
"U.S. Appl. No. 12/976,711. Restriction Requirement dated May 29, 2012", 6 pgs.
"U.S. Appl. No. 12/976,711. Restriction Requirement dated Oct. 4, 2012", 6 pgs.
"U.S. Appl. No. 13/327,238, Non Final Office Action dated Jan. 2, 2013", 8 pgs.
"U.S. Appl. No. 13/327,238, Notice of Allowance dated Apr. 30, 2013", 6 pgs.
"U.S. Appl. No. 13/327,238, Preliminary Amendment filed Jun. 1, 2012", 6 pgs.
"U.S. Appl. No. 13/327,238, Response filed Apr. 2, 2013 to Non Final Office Action dated Apr. 2, 2013", 6 pgs.
"U.S. Appl. No. 13/327,238, Response filed Dec. 7, 2012 to Restriction Requirement dated Sep. 7, 2012", 6 pgs.
"U.S. Appl. No. 13/327,238, Restriction Requirement dated Sep. 7, 2012", 11 pgs.
"U.S. Appl. No. 13/327,265, Final Office Action dated Jan. 31, 2013", 8 pgs.
"U.S. Appl. No. 13/327,265, Non Final Office Action dated Apr. 2, 2012", 10 pgs.
"U.S. Appl. No. 13/327,265, Response filed May 21, 2013 to Final Office Action dated Jan. 21, 2013", 7 pgs.
"U.S. Appl. No. 13/327,265, Response filed Sep. 4, 2012 to Non Final Office Action dated Apr. 2, 2012", 7 pgs.
"U.S. Appl. No. 13/327,286, Non Final Office Action dated Feb. 7, 2013", 9 pgs.
"U.S. Appl. No. 13/327,286, Notice of Allowance dated Apr. 24, 2013", 6 pgs.
"U.S. Appl. No. 13/327,286, Preliminary Amendment filed Jun. 1, 2012", 7 pgs.
"U.S. Appl. No. 13/327,286, Response filed Apr. 2, 2013 to Non Final Office Action dated Feb. 7, 2013", 6 pgs.
"U.S. Appl. No. 13/327,286, Supplemental Notice of Allowability dated May 15, 2013", 2 pgs.

(56) References Cited

OTHER PUBLICATIONS

"U.S. Appl. No. 13/327,286, Supplemental Notice of Allowability dated May 28, 2013", 4 pgs.
"U.S. Appl. No. 13/428,873, Final Office Action dated Dec. 12, 2012", 6 pgs.
"U.S. Appl. No. 13/428,873, Non Final Office Action dated Jul. 18, 2012", 9 pgs.
"U.S. Appl. No. 13/428,873, Notice of Allowance dated Mar. 25, 2013", 6 pgs.
"U.S. Appl. No. 13/428,873, Preliminary Amendment filed Mar. 23, 2012", 6 pgs.
"U.S. Appl. No. 13/428,873, Response filed Feb. 12, 2013 to Final Office Action dated Dec. 12, 2012", 6 pgs.
"U.S. Appl. No. 13/428,873, Response filed Oct. 17, 2012 to Non Final Office Action dated Jul. 18, 2012", 9 pgs.
"U.S. Appl. No. 13/799,452, Non Final Office Action dated May 21, 2014", 11 pgs.
"U.S. Appl. No. 13/799,452, Response filed Jan. 28, 2014 to Restriction Requirement dated Dec. 24, 2013", 5 pgs.
"U.S. Appl. No. 13/799,452, Restriction Requirement dated Dec. 24, 2013", 9 pgs.
"U.S. Appl. No. 13/951,762, Non Final Office Action dated Sep. 20, 2013", 10 pgs.
"U.S. Appl. No. 13/951,762, Preliminary Amendment filed Jul. 27, 2013", 3 pgs.
"U.S. Appl. No. 13/951,762, Response filed Jan. 21, 2014 to Non-Final office Action dated Sep. 20, 2013", 8 pgs.
"U.S. Appl. No. 13/951,762, Supplemental Preliminary Amendment filed Aug. 22, 2013", 4 pgs.
"Application Serial No. 2008240191, First Examination Report dated Sep. 21, 2012".
"Australian Application Serial No. 2006282754, Examiners First Report dated Nov. 8, 2011", 3 pgs.
"Australian Application Serial No. 2006282754, Response filed May 7, 2013 to First AU Examiner Report dated Nov. 8, 2011", 13 pgs.
"Australian Application Serial No. 2006282754, Subsequent Examiners Report dated Jun. 14, 2013", 3 pgs.
"Australian Application Serial No. 2008240191, Response filed Aug. 22, 2013 to First Examination Report dated Sep. 21, 2012", 12 pgs.
"Canadian Application Serial No. 2,684,040, Office Action dated May 13, 2013", 4 pgs.
"Canadian Application Serial No. 2,684,040, Response filed Oct. 29, 2013 to Office Action dated May 13, 2013", 20 pgs.
"Combine", Merriam-Webster Online Dictionary, [Online] Retrieved From Internet: <http://www.merriam-webster.com/dictionary/combine>, (Jul. 13, 2011), 2 pgs.
"European Application Serial No. 04813849.9, Extended European Search Report dated Apr. 8, 2008", 3 pgs.
"European Application Serial No. 04813849.9, Office Action dated Feb. 16, 2009", 5 pgs.
"European Application Serial No. 04813849.9, Office Action dated Jun. 10, 2011", 3 pgs.
"European Application Serial No. 04813849.9, Office Action dated Jul. 21, 2006", 2 pgs.
"European Application Serial No. 04813849.9, Office Action dated Dec. 30, 2010", 4 pgs.
"European Application Serial No. 04813849.9, Response filed Aug. 20, 2009 to Office Action dated Feb. 16, 2009", 18 pgs.
"European Application Serial No. 04813849.9, Response filed Aug. 21, 2006 to Office Action dated Jul. 21, 2006", 4 pgs.
"European Application Serial No. 07862720.5, Notice of Allowance dated Feb. 25, 2011", 6 pgs.
"European Application Serial No. 07862720.5, Office Action dated Feb. 26, 2010", 3 pgs.
"European Application Serial No. 07862720.5, Response filed Sep. 1, 2010 to Office Action dated Feb. 26, 2010", 10 pgs.
"European Application Serial No. 08745639.8, Extended European Search Report dated Apr. 3, 2013", 7 pgs.
"European Application Serial No. 08745639.8, Response filed Oct. 18, 2013 to Extended European Search Report dated Apr. 3, 2013", 9 pgs.
"European Application Serial No. 11154746.9, Office Action dated Jan. 7, 2013", 3 pgs.
"European Application Serial No. 11154746.9, Office Action dated Mar. 5, 2012", 33 pgs.
"European Application Serial No. 11154746.9, Office Action dated Nov. 15, 2012", 1 pg.
"European Application Serial No. 11154746.9, Response filed Jul. 5, 2012 to Office Action dated Mar. 5, 2012", 7 pgs.
"European Application Serial No. 11154746.9, Response filed Dec. 14, 2012 to Office Action dated Nov. 15, 2012", 4 pgs.
"European Application Serial No. 11154746.9, Search Report dated May 23, 2011", 4 pgs.
"European Application Serial No. 11154747.7, Office Action dated Mar. 5, 2012", 4 pgs.
"European Application Serial No. 11154747.7, Office Action dated Jul. 23, 2012", 3 pgs.
"European Application Serial No. 11154747.7, Office Action dated Nov. 21, 2012", 4 pgs.
"European Application Serial No. 11154747.7, Response filed Jun. 25, 2012 to Office Action dated Mar. 5, 2012", 8 pgs.
"European Application Serial No. 11154747.7, Response filed Sep. 5, 2012 to Office Action dated Jul. 23, 2012", 3 pgs.
"European Application Serial No. 11154747.7, Response filed Dec. 13, 2011 to Extended European Search Report dated May 23, 2011", 3 pgs.
"European Application Serial No. 11154747.7, Response filed Dec. 14, 2012 to Office Action dated Nov. 21, 2012", 4 pgs.
"European Application Serial No. 11154747.7, Search Report dated May 23, 2011", 4 pgs.
"European Application Serial No. 11154748.5, Office Action dated Apr. 13, 2012", 5 pgs.
"European Application Serial No. 11154748.5, Search Report dated May 24, 2011", 4 pgs.
"International Application Serial No. PCT/US2004/041591, International Preliminary Report on Patentability dated Jun. 6, 2012", 4 pgs.
"International Application Serial No. PCT/US2006/033687, International Preliminary Report on Patentability dated Feb. 26, 2008", 7 pgs.
"International Application Serial No. PCT/US2006/033687, Search Report and Written Opinion dated Aug. 8, 2007", 7 pgs.
"International Application Serial No. PCT/US2007/025252, International Preliminary Report on Patentability dated Jun. 23, 2009", 8 pgs.
"International Application Serial No. PCT/US2007/025252, International Search Report dated Apr. 18, 2008", 3 pgs.
"International Application Serial No. PCT/US2007/025252, Written Opinion dated Apr. 18, 2009", 7 pgs.
"International Application Serial No. PCT/US2007/086468, International Preliminary Report on Patentability dated Jun. 23, 2009", 10 pgs.
"International Application Serial No. PCT/US2007/086468, International Search Report dated Jun. 5, 2008", 4 pgs.
"International Application Serial No. PCT/US2007/086468, Written Opinion dated Jun. 20, 2009", 9 pgs.
"International Application Serial No. PCT/US2008/060078, International Search Report dated Sep. 3, 2008", 11 pgs.
"Japanese Application Serial No. 2008-528250, Office Action dated Jun. 22, 2012", with English translation, 5 pgs.
"Japanese Application Serial No. 2008-528250, Response filed Nov. 22, 2012 to Office Action dated Jun. 22, 2012", with English translation, 9 pgs.
"Morsel", Merriam-Webster Online Dictionary, [Online] Retrieved From Internet: <http://www.merriam-webster.com/dictionary/morsel>, (Jul. 13, 2011), 2 pgs.
"NPL text search results cited by USPTO in U.S. Appl. No. 13/951,762", (Sep. 17, 2013), 1 pg.
"Pulverize", Merriam-Webster Online Dictionary, [Online] Retrieved From Internet: <http://www.merriam-webster.com/dictionary/pulverize>, (Jul. 13, 2011), 2 pgs.

(56) References Cited

OTHER PUBLICATIONS

Adibi, Siamak A, et al., "Removal of Glycylglutamine from Plasma by Individual Tissues: Mechanism and Impact on Amino Acid Fluxes in Postabsorption and Starvation", The Journal of Nutrition, Symposium: Nutritional and Hormonal Regulation of Amino Acid Metabolism, (1993), 325-331.
Adkisson, H. Davis, et al., "The Potential of Human Allogeneic Juvenile Chondrocytes for Restoration of Articular Cartilage", The American Journal of Medicine vol. 38, (Apr. 27, 2010), 1324-1333.
Adkisson, H.D.IV, et al., "In Vitro Generation of Scaffold Independent Neocartilage", Clin Ortho Rel Res, No. 391S, (2001), S280-S294.
Akens, M K, et al., "In Vitro Studies of a Photo-oxidized Bovine Articular Cartilage", Journal of Veterinary Medicine, vol. 49, Blackwell Wissenschafts-Verlag, Berlin, (2002), 39-45.
Albrecht, F, "Closure of Joint Cartilage Defects Using Cartilage Fragments and Fibrin Glue", English Abstract of German Article, Fortschr Med, vol. 101, No. 37, (1983), 1650-2.
Albrecht, F., et al., "Closure of Osteochondral Lesions Using Chondral Fragments and Fibrin Adhesive", Arch. Orthop. Trauma surg. 101, (1983), 213-217.
Alfredson, Hakan, et al., "Superior results with continuous passive motion compared to active motion after periosteal transplantation", vol. 7, Knee Surg sports Trautnatol Arthrosc, Springer-Verlag, Germany, (1999), 232-238.
Alston, et al., "New method to prepare autologous fibrin glue on demand", Translational Research vol. 149, (2007), 187-195.
Aston, Jayne E, et al., "Repair of Articular Surfaces by Allografts of Articular and Growth-Plate Cartilage", vol. 68-B, No. I, British Editorial Society of Bone and Joint Surgery, England, (1986), 29-35.
Augenstein, D C, et al., "Effect of Shear on the Death of Two Strains of Mammalian Tissue Cells", vol. XIII, Biotechnology and Bioengineering, USA, (1971), 409-418.
Aulthouse, Amy Lynn, et al., "Expression of the Human Chondrocyte Phenotype in Vitro", vol. 25, No. 7, in Vitro Cellular & Developmental Biology, USA, (1989), 659-668.
Azizkhan, et al., "Chondrocytes contain a growth factor that is localized in the nucleus and is associated with chomatin", Proc. Natl. Acad. Sci., vol. 77, No. 5, (1980), 2762-2766.
Bacsich, P, et al., "The Significance of the Mucoprotein Content on the Survival of Homografts of Cartilage and Cornea", vol. LXII, Part III, P.R.S.E., USA, (1947), 321-329.
Bartlett, W, et al., "Autologous chondrocyte implantation at the knee using a bilayer collagen membrane with bone graft", vol. 87-B, The Journal of Bone & Joint Surgery [Br], London, (2005), 330-332.
Bartlett, W, et al., "Autologous chondrocyte implantation versus matrix-induced autologous chondrocyte implantation for osteochondral defects of the knee", vol. 87-B, No. 5, The Journal of Bone & Joint Surgery [Br], London, (2005), 640-645.
Bassleer, C, et al., "Human Chondrocytes in Tridimensional Culture", vol. 22, No. 3, Pl. I, In Vitro Cellular & Developmental Biology, UK, (1986), 113-119.
Bayliss, Michael, et al., "The properties of proteoglycan prepared from human articular cartilage by using 1 associative caesium chloride gradients of high and low starting densities", Biochem. J., vol. 232, Great Britain, (1985), 111-117.
Behrens, Peter, et al., "Matrix-associated autologous chondrocyte trnasplantationlimplantation (MACTIMACI)-5-year follow-up", vol. 13, The Knee, Elsevier, UK, (2006), 194-202.
Bentley, George, et al., "Homotransplantation of isolated epiphyseal and articular cartilage chondrocytes into joint surfaces of rabbits", Nature 230, (1971), 385-388.
Ben-Zeev, A, et al., "Protein synthesis requires cell-surface contact while nuclear events respond to cell shape in anchorage-dependent fibroblasts", Cell, vol. 21., (1980), 365-372.
Berlet, G.C., et al., "Treatment of Unstable Osteochondritis Dissecans Lesions of the Knee Using Autogenous Osteochondral Grafts (Mosaicplasty)", Arthroscopy 15-3, (1999), 312-316.
Binette, F, et al., "Tenninally Redifferentiated Human Articular Chondrocytes Express Hyaline Cartilage Markers without Hypertrophy", Genzyrne Tissue Repair, 43rd Annual Meeting, Orthopaedic Research Society, USA, (1997), 520 pgs.
Black, J., "Biological Performance of Tantalum", Clinical Materials, vol. 16., (1994), 167-173.
Bobyn, J D, et al., "Effect of pore size on the peel strength of attachment of fibrous tissue to porous-surfaced implants", J. Biomed. Mater. Res., vol. 16., (1982), 571-584.
Bobyn, J. D., et al., "Characteristics of bone ingrowth and interface mechanics of a new porous tantalum biomaterial", J. Bone Joint Surg Br., 81, (Sep. 1999), 907-914.
Bobyn, JD, et al., "Tissue response to porous tantalum acetabular cups", a canine model. J. Arthroplasty, 14, (1999), 347-54.
Bodo, G, et al., "Arthroscopic Autologous Osteochondral Mosiacplasty For The Treatment of Sybchondral Cystic Lesion in the Medical Femoral Condyle in A Horse", Acta Veterinaria Hungarica, vol. 48 Vo. 3, (2000), 343-354.
Boumediene, et al., "Modulation of rabbit articular chondrocyte (RAC) proliferation by TGF-B isoforms", Cell Prolif., vol. 28, (1995), 221-234.
Braun, A, et al., "The Use of Fibrin Adhesive in Fixation of Osteochondral Fragments", Orthopaedic Transactions, 8(2), Abstract only, Annual Meeting of the Canadian Orthopaedic Research Society, Quebec, Canada, Jun. 5-6, 1983, (1984), 215.
Breadon, G E, et al., "Autografts of Uncrushed and Crushed Bone and Cartilage", Bone and Cartilage Autografts, vol. 108, (1979), 75-80.
Brighton, et al., "Articular Cartilage Preservation and Storage", Arthritis and Rheumatism 22(10), (1979), 1093-1101.
Brighton, Carl T, et al., "In Vitro Rabbit Articular Cartilage Organ Model II. 35S Incorporation in Various Oxygen Tensions", Arthritis and Rheumatism vol. 17, No. 3, (May 1974), 245-252.
Brittberg, et al., "Treatment of Deep Cartilage Defects in the Knee with Autologous Chondrocyte Transplantation", N. Engl. J. Med.: 331(14), (Oct. 6, 1994), 889-895.
Brittberg, Mats, "Autologous Chondrocyte Transplantation", Clinical Orthopaedics and Related Research vol. 367S,, (1999), 147-155.
Brodkin, H A, "Diced Cartilage for Chest Wall Defects", vol. 28, No. 1, (1954), 97-102.
Brown, B L, et al., "Transplantation of Fresh Allografts (Homografts) of Crushed and Uncrushed Cartilage and Bone: A 1-Year Analysis in Rabbits", The Laryngoscope, vol. 90, (1980), 1521-1532.
Bruns, J, et al., "Autologous Perichondrial Transplantation for the Repair of Experimentally Induced Cartilage Defects in the Sheep Knee-Two Glueing Techniques", Orthopedic Surgery Maxilofacial Surgery, Fibrin Sealing in Surgical and Nonsurgical Fields, Springer, Berlin, Heidelber, (Oct. 27, 1994), 50-60.
Bruns, J, et al., "Autologous rib perichondrial grafts in experimentally induced osteochondral lesions in the sheep-knee joint: morphological results", Virchows Archiv A Pathol Anat 421, (1992), 1-8.
Bruns, J, et al., "Long-Term Follow up Results after Gluing Osteochondral Fragments in Patients with Osteochondrosis Dissecans", Langenbecks Arch Chir, vol. 378, (1993), 160-166.
Buckwalter, J. A, "Articular Cartilage Injuries", Clinical Orthopaedics and Related Research, No. 402, (2002), 21-37.
Bujia, et al., "Synthesis of human cartilage using organotypic cell culture", ORL, vol. 55, (1993), 347-351.
Bujia, J, et al., "Culture and Cryopreservation of Chondrocytes from Human Cartilage: Relevance for Cartilage Allografting in Otolaryngology", ORL, (1992), 80-84.
Bujia, J, "Determination of the Viability of Crushed Cartilage Grafts: Clinical Implications for Wound Healing in Nasal Surgery", Ann Plast Surg, vol. 32, (1994), 261-265.
Bujia, J, et al., "Effect of Growth Factors on Cell Proliferation by Human Nasal Septal Chondrocytes Cultured in Monolayer", Acta Otolaryngol, vol. 114, Scandinavian University Press, Sweden, (1994), 539-543.
Butler, M, et al., "Nutritional aspects of the growth of animal cells in culture", Journal of Biotechnology 12, (1989), 97-110.
Butler, Michael, et al., "Adaptation of mammalian cells to non-ammoniagenic media", Cytotechnology 15, (1994), 87-94.

(56) References Cited

OTHER PUBLICATIONS

Calandruccio, et al., "Proliferation, Regeneration, and Repair of Articular Cartilage of Immature Animals", J. Bone Joint Surg, vol. 44-A, No. 3, (1962), 431-455.
Caruso, Enzo M, et al., "Repopulation of Laser-Perforated Chondroepiphyseal Matrix with Xenogenic Chondrocytes: An Experimental Model", Journal of Orthopaedic Research, vol. 14, (1996), 102-107.
Chang, et al., "Cartilage-Derived Morphogenetic Proteins", J. Biol. Chem., 269, (1994), 28227-28234.
Chawla, K, et al., "Short-term retention of labeled chondrocyte subpopulations in stratified tissue-engineered cartilaginous constructs implanted in vivo in mini-pigs", Tissue Engineering vol. 13, No. 7, (2007), 1525-1538.
Chen, Frank S, et al., "Repair of articular cartilage defects: Part II treatment options", The American Journal of Orthopedics 28(2), (1999), 88-96.
Cheng, Nai-Chen, et al., "Chondrogenic Differentiation of Adipose-Derived Adult Stem Cells by a Porous Scaffold Derived from Native Articular Cartilage Extracellular Matrix", Tissue Engineering: Part A, vol. 15 No. 2, (2009), 231-244.
Cherry, R S, et al., "Hydrodynamic effects on cells in agitated tissue culture reactors", Bioprocess Engineering, vol. I, Springer-Verlag, USA, (1986), 29-41.
Cherry, Robert S, et al., "Physical Mechanisms of Cell Damage in Microcarrier Cell Culture Bioreactors", Biotechnology and Bioengineering, vol. 32, John Wiley & Sons, Inc., USA, (1988), 1001-1014.
Cherry, Robert S, et al., "Understanding and Controlling Fluid-Mechanical Injury of Animal Cells in Bioreactors", Animal Cell Biotechnology, vol. 4, Academic Press Limited, USA, (1990), 71-121.
Cherubino, P, et al., "Autologous chondrocyte implantation using a bilayer collagen membrane: A preliminary report", Journal of Orthopaedic Surgery vol. II, No. 1, Italy, (2003), 10-15.
Chesterman, P J, et al., "Homotransplantation of Articular Cartilage and Isolated Chondrocytes, An Experimental Study in Rabbits", JBJS, (1968), 184-197.
Chesterman, P. J, et al., "Cartilage as a Homograft", The Journal of Bone and Joint Surgery. Proceedings and reports of councils and associations, (1968), 878.
Cheung, H, et al., "Growth of osteoblasts on porous calcium phosphate ceramic: an in vitro model for biocompatibility study", Biomaterials vol. 10, Issue 1, (Jan. 1989), 63-67.
Choi, Ye Chin, et al., "Effect of Platelet Lysate on Growth and Sulfated Glycosaminoglycan Synthesis in Articular Chondrocyte Cultures", Arthritis and Rheumatism, vol. 22, No. 2, USA, (1980), 220-224.
Christel, P, et al., "Osteochondral Grafting using the Mosaicplasty Technique", [Online] Retrived from the internet Dec. 16, 2008: <www.maitrise-orthop.com/corpusmaitri/orthopaedic/mo76_mosaicplasty/index.shtm>, 20 pgs.
Christie, A, et al., "Glutamine-based dipeptides are unilized in mammalian cell culture by extracellular hydrolysis catalyzed by a specific peptidase", Journal of Biotechnology 37, (1994), 277-290.
Convery, F.R., et al., "The Repair of Large Osteochondral Defects", An Experimental Study in Horses, Clin. Orthrop. 82., (1972), 253-262.
Cooke, M. E, et al., "Manuscript-Structured Three-dimensional co-culture of mesenchymal stem cells with chondrocyts promotes chondrogenic differentiation without hypertrophy", Osteoarthritis & Cartilage, 19(10), (Oct. 2011), 1-19.
Coster, D., et al., "Diced cartilage grafts to correct enophthalmos", British Journal of Ophthamology, vol. 64, (1980), 135-136.
Coutts, Richard D, et al., "Section III Basic Science and Pathology Rib Periochondrial Autografts in Full-Thickness Articular Cartilage Defects in Rabbits", Clinic Orthopaedics and Related Research, No. 275, USA, (1989), 263-273.
Craigmyle, M B, "Studies of cartilage autografts and homografts in the rabbit", British Journal of Plastic Surgery 8, (1955), 93-100.

Craigmyle, M.B.L., "An Autoradiographic and Histochemical Study of Long-term Cartilage Grafts in the Rabbit", J of Anatomy, vol. 92, part 3, (1954), 467-473.
Craigmyle, M.B.L., "Cellular Survival in Long-Term Cartilage Grafts in the Rabbit", Transplantation Bulletin, vol. 5, No. 1, (1958), 123.
Croughan, Matthew Shane, et al., "Hydrodynamic Effects on Animal Cells Grown in Microcarrier Cultures", Biotechnology and Bioengineering, vol. XXIX, John Wiley & Sons, Inc., USA, (1987), 130-141.
Davis, John Staige, "Some of the Problems of Plastic Surgery", Read before the Philadelphia Academy of Surgery, (Mar. 5, 1917), 88-94.
Davis, W. Brian, et al., "Absorption of Autogenous Cartilage Grafts in Man", British Journal of Plastic Surgery, vol. 9, (1956), 177-185.
De Kleine, "A Simplified Method for Handling of Diced Cartilage", Plast Reconstr. Surg., vol. 3, (1948), 95-102.
Decher, H, "Reduction of Radical Cavities by Means of Homologous Cartilage Chips", Larying. Rhino. Otol., vol. 64, (1985), 423-426.
Degroot, Jeroen, et al., "Age Related Decrease in Proteoglycan Synthesis of Human Articular Chondrocytes", The Role of Nonenzymatic Glycation Arthritis and Rheumatism, vol. 42, No. 5 (May 1999), 1003-1009.
Delbruck, Axel, et al., "In-Vitro Culture of Human Chondrocytes from Adult Subjects", Connective Tissue Research, Gordon and Breach, Science Publishers, Inc., USA, (1986), 155-172.
Dewey, Jr, C F, et al., "The Dynamic Response of Vascular Endothelial Cells to Fluid Shear Stress", Journal of Biomechnical Engineering, vol. 103, USA, (1981), 177-185.
Didier, R, et al., "Production de cartilage et d'os, au sein de greffes vivantes et mortes, chez le lapin", Comptes Rendus Hebdomadaires, (1928), 5 pp.
Didier, R, et al., "The production of cartilage and bone grafts in living and dead rabbits", Compt. rend. Soc de bioi, vol. 98, (1928), 443-445.
Dogterom, A A, et al., "Matrix depletion of young and old human articular cartilage by cultured autologous synovium fragments; a chondrocyte-independent effect", Rheumatology International, vol. 5, Springer-Verlag, UK, (1985), 169-173.
Dowthwaite, Gary P, et al., "The surface of articular cartilage contains a progenitor cell population", Journal of Cell Science vol. 117, The Company of Biologists, 2004 UK, (2004), 889-897.
Drobnic, M. MD, et al., "Comparison of four techniques for the fixation of a collagen scaffold in the human cadaveric knee", Osteoarthritis and Cartilage, vol. 14 Elsevier Ltd., UK, (2006), 337-344.
Dupertius, S M, "Growth of Young Human Autogenous Cartilage Grafts", Plast Reconstr Surg, vol. 5, No. 6, (1946), 486-93.
Dupertuis, S., "Actual Growth of Young Cartilage Transplants in Rabbits", Archives of Surgery, vol. 43, (1941), 32-63.
Eberlin, J L, et al., "Osteocartilagenous Reconstruction, Plastic Surgery Nerve Repair Burns, Fibrin Sealing in Surgical and Non-surgical Fields", vol. 3, Springer-Verlag, Berlin, Heidelberg, (1995), 20-24.
Egkher, E, et al., "Indications and Limits of Fibrin Adhesive Applied to Traumatological Patients", Traumatology and Orthopaedics, vol. 7, Springer-Verlag, Berlin Heidelberg, (1986), 144-151.
Elima, Kati, et al., "Expression of mRNAs for collagens and other matrix components in dedifferentiating and redifferentiating human chondrocytes in culture", FEBS Letters, vol. 258 No. 2, Elsevier Science Publishers B.V. (Biomedical Division), UK, (1989), 195-198.
Erikson, U, et al., "A Roentgenological Method for the Determination of Renal Blood Flow", English Abstract Only. A preliminary report, Acta Soc Med Ups, vol. 70, No. 3, (1965), 213-6.
Erol, et al., "The Turkish Delight: A Pliable Graft for Rhinoplasty,", Plas!. Reconstr. Surg., vol. 105, (2000), 2229-2241.
Evans, C H, et al., "Experimental Arthritis Induced by Intraarticular Injection of Allogenic Cartilageinous Particles into Rabbit Knees", Arthritis and Rheumatism, vol. 27, No. 2, (1984), 200-207.

(56) References Cited

OTHER PUBLICATIONS

Evans, Robin C, et al., "Solute diffusivity correlates with mechanical properties and matrix density of compressed articular cartilage", Archives of Biochemistry and Biophysics, vol. 442, Elsevier, UK, (2005), 1-10.
Farmer, S R, et al., "Altered Translatability of Messenger RNA from Suspended Anchorage-Dependent Fibroblasts", Reversal upon Cell Attachment to a Surface, Cell, vol. 15., (1978), 627-637.
Farrior, R T, "Implant Materials in Restoration of Facial Contour", Laryngoscope, vol. 76, No. 5, (1966), 934-54.
Feder, J, "Tissue Engineering in Musculoskeletal Clinical Practice: The Promise of Chondral Repair Using Neocartilage", Am. Acad. Orthop. Surg., Chapter 22., (2004), 219-226.
Feder, Joseph, et al., "The Large-Scale Cultivation of Mammalian Cells", Scientific American, Inc USA, (1983), 36-43.
Feder, Joseph, et al., "The Promise of Chondral Repair Using Neocartilage", Chapter 22, (2004), 219-226.
Feldman, M D, et al., "Compatibility of Autologous Fibrin Adhesive With Implant Materials", Arch Otolaryngol Head Neck Surg, vol. 114, (1988), 182-185.
Folkman, J, et al., "Role of cell shape in growth control", Nature, vol. 273., (1978), 345-349.
Fontana, A., et al., "Cartilage Chips Synthesized with Fibrin Glue in Rhinoplasty", Aesthy. Plast. Surg.15, (1991), 237-240.
Frangos, John, et al., "Flow Effects on Prostacyclin Production by Cultured Human Endothelial Cells", Science, vol. 227, Texas, USA, (1985), 1477-1479.
Freed, L E, et al., "Neocartilage formation in virtro and invivo using cells cultured on synthetic biodegradable polymers", J. Biomed. Mater. Res. vol. 27 (1), (1993), 11-23.
Freed, L. E, et al., "Cartilage Tissue Engineering Based on Cell-Polymer Constructs", Tissue Engineering of Cartilage, CRC Press, Inc., USA, (1995), 1788-1806.
Freed, L. E, et al., "Composition of Cell-Polymer Cartilage Implants", Biotechnology and Bioengineering, vol. 43, John Wiley & Sons, Inc., USA, (1994), 605-614.
Freed, L. E, et al., "Cultivation of Cell-Polymer Cartilage Implants in Bioreactors", Journal of Cellular Biochemistry, vol. 51, Wiley-Liss, Inc., USA, (1993), 257-264.
Freed, L. E, et al., "Cultivation of Cell-Polymer Tissue Constructs in Simulated Microgravity", Biotechnology and Bioengineering, vol. 46, John Wiley & Sons, Inc., USA, (1995), 306-313.
Freed, Lisa E, et al., "Tissue engineering of cartilage in space", Proc. Natl. Acad. Sci., vol. 94, The National Academy of Sciences, USA, (1997), 13885-13890.
Frisbie, David D, et al., "In Vivo Evaluation of Autologous Cartilage Fragment-Loaded Scaffolds Implanted Into Equine Articular Defects and Compared With Autologous Chondrocyte Implantation", The American Journal of Sports Medicine 37, (Nov. 24, 2009), 71S-80S.
Fry, Donald, "Acute Vascular Endothelial Changes Associated with Increased Blood Velocity Gradients,", Journal of the American Heart Association, vol. XXII, American Heart Association, USA, (1968), 165-197.
Fub, M, et al., "Characteristics of human chondrocytes, osteoblasts and fibroblasts seeded onto a type I/II collagen sponge under different culture conditions", Annals of Anatomy, vol. 182, Urban & Fischer Verlag, Germany, (2000), 303-310.
Furukawa, T, et al., "Biochemical Studies on Repair Cartilage Resurfacing Experimental Defects in the Rabbitt Knee", J Bone Joint Surg Am, vol. 62, No. 1, (1980), 79-89.
Galera, et al., "Effect of transforming growth factor-B1 (TGF-B1) on matrix synthesis by monolayer cultures of rabbit chondrocytes during the dedifferentiating process", Experimental Cell Research, vol. 200, (1992), 379-392.
Gaudernak, T, et al., "Clinical Experiences Using Fibrin Sealant in the Treatment of Osteochondral Fractures, Fibrin Sealant in Operative Medicine", Traumatology and Orthopaedics, vol. 7, Springer-Verlag, Berlin, Heidelberg, (1986), 91-102.

Gelse, K, et al., "Paracrine Effect of Transplanted Rob Chondrocyte Spheroids Supports Formation of Secondary Cartilage Repair Tissue", J Ortho Res, vol. 27, (2009), 1216-1225.
Gerngross, H, et al., "Experimental Studies on the Influence of Fibrin Adhesive, Factor XIII, and Calcitonin on the Incorporation and Remodeling of Autologous Bone Grafts", Arch Orthop Trauma Surg, vol. 106, (1986), 23, 31.
Gersdorff, M.C.H., et al., ""How I Do It"—Otology and Neurotology. A Specific Issue and Its Solution. A New Procedure for Bone Reconstruction in OTO-Microsurgery: A Mixture of Bone Dust and Fibrinogen Adhesive", Laryngoscope, vol. 95, (1985), 1278-1280.
Ghadially, J A, et al., "Evidence of Cartilage Flow in Deep Defects in Articular Cartilage", Virchows Arch B Cell Path, vol. 18, (1975), 193-204.
Ghadially, J A, et al., "Long-Term Results of Deep Defects in Articular Cartilage", Virchows Arch B. Cell Path, vol. 25, (1977), 125-136.
Ghazavi, M. T, et al., "Fresh Osteochondral Allografts for Post-Traumatic Osteochondral Defects of the Knee", J. Bone Joint Surg., 79-B, (1997), 1008-1013.
Gibble, et al., "Fibrin glue: the perfect operative sealant", Transfusion, 1990, vol. 30, No. 8., 741-747.
Gibson, Thomas, et al., "The long-term survival of cartilage homografts in man", British Journal of Plastic Surgery 11, (1958), 177-187.
Gille, J, et al., "Migration pattern, morphology and viability of cells suspended in or sealed with fibrin glue: A histomorphologic study", Tissue and Cell, Vo. 37, Elsevier, UK, (2005), 339-348.
Girotto, Davide, et al., "Tissue-specific gene expression in chondrocytes grown on three-dimensional hyaluronic acid scaffolds", Biomaterials, vol. 24, Elsevier, UK, (2003), 3265-3275.
Glacken, Michael W, "Catabolic Control of Mammalian Cell Culture", Biotechnology vol. 6, (Sep. 1998), 1041-1050.
Gooch, K J, et al., "Effects of Mixing Intensity on Tissue-Engineered Cartilage", Biotechnology and Bioengineering, vol. 72, No. 4, John Wiley & Sons, Inc., USA, (2001), 402-407.
Gooding, C R, et al., "A Prospective, Randomised Study Compairing Two Techniques of Autologous Chondrocyte Implantation for Osteochondral Defects in the Knee: Periosteum Covered Versus Type I/III Collagen Covered", Abstract Only, Knee, vol. 13, No. 3, (2006), 203-10.
Greco, F, et al., "Experimental Investigation into Reparative Osteogenesis With Fibrin Adhesive", Arch Orthop Trauma Surg, vol. 107, (1988), 99-104.
Gu, Joseph D, et al., "True Density of Normal and Enzymatically Treated Bovine Articular Cartilage", Orthopaedic Research Laboratory, Columbia University, (1999), 642.
Guilak, F, et al., "Functional tissue engineering: the role of biomechanics in articular cartilage repair", Clin Orthop Relat Res, vol. 391S., (2001), 295-305.
Haart, et al., "Optimization of chondrocyte expansion in culture", Acta Orthop Scand, vol. 70, No. 1, (1999), 55-61.
Hacking, S A, et al., "Fibrous tissue ingrowth and attachment to porous tantalum", J. Biomed. Mater. Res., vol. 52, No. 4., (2000), 631-638.
Hammarqvist, Folke, et al., "Alanyl-glutamine Counteracts the Depletion of Free Glutamine and the Postoperative Decline in Protein Synthesis in Skeletal Muscle", Ann. Surg, (Nov. 1990), 637-644.
Hamra, S T, "Crushed Cartilage Grafts over Alar Dome Reduction in Open Rhinoplasty", Plast Reconstr Surg, vol. 92, No. 2, (1993), 352-6.
Han, et al., "Scaffold-free Grafts for Articular Cartilage Defects", Clin Orthop Relat Res. vol. 466, (2008), 1912-1920.
Hangody, L, et al., "Autologous Osteochondral Mosaicplasty for the Treatment of Full-Thickness Defects of Weight-Bearing Joints: Ten Years of Experimental and Clinical Experience", JBJS, vol. 85, (2003), 25-32.
Hangody, L, et al., "Mosaicplasty for the Treatment of Articular Defects of the Knee and Ankle", Clin Orthopaedics and Rel Res, No. 391S, (2001), S328-S336.

(56) References Cited

OTHER PUBLICATIONS

Hangody, Laszlo, et al., "Autogenous Osteochondral Graft Technique for Replacing Knee Cartilage Defects in Dogs", Autogenous Osteochondral Mosaicplasty—Orthopaedics International Ed., vol. 5, No. 3, (1997), 175-181.
Harbin, M, et al., "Autogenous Free Cartilage Transplanted into Joints", Archives of Surgery, vol. 20, No. 6, (1930), 885-896.
Harrison, et al., "Osteogenin promotes reexpression of cartilage phenotype by dedifferentiated articular chondrocytes in serum-free medium", Experimental Cell Research, vol. 192, (1991), 340-345.
Harrison, et al., "Transforming growth factor-beta: Its effect on phenotype reexpression by dedifferentiated chondrocytes in the presence and absence of osteogenin", In Vitro Cell Dev. Biol., vol. 28A, (1992), 445-448.
Hassell, T, et al., "Growth Inhibition in Animal Cell Culture: The Effect of Lactate and Ammonia", Applied Biochemistry and Biotechnology, vol. 30, (1991), 29-41.
He, Q, et al., "Repair of Flexor Tendon Defects of Rabbit With Tissue Engineering Method", Chinese J. of Traumatology, 5(4), (2002), 200-208.
Helidonis, E., et al., "Laser Shaping of Composite Cartilage Grafts", Am J Otolaryngology, vol. 14, No. 6, (1993), 410-412.
Hendrickson, Dean A, "Chondrocyte-Fibrin Matrix Transplants for Resurfacing Extensive Articular Cartilage Defects", Journal of Orthopaedic Research vol. 12 The Journal of Bone and Joint Surgery, Inc., (1994), 485-497.
Hiraki, et al., "Effect of transforming growth factor B on cell proliferation and glycosaminoglycen synthesis by rabbit growth-plate chondrocytes in culture", Biochimica et Biophysica Acta, vol. 969, (1988), 91-99.
Hollander, Anthony P, et al., "Maturation of Tissue Engineered Cartilage Implanted in Injured and Osteoarthritic Human Knees,", Tissue Engineering, vol. 12, No. 7, Mary Ann Leibert, Inc., UK, (2006), 1787-1798.
Hollinger, Jeffrey O, et al., "Poly(alpha-hydroxy acids): carriers for bon morphogenetic proteins", Biomaterial, vol. 17, (1996), 187-194.
Homminga, G N, "Repair of Chondral Lesions of the Knee with e Perichondrial Graft, Fibrin Sealant in Operative Medicine", Orthopedic Surgery Maxillofacial Surgery, vol. 4, Springer-Verlag, Berlin Heidelberg, (1986), 61-69.
Homminga, G., et al., "Perichondral grafting for cartilage lesions of the knee", J. Bone Joint Surg. (Br.) 72-B, (1990), 1003-1007.
Homminga, George N, et al., "Chondrocyte Behavior in fibrin glue in vitro", Acta Orthop Scand, vol. 64 No. 4, (1993), 441-445.
Hoover, N W, et al., "Skin Arthroplasty of the Hip, An Experimental Study in Dogs", JBJS, vol. 43-A, No. 8, (1961), 1155-1166.
Horas, U., et al., "Autologous Chondrocyte Implantation and Osteochondral Cylinder Transplantation in Cartilage Repair of the Knee Joint: A Prospective", Comparative Trial, J. Bone Joint Surg. Am. 85A-2, (2003), 185-192.
Horton, et al., "Transforming growth factor-beta and fibroblast growth factor act synergistically to inhibit collagen II synthesis through a mechanism involving regulatory DNA sequences", Journal of Cellular Physiology, vol. 141, (1989), 8-15.
Horton, W., et al., "Characterization of a Type II Collagen Gene (COL2A1) Mutation Identified in a Cultured Chondrocytes from Human Hypochondrogenesis", PNAS, V. 89, (1992), 4583-4587.
Howard, R. D, "Long-term fate and effects of exercise on sternal cartilage autografts used for repair of large osteochondral defects in horses", Am Journal Vet Res, vol. 55 No. 8, (Aug. 1994), 1158-1167.
Hu, Wei-Shou, "Bioreactors for Animal Cell Cultivation", Recent Advances in Biotechnology, Kluwer Academic Publishers, Netherlands, (1992), 243-261.
Huang, et al., "Tissue Engineering", vol. 8, No. 3, (2002), 469-481.
Hunter, W, VI, "Of the Structure and Difeafes of Articulating Cartilages", Academiae Grypeswaldensis Bibliotheca, vol. 1, (1775), 514-521.

Hunziker, E. B, "Articular cartilage repair: basic science and clinical progress—a review of the current status and prospects", Osteoarthritis and Cartilage 10(6), (2001), 432-463.
Hunziker, E.B., et al., "Quantitative structural organization of normal adult human articular cartilage", Osteoarthritis and Cartilage 10, (2002), 564-572.
Hurtig, M B, et al., "Effects of Lesion Size and Location on Equine Articular Cartilage Repair", Can J Vet Res, vol. 52, (1988), 137-146.
Hurtig, M. B, "Use of autogenous cartilage particles to create a model of naturally occurring degenerative joint disease in the horse", Equine Orthop., No. 6, (1988), 19-22.
Hutchinson, John, "Observations on Bone Transplants in the Anterior Chamber of the Eye", Glasgow Medical Journal, (1949), 357-363.
Imbert, Leon, et al., "Recherches sur les greffes cartilagineuses hetero-plastiques", Revue de Chirurgie, Paraissant tous les mois, (1916), 20 pp.
Imhoff, A B, et al., "Autologous Osteochondral Transplantation on Various Joints", English Abstract Only, Orthopade, vol. 28, No. 1, (1999), 33-44.
Ishida, T, "The Use of a Fibrin Adhesive for a Cartilage Graft Basic and Clinical Studies", English Abstract Only, Japanese J of Plastic and Reconstructive Surgery, vol. 33, No. 1, (1990), 215-230.
Ishizaki, Y., et al., "Autocrine Signals Enable Chondrocytes to Survive in Culture", J. Cell. Biol., 126(4), (1994), 1069-1077.
Ito, Y, et al., "Localization of chondrocyte precursors in periosteum", Osteoarthritis and Cartilage, vol. 9, (2001), 251-223.
Ittner, G, et al., "Treatment of Flake Fracture of the Talus", Z Orthop Ihre Grenzgeb, vol. 127, No. 2, English Abstract Only, (1989), 183-6.
Iwasa, J, et al., "Clinical application of scaffolds for cartilage tissue engineering", Surg Sports Traumalol Arthorsc vol. 13, No. 4, (2008), 561-577.
Jakob, et al., "Autologous Osteochondral Grafting in the Knee: Indication, Results and Reflections", Clinical Orthopaedics and Related Research, No. 401, (2002), 170-184.
Jeffries, David J, et al., "Cartilage Regeneration Following Septal Surgery in Young Rabbits", The Journal of Laryngology and Otology vol. 98, (Jun. 1984), 577-583.
Jin, C, et al., "Human Amniotic Membrane as a Delivery Matrix for Articular Cartilage Repair", Tissue Engineering, 13(4), (2007), 693-703.
Johnson, L., "Arthroscopic Abrasion Arthroplasty Historical and Pathologic Perspective: Present Status", Arthroscopy 2-1, (1986), 54-69.
Jones, C W, et al., "Matrix-induced autologous chondrocyte implantation in sheep: objective assessments including confocal arthroscopy", J. Orthopaedic Research vol. 26, (2008), 292-303.
Jurgensen, K, et al., "A New Biological Glue for Cartilage-Cartilage Interfaces: Tissue Transglutaminase", JBJS (Am), 1997, vol. 79., (1997), 185-193.
Kallio, K E, "Arthroplastia Cutanea, Discussion by T. Heirtom", ACTA Orthopaedica Scandinavica, vol. 26, (1957), 327-328.
Kandel, et al., "Fetal bovine serum inhibits chondrocyte collagenase production: interleukin 1 reverses this effect", Biochim. Biophys. Acta.: 1053(2-3), (1990), 130-134.
Kanzaki, J, et al., "Use of Fibrin Glue in Intracranial Procedures Following Acoustic Nouroma Surgery: Application in Facial Nerve Reconstruction and Prevention of Cerebrospinal Fluid Rhinorrhea, Fibrin Sealing in Surgical and Nonsurgical Fields", Neurosurgery Ophthalmic Surgery ENT, vol. 5, Springer-Verlag, Berlin, Heidelberg, (1994), 162-168.
Kaplonyi, G., et al., "The use of fibrin adhesive in the repair of chondral and osteochondral injuries", Injury 19, (1988), 267-272.
Kato, Y, et al., "Sulfated Proteoglycan Synthesis by Confluent Cultures of Rabbit Costal Chondrocytes Grown in the Presence of Fibroblast Growth Factor", J. Cell Biology, vol. 100., (1985), 477-485.
Kavalkovich, Karl W, et al., "Chondrogenic Differentiation of Human Mesenchymal Stem Cells Within an Alginate Layer Culture System", In Vitro Cell. Dev. Biol.-Animal, vol. 38, Society for In Vitro Biology, USA, (2002), 457-466.

(56) References Cited

OTHER PUBLICATIONS

Kawamura, et al., "Human Fibrin Is a Physiologic Delivery System for Bone Morphogenetic Protein", Clinical Orthopaedics and Related Research, (Oct. 1988), 302-310.
Keller, J, et al., "Fixation of Osteochondral Fractures", Acta Orthop Scand, vol. 56, (1985), 323-326.
Kettunen, K O, "Skin Arthroplasty in the Light of Animal Experiments With Special Reference to Functional Metalasia of Connective Tissue", Acta Ortho Scand, Suppl XXIX, (1958), 9-69.
Kim, et al., "OsteoArthritis and Cartilage", vol. 11, (2003), 653-664.
Kim, Myung Ku, et al., "Autologous chondrocyte implantation in the knee using fibrin", Knee Surg Sports Traumatol Arthrosc vol. 18, (2010), 528-534.
Kimura, Tomoatsu, et al., "Chondrocytes Embedded in CoHagen Gels Maintain Cartilage Phenotype During Long-term Cultures", ?Clinical Orthopaedics and related Research, vol. 186, Japan, (1984), 231-239.
Kirilak, Yaow Anuj, et al., "Fibrin Sealant Promotes Migration and Proliferation of Human Articular Chondrocytes: Possible Involvement of Thrombin and Protease-activated receptors", International Journal of Molecular Medicine vol. 17, (2006), 551-558.
Klagsbrun, et al., "Purification of a cartilage-derived growth factor", The Journal of Biological Chemistry, vol. 255, No. 22, (1980), 10859-10866.
Klagsbrun, et al., "The stimulation of DNA synthesis and cell division in chondrocytes and 3T3 cells by a growth factor isolated from cartilage", Exp Cell Res, vol. 105, (1977), 99-108.
Klein, T J, et al., "Tailoring secretion of proteoglycan 4 (PRG4) in tissue-engineered cartilage", Tissue Engineering, vol. 12, No. 6., (2006), 1429-1439.
Klein, T J, et al., "Tissue engineering of stratified articular cartilage from chondrocyte subpopulations", OsteoArthritis and Cartilage vol. 11, (2003), 595-602.
Knutsen, G., et al., "Autologous Chondrocyte Implantation Compared with Microfracture in the Knee. A Randomized Trial", J. Bone Joint Surg. Am. 86A-3, (2004), 455-464.
Kon, E, et al., "Arthroscopic second generation autologous chondrocyte implantation at 48 months follow up", Osteoarthritis and Cartilage vol. 15, Suppl. B, (2007), B44-45.
Kon, E, et al., "Arthroscopic Second-generation Autologous Chondrocyte Implantation Compared with Microfracture of Chondral Lesions of the Knee", Am J. of Sports Medicine vol. 37, No. 1, (2009), 33-41.
Kon, E, et al., "Second Generation Issues in Cartilage Repair", Sports Med Arthorosc Rev., 16(4), (2008), 221-229.
Korhonen, R K, et al., "Importance of the superficial tissue layer for the indentation stiffness of articular cartilage", Medical Eng Phys, vol. 24, (2002), 99-108.
Krueger, John W, et al., "An In Vitro Study of Flow Response by Cells", Journal of Biomechanics, vol. 4, Pergamon Press, Great Britain, (1971), 31-36.
Kuettner, Klaus E, et al., "Synthesis of Cartilage Matrix by Mammalizn Chondrocytes in Vitro.I. Isolation, Culture Characteristics, and Morphology", The Journal of Cell Biology, vol. 93, The RockefeHer University Press, USA, (1982), 743-750.
Kujawa, et al., "Hyaluronic acid bonded to cell culture surfaces inhibits the program of myogenesis", Developmental Biology, vol. 113, (1986), 10-16.
Kujawa, Mary J, et al., "Hyaluronic Acid Bonded to Cell-Culture Surfaces Timulates Chondrogenesis inStage 24 Limb Mesenchyme Cell Cultures", Developmental Biology, vol. 114, Academic Press, Inc., USA, (1986), 504-518.
Kujawa, Mary J, et al., "Substrate-Bonded Hyaluronic Acid Exhibits a Size-Dependent Stimulation of Chondrogenic Differentiation of Stage 24 Limb Mesenchymal Cells in Culture", Developmental Biology, vol. 114, Academic Press, Inc., USA, (1986), 519-528.
Lane, J. M, et al., "Joint Resurfacing in the Rabbit Using an Autologous Osteochondral Graft", JBJS, vol. 59-A, No. 2, (1977), 218-222.
Langer, F, et al., "Immunogenicity of Allograft Articular Cartilage", JBJS, vol. 56-A, No. 2, (1974), 297-304.
Langer, F, et al., "The Immunogenicity of Fresh and Frozen Allogenic Bone", JBJS, vol. 57-A, No. 2, (1975), 216-220.
Lapchinsky, A G, et al., "Instrument for Shredding Cartilage in Plastic Surgeries", New Surgical Machines and Instruments and their usage, No. 4, Moscow, (1960), 209-213.
Lavrishcheva, G I, "Filling Bone Cavities with Minced Cartilage", Ortopediia Travmatologiia I Protezirovanie, vol. 1, (1955), 80.
Lee, et al., "Primary cultured chondrocytes of different origins respond differently to bFGF and TGF-B", Life Sciences, vol. 61, No. 3, (1997), 293-299.
Lee, J W, "Preplanned Correction of Enophthalmos Using Diced Cartilage Grafts", British J Plastic Surgery, vol. 53, (2000), 17-23.
Lemperg, R, et al., "Transplantation of Diced Rib Cartilage to the Hip Joint. Experimental Study on Adult Dogs", Acta Soc Med Ups, vol. 70, No. 3, (1965), 197-212.
Lennert, K H, et al., "Fibrin Adhesive in the Surgical Treatment of the Pseudoarthrosis of the Scaphoid Bone-Methods and Results", Unfallchirurgie, vol. 14, No. 3, (1988), 158-160.
Leopold, G., "Experimental Studies into the Etiology of Tumors", Archiv. F. Path. Anat., vol. LXXXV, No. 2, (1881), 283-324.
Libera, J, et al., "Cartilage Engineering, Fundamentals of Tissue Engineering and Regenerative Medicine", Chapter 18, SPringer-Verlag, Berlin Heidelberg, (2009), 233-242.
Limberg, A A, "Supporting and Contour Plastic Repair by Needle Administration of Minced Cartilage", Vestnik Khirurgii Imeni I.I. Grekova, vol. 78, No. 4, (1957), 68-73.
Limberg, A A, "The Use of Diced Cartilage by Injection with a Needle. Part 1. Clinical Investigations", Plast Reconstr Surg Translant Bull, vol. 28, (1961), 523-36.
Limberg, A A, "The Use of Diced Cartilage by Injection with a Needle. Part 2. Morphologic Changes in The Diced Human Cartilage After Auto- and Homoplasty", Plast Reconstr Surg Transplant Bull, vol. 28, (1961), 649-655.
Lin, Z, et al., "Gene Expression Profiles of Human Chondrocytes during Passaged Monolayer Cultivation", J. Orthopaedic Research, vol. 26, (2008), 1230-1237.
Liu, Lin-Shu, et al., "An osteoconductive collagen/hyaluronate matrix for bone regeneration", Biomaterials vol. 20, Elsevier, UK, (1999), 1097-1108.
Liu, X, et al., "In vivo ectopic chondrogenesis of BMSCs directed by mature chondrocytes", Biomaterials, vol. 31, (2010), 9406-9414.
Loeb, L, "Autotransplantation and Homoiotransplantation of Cartilage in the Guinea-pig", Am. J. Pathology, V. II, (1926), 111-122.
Longacre, J J, et al., "Further Observations of the Behavior of Autogeneous Split-Rib Grafts in Reconstruction of Extensive Defencts of the Cranium and Face", Plastic and Reconstructive Surgery, vol. 20 No. 4, Read at the Meeting of the American Association of Plastic Surgeons, Skytop, PA, (Oct. 1957), 281-296.
Lu, Yiling, et al., "Minced Cartilage Without Cell Culture Serves as an Effective Intraoperative Cell Source for Cartilage Repair", Journal of Orthopaedic Research, 24(6), (Jun. 2006), 1261-1270.
Lucas, Paula, et al., "Ectopic induction of cartilage and bone by water-soluble proteins from bovine bone using a collagenous delivery vehicle", Journal of Biomedical Materials Research: Applied Biomaterials, vol. 23, No. AI, (1989), 23-39.
Lucht, U, et al., "Fibrin Sealant in Bone Transplantation. No Effects on Blood Flow and Bone Formation in Dogs", Acta Orthop Scand, vol. 57, No. 1, (1986), 19-24.
Luyten, Frank P, et al., "Chapter 9: Articular Cartilage Repair: Potential Role of Growth and Differentiation Factors", Biological Regulation of the Chondrocytes, Boca Raton, Fla. : CRC Press, (1992), 227-236.
MacKay, et al., "Chondrogenic differentiation of cultured human mesenchymal stem cells from marrow", Tissue Engineering, vol. 4, No. 4, (1998), 415-430.
Mahomed, M.N., et al., "The Long-Term Success of Fresh, Small Fragment Osteochondral Alografts Used for Intraarticular Post-Traumatic Defects in the Knee Joint", Orthopedics 15, (1992), 1191-1199.

(56) References Cited

OTHER PUBLICATIONS

Mainil-Varlet, P, et al., "Articular cartilage repair using a tissue-engineered cartilage-like implant: an animal study", Osteoarthritis Cartilage Suppl. A, vol. 9, (2001), 6-15.

Malemud, C J, et al., "The effect of chondrocyte growth factor on membrane transport by articular chondrocytes in monolayer culture", Connective Tissue Research, vol. 6, (1978), 1-9.

Maletius, W, et al., "Refixation of Large Chondral Fragments on the Weight-Bearing area of the Knee Joint: A Report of Two Cases", Arthroscopy, vol. 10, No. 6, (1994), 630-3.

Mandl, E W, et al., "Multiplication of human chondrocytes with low seeding densities accelerates cell yield without losing redifferentiation capacity", Tissue Engineering, vol. 10, No. 1/2, (2004), 109-120.

Mandl, E W, et al., "Serum-free medium supplemented with high-concentration FGF2 for cell expansion culture of human ear chondrocytes promotes redifferentiation capacity", Tissue Engineering, vol. 8, No. 4, (2002), 573-582.

Mankin, H J, "Current Concepts Review, The Response of Articular Cartilage to Mechanical Injury", JBJS, vol. 64, No. 3, (1982), 460-6.

Mankin, H J, "Localization of Tritiated Thymidine in Articular Cartilage of Rabbits: II. Repair in Immature Cartilage", JBJS, V. 44, (1962), 688-698.

Mankin, H J, "Localization of Tritiated Thymidine in Articular Cartilage of Rabbits: III. Mature Articular Cartilage", JBJS, V. 45, (1963), 529-540.

Mannheim, A, "Free Autoploastic Cartilage transplantation—Uber freie autoplastische Knorpeltransplantation", Arch. F klin Chir, (1926), 668-672.

Mannhelm, A, "Free Autoplastic Cartilage Transplantation", Abstract, J Am Med Assoc, vol. 87, No. 25, (1926), 2132.

Marcacci, et al., "Articular Cartilage Engineering with Hyalograft C", Clinical Orthopaedics & Related Research, V. 435, (Jun. 2005), 96-105.

Marcacci, M, et al., "Multiple Osteochondral Arthroscopic Grafting (Mosaicplasty) for Cartilage Defects of the Knee: Prospective Study Results at 2-Year Follow-up", J. Arthroscopic & Related Surgery, vol. 21, No. 4., (2005), 462-470.

Marcacci, M, et al., "Use of Autologous Grafts for Reconstruction of Osteochondral Defects of the Knee", Orthopedics, vol. 22, No. 6, (1999), 959-600.

Marchac, D, et al., "Face Lifts and Sprayed Fibrin Glue: An Outcome Analysis of 200 patients", Br J Plast Surg, vol. 47, No. 5, (1994), 306-9.

Marchac, D, et al., "Fibrin Glue Fixation in Forehead Endoscopy: Evaluation of our Experience with 206 Cases", Plast Reconstr Surg, vol. 100, No. 3, (1997), 713-4.

Marlovits, S, et al., "Changes in the ratio of type-I and type-II collagen expression during monolayer culture of human chondrocytes", JBJS, vol. 86-B, (2004), 286-95.

Marlovits, Stefan, et al., "Early postoperative adherence of matrix-induced autologous chondrocyte implantation for the treatment of full-thickness cartilage defects of the femoral condyle", Knee Surg Sports Traumatol Arthorosc, vol. 13, Springer-Verlag, Austria, (2005), 451-457.

Marmotti, A, et al., "One-step osteochondral repair with cartilage fragments in a composite scaffold", Knee Surg Sports Traumatol Arthrosc, (Feb. 21, 2012), 12 pp.

Marvin, H M, "The Value of the Xanthine Diuretics in Congestive Heart Failure", The Journal of the American Medical Association, vol. 87, No. 25, Abstract only, (Dec. 18, 1926), 2131-2132.

Mathiowitz, Edith, et al., "Biologically erodable microspheres as potential oral drug delivery systems", Nature, vol. 386, (Mar. 1997), 410-414.

Matras, H, "Fibrin Seal: The State of the Art", J Oral Maxilofac Surg, vol. 43, (1985), 605-611.

Matsusue, Y, et al., "Biodegradable Pin Fixation of Osteochondral Fragments of the Knee", Clin Ortho Rel Res, No. 322, (1996), 166-173.

McCormick, F., "Minced Articular Cartilage—Basic Science, Surgical Technique, and Clinical Application", Sports Med. Arthrosc. Rev., vol. 16, No. 4, (Dec. 2008), 217-220.

McDermott, et al., "Fresh small-fragment osteochondral allografts", Clinical Orthopaedics and Related Research, No. 197, (1985), 96-102.

McIlwraith, C W, et al., "In-Vivo Evaluation of a One-Step Autologous Cartilage Resurfacing Technique (CAIS)—Comparison of Three Different Scaffolds", 6th Symposium of the International Cartilage Repair Society, (Jan. 2006), p. 3-6.

McKibbin, B, "Immature Joint Cartilage and the Homograft Reaction", JBJS, V. 53-B, No. 1, (1971), 123-135.

McKibbin, B, et al., "The Dual Nature of Epiphysical Cartilage", Department of Orthopaedics, vol. 49B, No. 2, (May 1967), 351-361.

McNickle, Allison G, et al., "Overview of Existing Cartilage Repair Technology", Sports Med Arthorosc Rev., vol. 16, No. 4, Lippincott Williams & Wilkins, USA, (2008), 196-201.

McQueen, Anne, et al., "Flow Effects on the Viability and Lysis of Suspended Mammalian Cells", Biotechnology Letters, vol. 9, No. 12, California Institute of Technology, USA, (1987), 831-836.

Meachim, G., et al., "Repair of the joint surface from subarticular tissue in the rabbit knee", J. Anat. 109-2, (1971), 317-327.

Medawar, P. B, "Immunity to Homologous Grafted Skin. III. The Fate of Skin Homografts Transplanted to the Brain, to Subcutaneous Tissue, and to the Anterior Chamber of the Eye", Department of Zoology Immunity to Homologous Grafted Skin, (Dec. 8, 1947), 58-69.

Merchuk, Jose Celman, "Shear Effects on Suspended Cells", Advances in Biochemical Engineering Biotechnology, vol. 44, Springer-Verlag Berlin Heidelberg, (1988).

Merchuk, Jose C, et al., "Why use air-lift bioreactors?", Tibtech, vol. 8, Elsevier Science Publishers Ltd., UK, (1990), 66-71.

Meyers, M H, et al., "A Fibrin Adhesive Seal for the Repair of Osteochondral Fracture Fragments", Clin Ortho Rel Res, No. 182, (1984), 258-263.

Mienaltowski, M J, et al., "Differential gene expression associated with postnatal equine articular cartilage maturation", BMC Musculoskeletal Disorders, vol. 9., (2008), 149-162.

Minamoto, Yoshiki, et al., "Development of a serum-free and heat-sterilizable medium and continuous high-density cell culture", Cytotechnology, vol. 5, (1991), S35-S51.

Minas, T, et al., "Current Concepts in the Treatment of Articular Cartilage Defects", Orthopedics, vol. 20., (1997), 525-538.

Mitchell, Nelson, et al., "The Resurfacing of Adult Rabbit Articular Cartilage by Multiple Perforations through the Subchondral Bone", J. Bone Joint Surg. 58A-2, (1976), 230-233.

Mithofer, K, et al., "Functional Outcome of Knee Articular Cartilage Repair in Adolescent Athletes", Am J Sports Med, vol. 33, No. 8, (2005), 1147-53.

Miura, Y, et al., "Brief Exposure to High-Dose Transforming Growth Factor-Beta 1 Enhances Periosteal Chondrogenesis in Vitro: a Premilinary Report", JBJS, vol. 84-A, No. 5, (2002), 793-9.

Morales, T I, "Review Chondrocyte moves: clever strategies?", Osteoarthritis and Cartilage vol. 15 No. 8 International Cartilage Repair Society, (2007), 861-871.

Mow, V C, et al., "Experimental Studies on Repair of Large Osteochondral Defects at a High Weight Bearing Area of the Knee Joint: A Tissue Engineering Study", Transactions of the ASME, Journal of Biomechanical Engineering, vol. 113, USA, (1991), 198-207.

Munirah, S, et al., "Articular Cartilage Restoration in load-bearing osteochondral defects by implantation of autologous chondrocyte-fibrin constructs", The Journal of Bone and Joint Surgery, vol. 89-B, No. 8, An Experimental Study in Sheep, (Aug. 2007), 1099-1109.

Murray, M M, et al., "The Migration of Cells From the Ruptured Human Anterior Cruciate Ligament Into Collagen-Glycosaminoglycan Regeneration Templates in Vitro", Biomaterials, vol. 22, (2001), 2393-2402.

Nageotte, J, "The Organization of Matter in its Connections with Life. Studies of General Anatomy and Experimental Morphology on the Connective Tissue and the Nerve", L'Organisation De La Matiere, (1922), 95-98.

(56) References Cited

OTHER PUBLICATIONS

Namba, Robert S, "Spontaneous Repair of Superficial Defects in Articular Cartilage in a Fetal Lamb Model", Journal of Bone and Joint Surgery, Inc., (1998), 4-10.
Nehrer, S, et al., "Three-year Clinical Outcome after chondrocyte transplantation using a hyaluronan matrix for cartilage repair", European Journal of Radiology vol. 57, (2006), 3-8.
Nehrer, Stefan, et al., "Treatment of Articular Cartilage Defects", Investigative Radiology, vol. 35, No. 10, (2000), 639-646.
Newland, M, et al., "Hybridoma growth limitations: The roles of energy metabolism and ammonia production", Cytotechnology, vol. 3, (1990), 215-229.
Niekisch, V R, "Possible Methods of Using Fibrin-Glue Protection in Maxillo Facial Surgery", English Summary Only. Zahn Mund Kieferheilkd Zentralbl, vol. 68, No. 6, (1980), 555-61.
Nixon, Alan, et al., "Isolation, propagation, and cryopreservation of equine articular chondrocytes", American Journal of Veterinary Research, 53(12), (1992), 2364-2370.
Nixon, Alan J, et al., "New Horizons in Articular Cartilage", Proceedings of the 47th Annual American Association of Equine Practitioners Convention, V. 47, (2001), 217-226.
Nixon, Alan J, et al., "Temporal matrix synthesis and histologic features of a chondrocyte-laden porous collagen cartilage analogue", American Journal of Veterinary Research, vol. 54, No. 2, USA, (1993), 349-356.
Obradovic, B, et al., "Integration of Engineered Cartilage", Journal of Orthop Res, vol. 19, No. 6, (2001), 1089-97.
O'Driscoll, S W, et al., "The Chondrogenic Potential of Free Autogenous Periosteal Grafts for Biological Resurfacing of Major Full-Thickness Defects in Joint Surfaces Under the Influence of Continuous Passive Motion. An Experimental Investigation in the Rabbit.", J Bone Joint Surg Am, vol. 68, No. 7, (1986), 1017-35.
O'Driscoll, Shawn W, et al., "The Repair of Major Osteochondral Defects in Joint Surfaces by Neochondrogenesis with Autogenous Osteoperiosteal Grafts Stimulated by Continuous Passive Motion", Clinical Orthopaedics and Related Research, No. 208 Canada, (1986), 131-140.
Oegema, T R, et al., "Characterization of a hyaluronic acid-dermatan sulfate proteoglycan complex from dedifferentiated human chondrocyte cultures", J Biol Chem, vol. 256, No. 2, (1981), 1015-22.
Ohlsen, L, et al., "The Early Development of Articular Cartilage After Perichondral Grafting", Scand J Plast Reconstr Surg, vol. 17, (1983), 163-177.
Oldshue, J Y, et al., "Comparison of Mass Transfer Characteristics of Radial and Axial Flow Impellers", Mixing Proceedings of the 6th European Conference, Pavia, Italy,, (1988), 345-350.
Outerbridge, H K, et al., "The Use of a Lateral Patellar Autologous Graft for the Repair of a Large Osteochondral Defect in the Knee", J Bone Joint Surg Am, vol. 77, No. 1, (1995), 65-72.
Paar, O, et al., "Cartilage Adhesion at the Knee Joint, Clinical Follow Up Examination", Akt. Traumatol, vol. 14, (1984), 15-19.
Paccola, Cleber, et al., "Fresh Immature Articular Cartilage Allografts—A Study on the Integration of Chondral 11 and Osteochondral Grafts Both in Normal and in Papain-Treated Knee Joints of Rabbits", Arch. Orthop. Trauma!. Surg., vol. 93, (1979), 253-259.
Papoutsakis, Eleftherios T, "Fluid-mechanical damage of animal cells in bioreactors", TibTech, vol. 9, Elsevier Science Publishers Ltd. (UK), (1991), 427-437.
Park, J J, et al., "Comparison of the Bonding Power of Various Autologous Fibrin Tissue Adhesives", Am J Otology, vol. 18, No. 5, (1997), 655-659.
Park, M S, "Tympanoplasty Using Autologous Crushed Cartilage", Rev Laryngol Otol Rhinol, vol. 116, No. 5, (1995), 365-368.
Pascone, M, et al., "Fibrin Sealant in Plastic Surgery of the Head, Plastic Surgery Nerve Repair Burns, Fibring Sealing in Surgical and Nonsurgical Fields", vol. 3, Springer-Verlag, Berlin Heidelberg, (1995), 11-15.
Passl, R, et al., "Fibrin Gluing of Cartilage Surfaces-Experimental Studies and Clinical Results", Med U Sport, vol. 19 (1/2), (1979), 23-28.
Passl, R, et al., "Histological Observations After Replantation of Articular Cartilage Using Fibrin Sealant", Traumatology and Orthopaedics vol. 12, (1986), 194-199.
Passl, R, et al., "Homologous Articular Cartilage Transplantation in Animal Experiments. Preliminary Studies on Sheep (author's transl)", Arch Orthop Unfallchir, vol. 86, No. 2, (1976), 243-56.
Passl, R, et al., "Homologous Cartilage Transplants in Animal Experiments", 4th Orthopedics Symposium, Heidelberg, Horst Cotta and Arnim Braun (eds), Georg Thieme Verlag Stuttgart, New York, (1981), 102-105.
Passl, R, et al., "Problems of Pure Homologous Articular Cartilage Transplantation", Verh Anat Ges, vol. 70, (1976), 675-678.
Passl, R., et al., "Fibrin Sealing of Cartilage Surfaces", Beitr. Orthop. Tramatol vol. 36, Nos. 10 and 11, (1989), 503-507.
Pavesio, Allesandra, et al., "Hyaluronan-based scaffolds (Hyalograft C) in the treatment of knee cartilage defects; preliminary clinical findings", Hyaluronan Scaffolds in Cartilage Repair, UK, (2003), 203-217.
Pech, A, et al., "Tissuecol in Septorhinoplasties", Ann Oto-Laryng, vol. 105, Abstract Only, (1988), 629-634.
Peer, L A, "Extended Use of Diced Cartilage Grafts", Meeting of the American Association of Plastic Surgeons, (Apr. 21, 23, 1954), 178-185.
Peer, L A, "Fate of Autogenous Septal Cartilage After Transplantation in Human Tissues", Archive of Otolaryngology, vol. 34, No. 4, (1941), 696-709.
Peer, L A, "The Fate of Living and Dead Cartilage Transplanted in Humans", Surg Gynec, and Obst, vol. 68, (1939), 603-610.
Peer, L A, "The Neglected Septal Cartilage Graft (With Experimental Observations on the Growth of Human Cartilage Grafts)", Arch Otolaryngol Head Neck Surg, vol. 42, No. 5, (1945), 384-396.
Peer, L. A, "Transplantation of Tissues-Cartilage, Bone, Fascia, Tendon, and Muscle", The Williams & Wilkins Company, vol. 1, Baltimore, Maryland USA, vol. 1, (1955), 69-137 & 392-393.
Peer, Lyndon, "Diced Cartilage Grafts—New Method for Repair of Skull Defects, Mastoid Fistula and Other Deformities", Archives of Otolaryngology, vol. 38, No. 2, (1943), 156-165.
Peretti, G M, et al., "Meniscal repair using engineered tissue", J. Orthop Res, vol. 19, No. 2., (2001), 278-85.
Peretti, Giuseppe M, et al., "A biomechanical Analysis of an Engineered Cell-Scaffold Implant for Cartilage Repair", Annals of Plastic Surgery vol. 46 No. 5, (May 2001), 533-537.
Peretti, Giuseppe M, et al., "Biomechanical analysis of a chondrocyte-based repair model of articular cartilage", Tissue Engineering 5(4), (1999), 317-326.
Peretti, Giuseppe M, et al., "Bonding of cartilage matrices with cultured chondrocytes: an experimental model", Journal of Orthopaedic Research 16(1), (1998), 89-95.
Peretti, Giuseppe M, et al., "Cell-based bonding of articular cartilage: An extended study", Wiley Periodicals, Inc., (2003), 517-524.
Peretti, Giuseppe M, et al., "Cell-Based Tissue-Engineered Allogenic Implant for Cartilage Repair", Tissue Engineering, vol. 6 No. 5, (2000), 567-576.
Peretti, Giuseppe M, et al., "In vitro bonding of pre-seeded chondrocytes", Sport Sciences for Health, V. 2, (2007), 29-33.
Phemister, D B, et al., "The Method of New Joint Formation in Arthroplasty, Surgery, Gynecology and Ostetrics", vol. 26, (1918), 406-447.
Pierce, Angela, et al., "Surgicel: macrophage processing of the fibrous component", International Journal of Oral Maxillofac Surgery vol. 16, (1987), 338-345.
Pierce, G W, et al., "Reconstruction Surgery of the Nose", XXXVI, Ann Otol Rhin and Laryng, vol. 47, (1938), 437-452.
Pieter, A, et al., "Effect of Purified Growth Factors on Rabbit Articular Chondrocytes in Monolayer Culture, I", DNA Synthesis, Arthritis & Rheumatism, vol. 25, No. 10, (1982), 1217-1227.
Piragine, F, et al., "Use of Bovine Heterologous Cartilage and Fibrin Sealant in Middle Ear Reconstructive Surgery", Neurosurgery Ophthalmic Surgery Ent, Fibrin Sealing in Surgical and Nonsurgical Fields, vol. 5, Springer-Verlag, New York USA, (1994), 193-198.

(56) References Cited

OTHER PUBLICATIONS

Pirsig, W, et al., "Regeneration of Septal Cartilage in Children after Septoplasty. A histological Study.", English Abstract only. Acta Otolaryngol, vol. 79, No. 5-6, (1975), 451-9.

Pitman, M I, et al., "The Use of Adhesives in Chondrocyte Transplantation Surgery: In-Vivo Studies", Bull Hosp Jt Dis Orthop Inst, vol. 49, No. 2, (1989), 213-20.

Plaga, B R, et al., "Fixation of Osteochondral Fractures in Rabbitt Knees. A Comparison of Kirschner Wires, Fibrin Sealant, and Polydioxanone Pins", Journal Bone Joint Surg Br, vol. 74, No. 2, (1992), 292-6.

Plenk, H Jr, et al., "Trans- and Replantation of Articular Cartilage Using the Fibronogen Adhesive System", Gastpar, H (ed). Biology of the articular Cartilage in Health and Disease, Schattauer, Stuttgart, New York, USA, (1980), 439-447.

Plenk, Jr, et al., "Articular Cartilage Transplants in Experiments and Clinical Practice", ACA, Acta Chirurgica Austriaca, vol. 29, No. 137, (1997), 1-4.

Polettini, B, "Experimental Grafts of Cartilage and bone", The Journal of the American Medical Association, vol. 80, Abstract, (1923), 360-361.

Polettini, Bruno, "Su neoformazioni carilaginee ed ossee determinate da innesti di frammenti di cartilagine e d'osso fissati", (1922), 179-192.

Pridie, K. A, et al., "A method of resurfacing osteoarthritic knee joints", J. Bone Joint Surg. 41B-3, (1959), 618-619.

Prudden, T Mitchell, "Experimental Studies of the Transplantation of Cartilage", American Journal of the Medical Sciences, vol. 82, (1881), 360-370.

Punzet, G, et al., "Morphological and Therapeutic Aspects of Osteochondrosis dissecans and Aseptic Bone Necroses", Acta Medica Austriaca, Suppl No. 11, (1978), 17-18.

Redl, H, et al., "Methods of Fibrin Seal Application", Thorac Cardiovasc Surgeon, vol. 30, (1982), 223-227.

Reginato, et al., "Formation of nodular structures resembling mature articular cartilage in long-term primary cultures of human fetal epiphyseal chondrocytes on a hydrogel substrate", Arthritis & Rheumatism, vol. 37, No. 9, (1994), 1338-1349.

Reitzer, Lawrence J, et al., "Evidence that Glutamine, Not Sugar, is the Major Energy Source for Cultured HeLa Cells", The Journal of Biological Chemistry, vol. 254, No. 8, (Apr. 1979), 2669-2676.

Roberts, S, et al., "Autologous Chondrocyte Implantation for Cartilage Repair: Monitoring its Success by Magnetic Resonance Imaging and Histology", Arthritis Res and Therapy, vol. 5, (2003), R60-R73.

Robinson, Dror, et al., "Regenerating Hyaline Cartilage in Articular Defects of Old Chickens Using Implants of Embryonal Chick Chondrocytes Embedded in a New Natural Delivery Substance", Calcified Tissue International, vol. 46, Springer-Verlag New York Inc., USA, (1990), 246-253.

Roemhildt, Maria L, et al., "Material Properties of Articular Cartilage in the Rabbit Tibial Plateau", J Biomech vol. 39 No. 12, (2006), 2331-2337.

Rohrbach, J M, et al., "Biological Corneal Replacement an Alternative to Keratoplasty and Keratoprosthesis? A Pilot Study With Heterologous Hyaline Cartilage in the Rabbit Model", Abstract Only, Klin Monatsbl Augenheikd, vol. 207, No. 3, (1995), 191-6.

Ronga, Mario, et al., "Arthroscopic Autologous Chondrocyte Implantation for the Treatment of a Chondral Defect in the Tibial Plateau of the Knee", Arthroscopy: The Journal of Arthroscopic and Related Surgery, vol. 20, No. 1, Italy, (2004), 79-84.

Ronga, Mario, et al., "Tissue Engineering Techniques for the Treatment of a Comples Knee Injury", Arthroscopy: The Journal of Arthroscopic and Related Surgery, vol. 22 No. 5, Italy, (2006), 576.e1-576.e3.

Rosier, R N, et al., "Transforming growth factor bela: an autocrine regulator of chondrocytes", Connective Tissue Research vol. 20., (1989), 295-301.

Rosselot, G, et al., "Development of a serum-free system to study the effect of growth hormone and insulinlike growth factor-I on cultured postembryonic growth plate chondrocytes", In Vitro Cell Dev Biol vol. 28A., (1992), 235-244.

Roth, E, et al., "Influence of Two Glutamine-Containing Dipeptides on Growth of Mammalian Cells", In Vitro Cellular & Developmental Biology, vol. 24, No. 7, (Jul. 1988), 696-698.

Ruano-Ravina, A, et al., "Autologous Chondrocyte Implantation: A Systematic Review", Osteoarthritis and Cartilage, vol. 14, (2006), 47-51.

Rudderman, R H, et al., "The Fate of Fresh and Preserved, Noncrushed and Crushed Autogenous Cartilage in the Rabbit Model", Ann Plastic Surgery, vol. 32, (1994), 250-254.

Rupp, G, et al., "Fibrin Adhesion of Transposed Autologous Cartilage Bone Grafts to Repair Knee-Joint Defects", Langenbeck's Archives of Surgery, vol. 347, No. 1, (1978), 676-677.

Russlies, M., et al., "A cell-seeded biocomposite for cartilage repair", Annals of Anatomy vol. 184, Urban & Fischer Verlag, UK, (2002), 317-323.

Saidi, K, et al., "Articular Knee Transplant in the Rabbit: Experimental Study and Clinical Projections", Union Medicale du Canada, vol. 100, No. 1, (1971), 88-99.

Saini, Sunil, et al., "Concentric Cylinder Bioreactor for Production of Tissue Engineered Cartilage; Effect of Seeding Density and Hydrodynamic Loading on Construct Development", Biotechnol Prog., vol. 19, American Chemical Society and American Institute of Chemical Engineers, USA, (2003), 510-521.

Salter, R B, et al., "The Biological Effect of Continuous Passive Motion on the Healing of Full-Thickness Defects in Articular Cartilage", JBJS, vol. 62-A, No. 8, (1980), 1232-1251.

Salter, Robert B, et al., "The Biological Concept of Continuous Passive Motion of Synovial Joints: The First 18 Years of Basic Research and Its Clinical Application", Articular Cartilage and Knee Joint Function : Basic Science and Arthroscopy, Raven Press, Ltd., NY, USA, (1990), 335-353.

Sampath, T K, et al., "In Vitro Transformation of Mesenchymal Cells Derived from Embryonic Muscle into Cartilage in Response to Extracellular Matrix components of bone", Proc Natl Acad Sci USA, vol. 81, No. 11, (1984), 3419-23.

Schlag, G, et al., "Fibrin Adhesive System in Bone Healing", Acta Orthop Scand, vol. 54, No. 4, (1983), 655-8.

Schlag, G, et al., "Fibrin Sealant in Orthopedic Surgery", Clin Ortho Rel Res, vol. 227, (1988), 269-285.

Schmidt, Tannin A, et al., "Synthesis of Proteoglycan 4 by Chondrocyte Subpopulations in Cartilage Explants, Monolayer Cultures, and Resurfaced Cartilage Cultures", Arthritis & Rheumatism, vol. 50, No. 9, American College of Rheumatology, USA, (2004), 2849-2857.

Schobel, H, et al., "Compound Prosthesis and Cartilage Layer: Two New Applications of Fibrin Sealing in Reconstructive Middle Ear Surgery, Neurosurgery Ophthalmic Surgery ENT", Fibrin Sealing in Surgical and Nonsurgical Fields, vol. 5, Springer-Verlag, New York, USA, (1994), 186-192.

Schreiber, R E, et al., "A Method for Tissue Engineering of Cartilage by Cell Seeding on Bioresorbable Scaffolds", Ann N Y Acad Science, vol. 875, (1999), 398-404.

Schubert, T, et al., "Long-term effects of chondrospheres on cartilage lesions in an autologous chondrocyte implantation model as investigated in the SCID mouse model", International Journal of Molecular Medicine, vol. 23, (2009), 455-460.

Schwam, B, "Human Amniotic Membrane Transplantation for the Treatment of Ocular Surface Disease", [Online]. Retrieved from the Internet: <URL: http://www.dcmsonline.org/jax-medicine/2002journals/augsept2002/amniotic.htm>, (2002), 7 pgs.

Schwan, B L, "Human Amniotic Membrane Transplantation for the Treatment of Ocular Surface Disease", Human Amniotic Membrane Transplantation, (2002), 1-7.

Schwarz, E R, et al., "Sulfate Metabolism in Human Chondrocyte Cultures", J Clin Investigation, vol. 54, (1974), 1056-1063.

Schwarz, N, et al., "The Influence of Fibrin Sealant on Demineralized Bone Matrix-Dependent Osteoinduction", Clin Ortho Rel Re, No. 238, (1989), 282-287.

(56) References Cited

OTHER PUBLICATIONS

Schwarz, Ray P, et al., "Cell Culture for Three-Dimensional Modeling in Rotating-Wall Vessels: An Application of Simulated Microgravity", Journal of Tissue Culture Meth., Tissue Culture Association, TX, USA, (1992), 51-58.

Selktar, Dror, "Nature's Healing Matrix", Technion Focus, (May 2006), 1.

Sengupta, S, et al., "The Fate of Transplants of Articular Cartilage in the Rabbit", JBJS, vol. 56B, No. 1, (1974), 167-177.

Shahgaldi, B F, et al., "Repair of Cartilage Lesions Using Biological Implants—A Comparative Histological and Biomechanical Study in Goats", Journal of Bone & Joint Surgery, vol. 73-5, UK, (1991), 57-64.

Shands, A R, "The Regeneration of Hyaline Cartilage in Joints", Archives of Surgery, vol. 22, (1931), 137-178.

Shoemaker, S, et al., "Effects of Fibrin Sealant on Incorporation of Autograft and Xenograft Tendons Within Bone Tunnels. A Preliminary Study.", American Journal of Sports Medicine, vol. 17, No. 3, (1989), 318-24.

Silverman, Ronald P, et al., "Adhesion of Tissue-Engineered Cartilage to Native Cartilage", Plastic and Reconstructive Surgery, vol. 105, No. 4, (Apr. 2000), 1393-1398.

Silverman, Ronald P, et al., "Injectable Tissue-Engineered Cartilage Using a Fibrin Glue Polymer", Plastic & Reconstructive Surgery vol. 103 (7), (1999), 1809-1818.

Simms, G F, et al., "Diced Homologous Cartilage in Hemioplasty", Jour Med Soc J J, vol. 49, No. 9, (1952), 406-7.

Sin, Y M, et al., "Studies of the Mechanism of Cartilage Degradation", Journal of Pathology, vol. 142, (1984), 23-30.

Sittinger, M, et al., "Engineering of cartilage tissue using bioresorbable polymer carriers in perfusion culture", Biomaterials 15(6), (1994), 451-6.

Smith, R. Lane, et al., "Effects of Fluid-Induced Shear on Articular Chondrocyte Morphology and Metabolism In Vitro", Journal of Orthopaedic Research, The Journal of Bone and Joint Surgery, Inc., vol. 13, USA, (1995), 824-831.

Sokoloff, L, et al., "In vitro culture of articular chondrocytes", Federation Proc vol. 32., (1973), 1499-1502.

Sokoloff, L., et al., "Sulfate Incorporation by Articular Chondrocytes in Monolayer Culture", Arthritis and Rheumatism vol. 13, No. 2., (1970), 118-124.

Song, C. X, et al., "Formulation and Characterization of Biodegradable Nanoparticles for Intravascular Local Drug Delivery", Journal of Controlled Release vol. 43, No. 2/03,, XP00632668, (Jan. 18, 1997), 197-212.

Sosna, A, et al., "Use of Fibrin Glue in Orthopedics", Acta Chir Orthop Traum, vol. 51, No. 2, (1984), 8-91.

Spangenberg, K M, et al., "Histomorphometric Analysis of a Cell-Based Model of Cartilage Repair", Tissue Engineering, vol. 8, No. 5., (2002), 839-46.

Specchia, Nicola, et al., "Fetal Chondral Homographs in the Repair of Articular Cartilage Defects", Bulletin of the Hospital for Joint Diseases vol. 54 (4), (1996), 230-235.

Stathopoulos, N. A, et al., "Shear Stress Effects on Human Embryonic Kidney Cells in Vitro", Biotechnology and Bioengineering, vol. XXVII, John Wiley & Sons, Inc., USA, (1985), 1021-1026.

Stewart, Matthew C, et al., "Phenotypic Stability of Articular Chondrocytes In Vitro: The Effects of Culture Models, Bone Morphogenetic Protein 2, and Serum Supplemenation", Journal of Bone and Mineral Research, vol. 15, No. 1, (2000), 166-174.

Stiles, C. D, et al., "Dual control of cell growth by somatomedins and platelet-derived growth factor", PNAS vol. 76, No. 3., (1979), 1279-1283.

Stockwell, R. A, "The cell density of human articular and costal cartilage", J. Anal. vol. 101,No. 4., (1967), 753-763.

Stoksted, et al., "Crushed cartilage in nasal reconstruction", J. Laryng. Otol., vol. 100, (1986), 897-906.

Tanaka, H, et al., "A Study on Experimental Homocartilage Transplantation", Arch Orthop Traumat Surg, vol. 96, (1980), 165-169.

Tanaka, H, et al., "Histochemical Studies on Regeneration of Articular Cartilage", Tokushima J Exp Med, vol. 18, (1971), 63-73.

Temenoff, J.S., et al., "Review: tissue engineering for regeneration of articular cartilage", Biomaterials 21, (2000), 431-440.

Thilly, W. G, et al., "Microcarrier Culture: A Homogeneous Environment for Studies of Cellular Biochemistry", Methods in Enzymology vol. LVIII, ISBN 0-12-181958-2, Academic Press, Inc., New York, New York, United States., (1979), 184-194.

Thilly, W. G, et al., "Microcarriers and the problem of high density cell culture", From Gene to Protein: Translation in Biotechnology vol. 19, Academic Press, Inc., New York, New York, United States., (1982), 75-103.

Trattnig, S., et al., "Differentiating normal hyaline cartilage from post-surgical repair tissue using fast gradient echo imaging in delayed gadolinium-enhanced MRI (dGEMRIC) at 3 Tesla", Eur Radial vol. 18., (2008), 1251-1259.

Trattnig, S., et al., "Quantitative T2 Mapping of Matrix-Associated Autologous Chondrocyte Transplantation at 3 Tesla An in vivo Cross-Sectional Study", Investigative Radiology vol. 42, No. 6., (2007), 442-448.

Trattnig, Siegfried, et al., "Matrix-based autologous chondrocyte implantation for cartilage repair: noninvasive monitoring by high-resolution magnetic resonance imaging", Magnetic Resonance Imaging, vol. 23, Elsevier, Austria, (2005), 779-787.

Tuan, R, "A Second-Generation Autologous Chondrocyte Implantation Approach to the Treatment of Focal Articular Cartilage Defects", Arthritis Research & Therapy, V. 9, (2007), 109-112.

Vacanti, C. A, et al., "Synthetic Polymers Seeded with Chondrocytes Provide a Template for New Cartilage Formation", Plastic and Reconstructive Surgery, vol. 88, No. 5, (1991), 753-759.

Vachon, A, et al., "Neochondrogenesis in free Intra-Articular, Periosteal, and Perichondrial Autografts in Horses", American Journal Vet Res, vol. 50, No. 10, (1989), 1787-1794.

Van Susante, Job L.C, et al., "Resurfacing potential of heterologous chondrocytes suspended in fibrin glue in large full-thickness defects of femoral articular cartilage: an experimental study in the goat", Biomaterials vol. 20, (1999), 1167-1175.

Vanderploeg, E. J, et al., "Articular chondrocytes derived from distinct tissue zones differentially respond to in vitro oscillatory tensile loading", Osteoarthritis and Cartilage vol. 16., (2008), 1228-1236.

Venkat, Raghavan V, et al., "Study of Hydrodynamics in Microcarrier Culture Spinner Vessels: A Particle Tracking Velocimetry Approach", Biotechnology and Bioengineering, vol. 49, John Wiley & Sons, Inc., USA, (1996), 456-466.

Verwerd, C.D.A., et al., "Wound Healing of Autologous Implants in the Nasal Septal Cartilage", ORL, vol. 53, (1991), 310-314.

Verwoerd, C.D.A., et al., "Stress and Woundhealing of the Cartilaginous Nasal Septum", Acta Otolaryngol (Stockh) vol. 107, (1989), 441-445.

Verwoerd, C.D.A., et al., "Wound Healing of Autologous Implants in the Nasal Septal Cartilage", Department of Otorhinolaryngology and Pathology, ORL vol. 53, (1991), 310-314.

Vishwakarma, G. K, et al., "Isolation & cryo-preservation of human foetal articular chondrocytes", Indian J. Med Res vol. 98., (1993), 309-313.

Von Schroeder, Herbert P, et al., "The use of polylatic acid matrix and periosteal grafts for the reconstruction of rabbit knee articular defects", Journal of Biomedical Materials Research, vol. 25, (1991), 329-339.

Wagner, P D, et al., "Improved Blood Buffering in High-Altitude Natives?", J Appl Physiol, vol. 93, (2002), 2214-2215.

Wakitani, Shigeyuki, et al., "Repair of Rabbit Articular Surfaces with Allograft Chondrocytes Embedded in Collagen Gel", J. Bone Joint Surg., vol. 71-B, (1989), 74-80.

Wei, X, et al., "The Effect of Sodium Selenite on Chondrocytes in Monolayer Culture", Arthritis and Rheumatism, vol. 29, No. 5, (1986), 660-664.

Welsh, F, et al., "The Alar Cartilage Morseler: A New Instrument", Br J Plastic Surgery, vol. 36, (1983), 483-484.

Wikipedia, "Alpha-2-Macroglobulin", [Online]. Retrieved from the Internet: <URL: http://en.wikipedia.org/w/index.php?oldid=493169420>, (May 18, 2012), 12 pgs.

(56) References Cited

OTHER PUBLICATIONS

Wilflingseder, P, "Cranioplasties by Means of Diced Cartilage and Split Rib Grafts", Min Chir, vol. 38, No. 12, (1983), 837-43.
Wilflingseder, Paul, "Cancellous Bone Grafts", S.A. Medical Journal, (Dec. 14, 1957), 1267-1271.
Wilflingseder, Paul, "Treatment of Mandibular Facial Dysostosis", S.A. Medical Journal, (Dec. 21, 1957), 1296-1298.
Willers, Craig, et al., "Articular cartilage repair: procedures versus products", Expert Rev. Med. Devices, vol. 4., No. 3, Future Drugs Ltd, US, (2007), 373-392.
Williamson, Amanda K, et al., "Compressive Properties and Function-composition relationships of developing bovine articular cartilage", Journal of Orthopaedic Research vol. 19, (2001), 1113-1121.
Wischhofer, E, et al., "The Behaviour of Autologous Spongiosa Transplants from The Dial Crest With and Without Fibrinadhesive in the Canine Femoral Epiphysis", English abstarct only. Unfallheilkunde, vol. 85, (1982), 250-252.
Xu, et al., "Injectable Tissue-Engineered Cartilage with Different Chondrocyte Sources", vol. 113, (2004), 1361-1371.
Xu, Jian-Wei, et al., "Injectable tissue-engineered cartilage with different chondrocyte sources", Plast Reconstr Surg., 113(5), (Apr. 15, 2004), 1361-71.
Yamamoto, Etsuo, et al., "Use of Micro-Sliced Homograft Cartilage Plates in Tympanoplasty", Acta Otolaryngol., suppl. 419, (1985), 123-129.
Yamashita, F., et al., "The Transplantatoin of Autogeneic Osteochondral Fragment for Osteochondritis Dissecans of the Knee", vol. 201, (1985), 43-50.
Yilmaz, Sarper, et al., "Viability of Diced, Crushed Cartilage Grafts and the Effects of Surgical (Oxidized Regenerated Cellulose) on Cartilage Grafts", Plastic & Reconstructive Surgery 108(4), (2001), 1054-1060.
Yoshihashi, Yuji, et al., "Tissue Reconstitution by Isolated Articular Chondrocytes in vitro", J. Jpn. Orthop. Assoc., vol. 58, (1983), pp. 629-641.
Young, F, "Autogenous Cartilage Grafts, An Experimental Study", Surgery, vol. 10, (1941), 7-20.
Young, F, "The Use of Autogenous Rib Cartilage Grafts to Repair Surface Defects in Dog Joints", Surgery, vol. 7, (1940), 254-263.
Zahn, F, "On the Fate of Tissues Implanted in the Organism", Int Med Congr in Geneva, Biology Secion, (Sep. 11, 1877), 1-4.
Zalzal, G., "Cartilage Grafts—Present Status", Head & Neck Surgery, (1986), 363-374.
Zheng, M H, et al., "Matrix-induced autologous chondrocyte implantation (MACI): Biological and Histological Assessment", Tissue Engineering, vol. 13, No. 4., (2007), 737-746.
Zielke, Ronald H, et al., "Glutamine: a major energy source for mammalian cells", Federation Proceedings, vol. 43, No. 1, (Jan. 1984), 121-125.
Zilch, H, et al., "Fibrin glue in osteochondral fractures with small fragments of the upper limb", English summary only. Ann. Chir. Main, vol. 6 No. 2, (1987), 173-176.
Zilch, H, et al., "Fixation of Small Osteochondral Fragments with the Fibrinogel Adhesive", English summary only. Clinical Report, Ann Chir Main, vol. 12, (1980), 77-81.
Zilch, H, et al., "Fixing of Osteochondral Fragments with Fibrinogen Glue. Clinical Experiences.", Akt. Taumatol, vol. 11, (1981), 136.
Zilch, V H, "Animal Experiments Investigating the Fixation of Small Osteochondral Fragments by Means of Fibrin Glue", Handchirurgie, vol. 12, (1980), 71-5.
Zilch, V H, et al., "Gluing Small Osteochondral Fragments with Fibrin Glue in Hand Surgery. Clinical Experiences.", Handchirurgie, vol. 12, (1980), 77-81.

Zimber, M P, et al., "TGF-β Promotes the Growth of Bovine Chondrocytes in Monolayer Culture and the Formation of Cartilage Tissue on Three-Dimensional Scaffolds", Tissue Engineering, vol. 1, No. 3., (1995), 289-300.
"U.S. Appl. No. 11/613,319, Non Final Office Action dated Jun. 19, 2014", 12 pgs.
"U.S. Appl. No. 12/861,404, Notice of Allowance dated Feb. 13, 2014", 7 pgs.
"U.S. Appl. No. 12/976,689, Notice of Allowance dated Mar. 25, 2014", 5 pgs.
"U.S. Appl. No. 12/976,704, Notice of Allowance dated Feb. 6, 2014", 8 pgs.
"U.S. Appl. No. 12/976,704, Supplemental Notice of Allowability dated Apr. 14, 2014", 4 pgs.
"U.S. Appl. No. 13/951,762, Examiner Interview Summary dated Apr. 16, 2014", 3 pgs.
"U.S. Appl. No. 13/951,762, Final Office Action dated Mar. 14, 2014", 7 pgs.
"U.S. Appl. No. 13/951,762, Non Final Office Action dated Jun. 9, 2014", 5 pgs.
"U.S. Appl. No. 13/951,762, Response filed May 14, 2014 to Final Office Action dated Mar. 14, 2014", 10 pgs.
"Canadian Application Serial No. 2,684,040, Office Action dated Mar. 3, 2014", 3 pgs.
"International Application Serial No. PCT/US2004/041591, International Search Report and Written Opinion dated May 18, 2005", 4 pgs.
"International Application Serial No. PCT/US2008/060078, International Preliminary Report on Patentability dated Oct. 13, 2009", 9 pgs.
"U.S. Appl. No. 12/101,553, Non Final Office Action dated Oct. 5, 2015", 8 pgs.
"U.S. Appl. No. 12/101,553, Response filed Sep. 9, 2015 to Final Office Action dated May 5, 2015", 13 pgs.
"U.S. Appl. No. 13/327,265, Notice of Allowance dated Jun. 5, 2015", 8 pgs.
"Canada Application Serial No. 2,684,040, Office Action dated Oct. 21, 2015", 3 pgs.
"Database WPI Week 200348", Thomson Scientific , London, GB, (Jul. 2, 2003), 1 pg.
"European Application Serial No. 06813900.5, Extended European Search Report dated Oct. 2, 2015", 6 pgs.
"Canadian Application Serial No. 2,684,040, Response filed Mar. 11, 2016 to Office Action dated Oct. 21, 2015", 2 pgs.
"Canadian Application Serial No. 2,684,040, Response filed Aug. 8, 2014 to Office Action dated Mar. 3, 2014", 9 pgs.
"Canadian Application Serial No. 2,684,040, Response filed Sep. 3, 2015 to Office Action dated Mar. 12, 2015", 7 pgs.
"European Application Serial No. 08745639.8, Communication Pursuant to Article 94(3) EPC dated Mar. 21, 2016", 4 pgs.
"European Application Serial No. 08745639.8, Response filed Mar. 3, 2015 to Examination Notification Art. 94(3) dated Oct. 24, 2014", 17 pgs.
"European Application Serial No. 08745639.8, Response filed Nov. 10, 2015 to Examination Notification Art. 94(3) dated Apr. 30, 2015", 10 pgs.
"European Application Serial No. 06813900.5, Communication Pursuant to Article 94(3) EPC dated Nov. 11, 2016", 6 pgs.
"European Application Serial No. 08745639.8, Response filed Jul. 29, 2016 to Communication Pursuant to Article 94(3) EPC dated Mar. 21, 2016", 18 pgs.
Moo, E. K., et al., "The metabolic dynamics of cartilage explants over a long-term culture period", Clinics, 66(8), (2011), 1431-1436.

\* cited by examiner

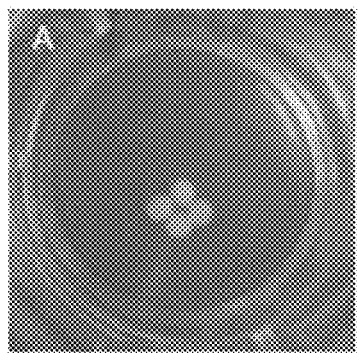 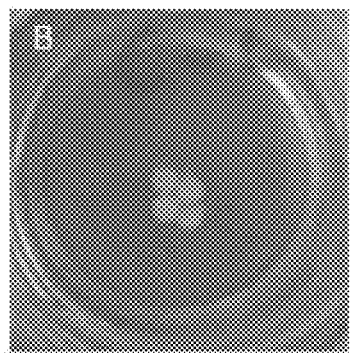 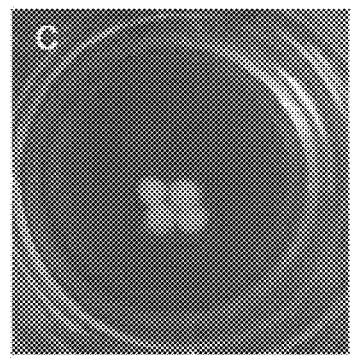
FIG. 18A        FIG. 18B        FIG. 18C
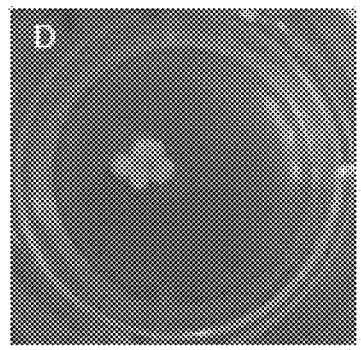 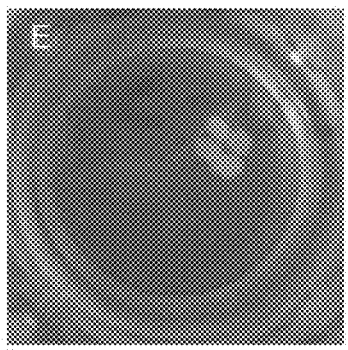
FIG. 18D        FIG. 18E

SUPPORTS AND METHODS FOR PROMOTING INTEGRATION OF CARTILAGE TISSUE EXPLANTS

CROSS-REFERENCE TO RELATED APPLICATIONS

This application is a divisional of U.S. patent application Ser. No. 13/799,452, filed Mar. 13, 2013, which claims priority from U.S. Provisional Application No. 61/740,787, filed Dec. 21, 2012, the benefit of priority of each of which is claimed hereby, and each of which are incorporated by reference herein in its entirety.

TECHNICAL FIELD

The present disclosure relates generally to methods and compositions for expanding cartilage tissue explants in vitro, and in particular to a tissue support for promoting expansion and integration of cartilage tissue particles or pieces, and related methods.

BACKGROUND OF THE INVENTION

Injury and degeneration of cartilage tissue is a major clinical challenge for several reasons. In the epidemiological sense, arthritis and other degenerative joint diseases afflict a large proportion of aging populations, which are growing at high rates in most developed nations. In the clinical sense, healing of cartilage tissue is compromised by a lack of direct blood supply. When cartilage tissue alone is damaged, i.e., in the case of a chondral lesion, local chondrocytes can only achieve limited repair. A full-thickness articular cartilage injury, or osteochondral lesion, will elicit a complete inflammatory response, but results in poor tissue reformation. As a result, a surgical approach to repair and prevention of further injury can be the only viable option. Total artificial joints have been developed and used as replacements for many years with reasonable success. Total joint replacement is nevertheless costly, invasive, carries certain risks such as blood clots, blood loss and infection, and may not provide complete restoration of function. Additionally, although significant advances have been made over the last few decades in designing robust artificial joints, they do wear out. Total joint replacement in patients younger than about 60 must be carefully considered, given the risk of the artificial joint wearing out.

Tissue engineering provides an alternative approach to joint repair. Engineered tissue, including cartilage tissue, can now be prepared in vitro and then implanted in an afflicted joint to replace damaged cartilage. The technical challenge has been how to engineer a tissue that has the biomechanical properties native to cartilage, and is also biocompatible. Various approaches have been tried with differing levels of success. One approach is to obtain cells from an acceptable donor source, and seed the cells onto some sort of scaffold that provides needed mechanical support, and then maintain the arrangement in culture with appropriate nutrients and growth factors with the expectation that the seeded cells will mature, or differentiate and mature, to the desired chondrocyte phenotype. While this approach generally holds promise, multiple technical obstacles remain, arising primarily from the difficulty in finding a suitably strong biocompatible material that also promotes chondrocyte differentiation, proliferation, phenotype retention and ability of chondrocytes to produce appropriate levels of cartilage-specific glycosoaminoglycans. Certain naturally-occurring and synthetic biopolymers have been investigated for such applications, with varying degrees of success.

While significant progress has been made in successfully engineering small amounts of certain types of cartilage, many substantial barriers remain. In particular, engineered cartilage tissue that is sufficiently robust to apply to weight-bearing joints, rather than merely to cosmetic applications, remains a continuing objective. For true functionality within a joint, the resulting tissue must demonstrate the cellular characteristics and architecture of native cartilage, while commercial viability requires that the tissue be readily generated from the relatively small amounts of source tissue that is reasonably available. The field therefore continues to search for improved methods for promoting and sustaining cartilage tissue expansion from small initial amounts of donor tissue.

SUMMARY OF THE INVENTION

In one aspect, the present disclosure provides a support for preparing a cartilage composition from a plurality of cartilage tissue pieces, the support comprising a biocompatible material having a surface defining a plurality of tissue anchors separated by a distance sufficient to secure the plurality of tissue pieces to the support at an inter-piece distance of 1 mm or less. Each tissue piece has a starting volume less than 1 mm$^3$. The biocompatible material may comprise a solid material, such as for example at least one trabecular metal, or a semi-solid material such as for example a gel. The tissue anchors comprise a plurality of surface features such as pins, barbs, ridges, hooks, posts, recesses and/or apertures in the biocompatible material. The support may have a plurality of cartilage tissue pieces coupled to its surface, wherein each cartilage tissue piece is coupled to a tissue anchor on the support so that the tissue pieces are separated by an inter-piece distance of 1 mm or less. A cartilage adhesive is optionally applied to the surface defining the plurality of tissue anchors. The cartilage adhesive may be applied for example to a plurality of predetermined locations on the surface of tissue anchors, in such manner as to confine the cartilage adhesive to the predetermined locations.

Also provided is a kit including any support as described herein, and a first container holding a plurality of cartilage tissue pieces. The kit may further comprise instructions for securing the plurality of cartilage tissue pieces to the tissue anchors on the support. The kit may further comprise a cartilage adhesive, which may be supplied for example in a separate container together with instructions for applying the cartilage adhesive to the surface defining the plurality of tissue anchors on the support. Alternatively, the cartilage adhesive may be applied to the surface defining the plurality of tissue anchors on the support. The cartilage adhesive may be applied for example to a plurality of predetermined locations on the surface of tissue anchors such that the cartilage adhesive is confined to the predetermined locations.

In another aspect, the present disclosure provides a tissue culture system for preparing a cartilage composition for repair of a cartilage tissue defect, the tissue culture system including: a support including a biocompatible material having a surface defining a plurality of tissue anchors separated by a distance sufficient to secure a plurality of tissue pieces to the solid support at an inter-piece distance of 1 mm or less; and a plurality of cartilage tissue pieces, each cartilage tissue piece secured to a tissue anchor. In the tissue culture system, each cartilage tissue piece may have a volume of less than 1 mm$^3$. The tissue culture system may comprise any support as described herein. The cartilage tissue pieces may comprise for example cartilage tissue obtained from a donor, which may be from a juvenile human donor. The cartilage tissue pieces may comprise engineered cartilage tissue.

In another aspect, the present disclosure provides a method for preparing a cartilage composition for repair of a cartilage tissue defect, including: a) dividing cartilage tissue into a plurality of tissue pieces, each portion having an initial volume of less than 1 mm$^3$, and b) maintaining the tissue pieces in a culture medium for a time and under conditions sufficient for each tissue piece to attain an expanded volume of at least 1 mm$^3$, wherein the cell culture conditions comprise securing each tissue piece to a support, wherein the support includes a biocompatible material having a surface defining a plurality of tissue anchors separated by a distance sufficient to secure the plurality of tissue pieces to the solid support at an inter-piece distance of 1 mm or less. In the method, the support may be any of those as described herein. The cartilage tissue pieces may comprise for example cartilage tissue obtained from a donor, which may be from a juvenile human donor. The cartilage tissue pieces may comprise engineered cartilage tissue.

In another aspect, the present disclosure provides a method for repair of a cartilage defect, including: a) dividing cartilage tissue into a plurality of tissue pieces, each portion having an initial volume of less than 1 mm$^3$, and b) maintaining the tissue pieces in a culture medium for a time and under conditions sufficient for each tissue piece to attain an expanded volume of at least 1 mm$^3$, wherein the cell culture conditions comprise securing each tissue piece to a support, wherein the support includes a biocompatible material having a surface defining a plurality of tissue anchors separated by a distance sufficient to secure the plurality of tissue pieces to the solid support at an inter-piece distance of 1 mm or less; c) removing the cartilage composition from the support; and d) implanting the cartilage composition into the cartilage defect. In the method, the support may be any of those as described herein. The cartilage tissue pieces may comprise for example cartilage tissue obtained from a donor, which may be from a juvenile human donor. The cartilage tissue pieces may comprise engineered cartilage tissue. The method may further comprise maintaining the tissue pieces in the culture medium for a time and under conditions sufficient for at least a first expanded tissue piece to attain an expanded volume sufficient for the first expanded tissue piece to contact at least a second expanded tissue piece. The culture conditions may comprise a culture medium including at least one additive from a class of agents selected from the group consisting of: chondrocytes, progenitor cells, stem cells, hormones, growth factors and cytokines.

In another aspect, the present disclosure provides a method for repair of a cartilage defect, including: a) dividing cartilage tissue into a plurality of tissue pieces, each portion having an initial volume of less than 1 mm$^3$; b) maintaining the tissue pieces in a culture medium for a time and under conditions sufficient for each tissue piece to attain an expanded volume of at least 1 mm$^3$, wherein the cell culture conditions comprise securing each tissue piece to a support, wherein the support includes a biocompatible material having a surface defining a plurality of tissue anchors separated by a distance sufficient to secure the plurality of tissue pieces to the solid support at an inter-piece distance of 1 mm or less; and c) implanting and fixing the cartilage composition together with the solid support into the cartilage defect. In the method, the support may be any of those as described herein. The cartilage tissue pieces may comprise for example cartilage tissue obtained from a donor, which may be from a juvenile human donor. The cartilage tissue pieces may comprise engineered cartilage tissue. The method may further comprise maintaining the tissue pieces in the culture medium for a time and under conditions sufficient for at least a first expanded tissue piece to attain an expanded volume sufficient for the first expanded tissue piece to contact at least a second expanded tissue piece. The culture conditions may comprise a culture medium including at least one additive from a class of agents selected from the group consisting of: chondrocytes, progenitor cells, stem cells, hormones, growth factors and cytokines.

In yet another aspect, the present disclosure provides a method for preparing a cartilage composition for repair of a cartilage tissue defect, including: a) dividing an amount of cartilage tissue into a plurality of tissue pieces defining a population, each portion having an initial volume of less than 1 mm$^3$, and b) maintaining the tissue pieces in a culture medium for a time and under conditions sufficient for each tissue piece to expand so that the average volume of tissue pieces in the population is at least 1 mm$^3$. In the method, the culture medium may comprise any of the additives as described herein. The cartilage tissue pieces may comprise for example cartilage tissue obtained from a donor, which may be from a juvenile human donor. The cartilage tissue pieces may comprise engineered cartilage tissue may be any of those as described herein. The method may further comprise maintaining the tissue pieces in the culture medium for a time and under conditions sufficient for each tissue piece to expand so that the average volume of tissue pieces in the population is at least 1.5 mm$^3$. Alternatively, the tissue pieces may be maintained in the culture medium for a time and under conditions sufficient for each tissue piece to expand so that the average volume of tissue pieces in the population is at least 2.0 mm$^3$. In the method, each tissue piece may be positioned on a culture surface at an inter-piece distance of 1 mm or less. The tissue piece may be secured to the culture surface at an inter-piece distance of 1 mm or less as it is positioned. The cartilage adhesive is optionally applied to an interface between each tissue piece and the culture surface.

The cartilage adhesive may be applied for example to a plurality of predetermined locations on the surface, in such manner as to confine the cartilage adhesive to the predetermined locations. The method may further comprise maintaining the tissue pieces in the culture medium for a time and under conditions sufficient for at least a first expanded tissue piece to attain an expanded volume sufficient for the first expanded tissue piece to contact at least a second expanded tissue piece. The culture conditions may comprise a culture medium including at least one additive from a class of agents selected from the group consisting of: chondrocytes, progenitor cells, stem cells, hormones, growth factors and cytokines.

In still another aspect, the present disclosure provides a cartilage composition for repair of a cartilage tissue defect, wherein the cartilage composition includes a plurality of expanded cartilage tissue pieces defining a population, wherein each tissue piece in the population is expanded from an initial volume of less than 1 mm$^3$ to an expanded volume such that the population of expanded cartilage tissue pieces has an average expanded volume of at least 1 mm$^3$. The average volume of expanded cartilage tissue pieces in the population is for example at least 1.5 mm$^3$. Alternatively, the average volume of expanded cartilage tissue pieces in the population is at least 2.0 mm$^3$. In the cartilage composition, each expanded tissue piece in the population contacts at least one other expanded tissue piece. The cartilage tissue pieces may comprise for example cartilage tissue obtained from a donor, which may be from a juvenile human donor. The cartilage composition may further comprise a culture medium including at least one additive from a class of agents selected from the group consisting of: chondrocytes, progenitor cells, stem cells, hormones, growth factors and cytokines. In the provided cartilage composition, the expanded cartilage tissue pieces are obtained by a) dividing an initial amount of cartilage tissue into a plurality of cartilage tissue pieces defining a population, each portion having an initial volume of less than 1 mm$^3$, and b) and maintaining the cartilage tissue pieces in a culture medium for a time and under conditions sufficient for each tissue piece to expand so that the average volume of tissue pieces in the population is at least 1 mm$^3$. For the cartilage composition, the step of obtaining the expanded tissue pieces further comprise before step (b), the step of positioning each tissue piece on a culture surface at an inter-piece distance of 1 mm or less. As a result, the present invention also provides use of the cartilage composition as disclosed herein to repair a cartilage defect in a subject in need thereof.

In yet another aspect, the present disclosure provides a method for repair of a cartilage defect, including: implanting and fixing into the cartilage defect a cartilage composition including a plurality of expanded cartilage tissue pieces defining a population, wherein each tissue piece in the population was expanded from an initial volume of less than 1 mm$^3$ to an expanded volume such that the population of expanded cartilage tissue pieces has an average expanded volume of at least 1 mm$^3$. In the method, the average volume of expanded cartilage tissue pieces in the population is at least 1.5 mm$^3$. Alternatively, the average volume of expanded cartilage tissue pieces in the population is at least 2.0 mm$^3$. In the population of expanded cartilage tissue pieces, at least a first expanded tissue piece contacts at least a second expanded tissue piece. In one example, each expanded cartilage tissue piece in the population contacts at least one other expanded tissue piece. The cartilage tissue pieces may comprise for example cartilage tissue obtained from a donor, which may be from a juvenile human donor. The cartilage tissue pieces may comprise engineered cartilage tissue may be any of those as described herein. The cartilage composition in the method may further comprise a culture medium including at least one additive from a class of agents selected from the group consisting of: chondrocytes, progenitor cells, stem cells, hormones, growth factors and cytokines.

BRIEF DESCRIPTION OF THE DRAWINGS

FIGS. 18A-18E are a series of photomicrographs showing effects of cartilage harvesting locations: A: trochlea, B: trochlea groove, C: femoral condyle, D: central tibial plateau and E: peripheral tibial plateau. Pictures were taken on day 35 of culture.

DETAILED DESCRIPTION

Figure 1:
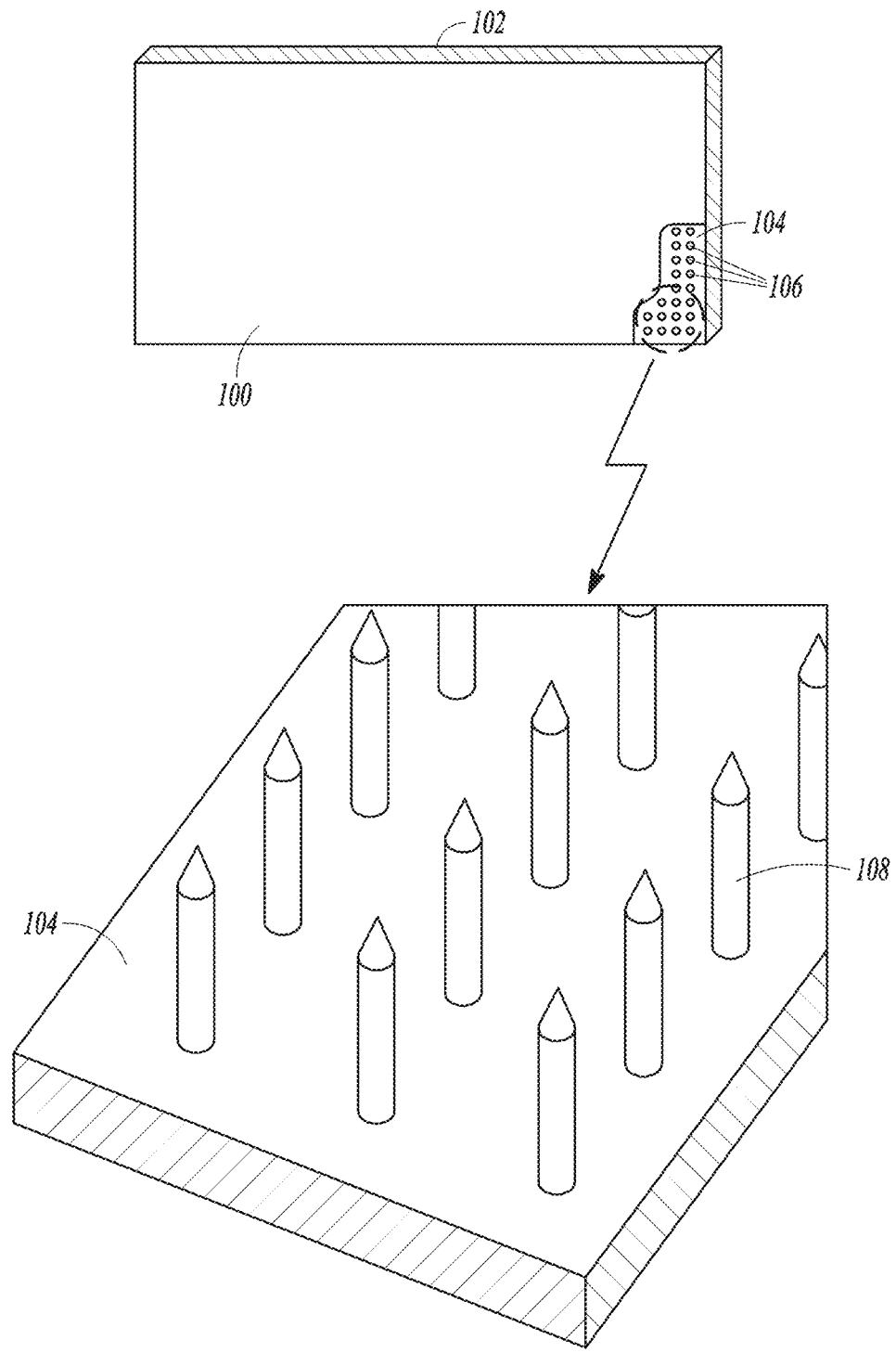
FIG. 1 is a perspective, top view of a first exemplary tissue support with enlarged view of tissue anchors in form of small pins projecting from the upper surface of the tissue support.

The present disclosure is based in part on the surprising discovery that small cartilage tissue pieces, when maintained in vitro under culture conditions, will expand and structurally integrate with neighboring tissue pieces when maintained at an inter-piece distance of 1 mm or less than 1 mm. By "inter-piece distance" is meant that distance from an outside surface of one tissue piece to the closest outside surface of a second tissue piece adjacent to the first tissue piece. Exemplary tissue pieces have a volume of less than about 1 mm$^3$, and may be of many possible shapes, e.g., cubes, cylinders, ovoids, and the like, which may be produced according to the method of preparing the pieces from a tissue source. An outside surface of a tissue piece may therefore be substantially linear or arcuate, depending on the shape of the tissue piece. For example, tissue pieces may be substantially cuboid, with substantially linear outer surfaces, and have a volume of less than about 1 mm$^3$, e.g., dimensions of less than approximately 1 mm on each side. It has now been found that two neighboring cartilage pieces when placed no more than 1 mm apart, form new tissue through the activity of cells that migrate from each piece and interact to form a structurally integrated larger piece of tissue over time. In marked and surprising contrast, neighboring such tissue pieces that are placed more than 1 mm apart do not expand and integrate in the same way. Importantly, it has further now been demonstrated that when placed and maintained while in culture as described, cells from the initial tissue pieces will migrate into the area between two cartilage pieces and produce extracellular matrix (ECM) simultaneously. The newly formed ECM, along with cells embedded therein, forms new inter-piece tissue that binds neighboring pieces together. Additionally, more cells migrate over time onto the inter-piece tissue, and cells already embedded inside the ECM also continue to proliferate. As a result, the ECM becomes denser, and the volume of the inter-piece tissue, which consists of multiple layers of ECM and cells embedded therein, increases. The increase in tissue volume is reflected in an increase in height, width and/or length of the inter-piece tissue, which also becomes structurally integrated with the neighboring tissue pieces. Particularly surprising is the finding that the thus newly formed inter-piece tissue exhibits structure that is comparable to that of the original cartilage tissue, based on gross and histological evaluation. The expanded tissue thus provides a new source for a cartilage composition that can be used for cartilage repair.

A. Definitions

Section headings as used in this section and the entire disclosure herein are not intended to be limiting. Unless defined otherwise herein, all technical and scientific terms used herein have the same meaning as commonly understood by one of ordinary skill in the art to which this invention belongs.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" refers to approximately a +/−10% variation from the stated value. It is to be understood that such a variation is always included in any given value provided herein, whether or not it is specifically referred to.

As used herein, the term "biocompatible material" or biomaterial refers to a synthetic or natural material that can be used to replace part of a living system or to function when in close contact with living tissue.

As used herein, the term "cartilage" refers to an avascular tissue, having chondrocytes encapsulated within an extracellular matrix. As used herein, cartilage tissue may be donor cartilage tissue or engineered cartilage tissue. "Cartilage," as used herein, encompasses articular cartilage, hyaline cartilage, neocartilage (Adkisson, H. D. et al., Clin. Orthop. 3915: S280-S294, 2001; and U.S. Pat. Nos. 6,235, 316 and 6,645,316), devitalized cartilage, auricular cartilage, cartilage including genetically modified chondrocytes, cartilage from an autogenous source, cartilage from an allogenic source, cartilage from a xenogeneic source, juvenile cartilage, or a combination thereof. In some configurations, cartilage can also comprise chondrocytes differentiated from precursor cells such as mesenchymal stem cells.

As used herein, the term "cartilage adhesive" refers to molecular species or mixtures of species which promote adhesion of cartilage tissue or chondrocytes of the cartilage tissue to a surface, by acting as a binding agent (e.g., a glue) and/or by promoting adhesion-forming activity of cells. A cartilage adhesive can be used as a binding agent (e.g., a glue) at the interface between cartilage or chondrocytes thereof and a surface.

The term "cartilage defect" refers to a structural and/or biological imperfection in cartilage tissue such as but not limited to a break, tear, void or other disintegration of the tissue, which is caused by a disease, injury or condition and which can benefit from cartilage repair, replacement, or augmentation, such as, in non-limiting example, athletic injury, traumatic injury, congenital disorders, osteoarthritis and joint degeneration from aging.

As used herein, the term "chondrogenic cell" as used herein refers to chondrogenic progenitor cells (CPCs), the further differentiation of which results in chondrocytes. Chondrogenic cells can come from a variety of sources. Generally, the chondrogenic cells can be isolated from an articular cartilage or a fibrocartilage. Chondrogenic cells from a fibrocartilage can be obtained from costal, nasal, auricular, tracheal, epiglottic, thyroid, arytenoid and cricoid cartilages. Alternatively, cells from fibrocartilage can be obtained from tendon, ligament, meniscus and intervertebral disc. Depending on the context, chondrogenic cells may refer to partially differentiated progenitor cells destined to be chondrocytes or chondrogenic stem cells that are more primitive. The chondrogenic stem cells can be derived from a tissue such as placenta, umbilical cord, bone marrow, skin, muscle, fat, periosteum, and perichondrium.

The term "subject" as used herein refers to a mammal, which may be a human or a non-human mammal such as but not limited to a horse, a dog, a cat, a non-human primate such as a monkey or ape, a rabbit, a rat, a mouse, or a pig.

The term "trabecular metal," as used herein, encompasses any biocompatible metal or metal composite having interconnecting pores and at least 30%, at least 40%, at least 50%, at least 60%, at least 70%, at least 80%, or at least 85% porosity by volume. Exemplary such metals have pores of about 200 µm-700 µm in diameter, and preferably 400 µm-600 µm in diameter. Descriptions of trabecular metal, as well as various methods of making trabecular metal of various pore sizes are known in the art. An exemplary such material is a tantalum composite sold as TRABECULAR METAL® by Zimmer, Inc.

B. Tissue Supports

In one aspect, the present disclosure provides a support for preparing a cartilage composition from a plurality of cartilage tissue pieces, the support including a biocompatible material having a surface defining a plurality of tissue anchors separated by a distance sufficient to secure the plurality of tissue pieces to the support at an inter-piece distance of 1 mm or less. Tissue pieces of varying initial volumes may be used. A tissue piece may for example have a starting volume of about 1 mm$^3$, or less than about 1 mm$^3$, or more than about 1 mm$^3$. For example, a population of tissue pieces having an initial average volume of less than 1 mm$^3$, maintained at an inter-portion distance of 1 mm or less, can expand as described herein to attain an average volume of at least 1.5 mm$^3$ or 2.0 mm$^3$ and thereby integrate with surrounding pieces. It should nevertheless be appreciated that if the tissue pieces are cultured under more favorable expansion conditions, for example by the addition of growth factors to the culture system, the tissue pieces may attain a greater volume within a given period of time, and thereby integrate two neighboring pieces that are maintained at a distance of more than 1 mm apart.

Similarly, with respect to the initial volume of the tissue pieces, although an exemplary tissue piece size is about 1 mm$^3$, or less than about 1 mm$^3$, the initial tissue size (volume) could be larger than about 1 mm$^3$ and still suitably expand as described herein.

Tissue pieces may vary in shape and may be for example substantially spherioid, cuboid, cylindrical, or ovoid. It should be understood that the shape of the tissue pieces will depend in part on the method used to prepare tissue pieces from the donor tissue. A non-limiting exemplary tissue piece is substantially cuboid and has a starting volume less than about 1 mm$^3$, e.g., dimensions of less than approximately 1 mm on each side. The biocompatible material may comprise a solid material, such as for example at least one trabecular metal, or a semi-solid material such as for example a gel.

The tissue anchors comprise a plurality of surface features such as pins, barbs, ridges, hooks, posts, recesses and/or apertures in the biocompatible material. The support may have a plurality of cartilage tissue pieces coupled to its surface, wherein each cartilage tissue piece is coupled to a tissue anchor on the support so that the tissue pieces are separated by an inter-piece distance of 1 mm or less. A cartilage adhesive is optionally applied to the surface defining the plurality of tissue anchors. The cartilage adhesive may be applied for example to a plurality of predetermined locations on the surface of tissue anchors, in such manner as to confine the cartilage adhesive to the predetermined locations. Alternatively, the tissue anchors may be provided solely as adhesive spots in predetermined locations on an otherwise featureless surface of the support.

Figure 2:
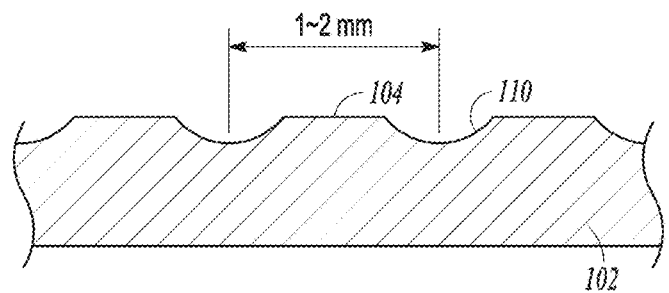
FIG. 2 is a cross-sectional view of a second exemplary tissue support, showing tissue anchors in the form of recessions on the upper surface of the tissue support.

Accordingly, the present disclosure encompasses tissue supports for maintaining tissue pieces at an inter-piece distance of 1 mm or less. As shown in FIG. 1 for example, a tissue support 100 is generally made of a biocompatible material 102 having a surface 104 defining multiple tissue anchors 106 for securing tissue pieces to support 100. The tissue anchors may take the form of any of a number of suitable surface projections from surface 104. As shown in FIG. 1, for example, each tissue anchor is a pin 108. Other projecting forms suitable for securing tissue pieces can be used, such as but not limited to barbs, ridges, hooks, or straight or curved posts. Alternatively, the tissue anchors may generally take the form of depressions or recesses 110 in surface 104, as shown in FIG. 2, or they may consist of apertures through biocompatible material 102. Such depressions, recesses or apertures through biocompatible material 102 may for example be configured with a shape and/or dimensions approximately matched to the shape and/or dimensions of the tissue pieces. For example, apertures for receiving substantially spherical tissue pieces may be configured as round holes through biocompatible material 102, having a diameter approximating the average diameter of the tissue pieces. Alternatively, the tissue anchors may consist solely of defined adhesive locations (not shown) on surface 104, wherein the adhesive locations are created by applying a cartilage adhesive to defined locations, e.g., as "dots" or "spots" of adhesive, on surface 104, which is otherwise free of physical anchors such as projecting anchors, or depressions or apertures.

The multiple tissue anchors are distributed substantially uniformly across surface 104 in any configuration such that each anchor is positioned at a maximum distance of about 1 mm to about 2 mm from at least one neighboring tissue anchor. The distribution of tissue anchors across surface 104 may be according to any regular or irregular pattern, provided that each anchor is no more than a maximum distance of about 1 mm to about 2 mm from at least one neighboring anchor, so that each tissue piece is able to expand and integrate with at least one neighboring piece. It will be appreciated that any distribution pattern that maximizes packing of the initial tissue pieces across surface 104 within the specified maximum distance, and thus any regular, geometric distribution pattern of the tissue anchors, will be preferred.

It should further be appreciated that the tissue anchor dimensions may suitably vary depending on the size and/or density of the tissue piece(s), and on the shape of the anchor. Tissue anchors should be sized and shaped such that the act of applying and securing a tissue piece to an anchor will not obliterate most or all of the tissue piece. For example, a tissue piece having a generally cuboid shape of about 1 mm on a side, or a thinner tissue piece of about 1 mm in length and 1 mm in width, may be anchored to the support surface using an anchor configured as a straight pin, with a largest diameter of about 50-500 microns. Anchors for tissue pieces larger than about 1 mm on a side may be appropriately sized to have a larger diameter or other cross-sectional area.

It should further be appreciated that the tissue support shape may be varied to approximate the shape of an anatomical target, such that the tissue generated on the support in vitro will approximate the target anatomical shape. For example, a support may have an arcuate shape such that the resulting tissue is appropriately shaped to be implanted at the acetabulum, head of the femur or other curved anatomic surface. A support may have a generally pyramidal shape for implantation at a talar dome lesion or fracture. Other shapes suitably adapted for other anatomical targets are also contemplated.

Figure 3:
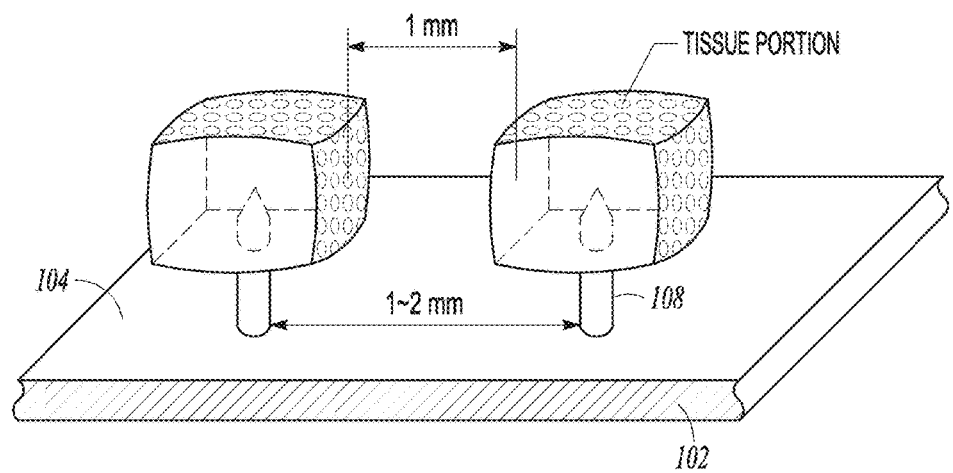
FIG. 3 is a cross-sectional view of the first exemplary tissue support of FIG. 1, showing small tissue pieces placed on the pins.
Figure 4:
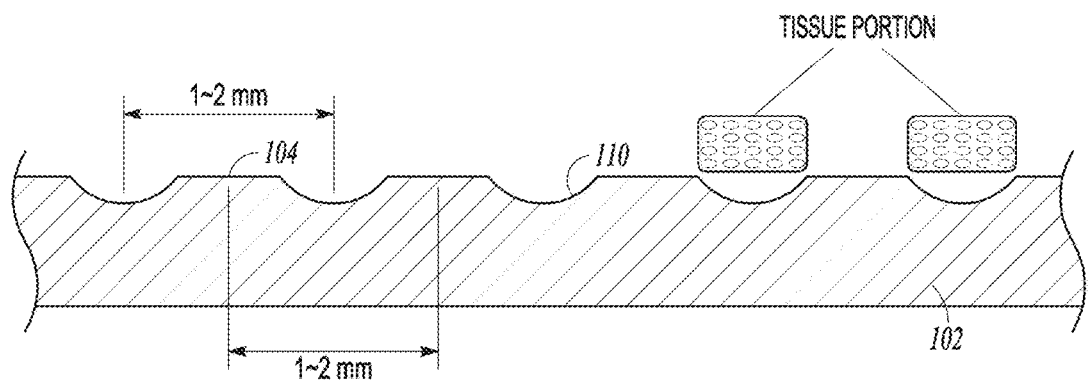
FIG. 4 is a cross-sectional view of the second exemplary tissue support of FIG. 2, showing small tissue pieces placed in the recessions.

Each tissue piece is secured to surface 104 by applying, e.g. manually, each piece at its approximate center onto a tissue anchor, as shown in FIG. 3 and FIG. 4. It should therefore be appreciated that with initial tissue particles having approximate dimensions of 1 mm on each side, using tissue anchors that are separated by a distance of about 1 mm will provide an inter-piece distance of about 0.0 mm, e.g., the initial tissue pieces are in contact or very close to contacting neighboring piece(s). Tissue anchors that are separated by a distance of about 2 mm will provide an inter-piece distance of about 1.0 mm, i.e., a distance at which the initial tissue pieces are at or close to the maximum inter-piece distance, according to the findings and methods disclosed herein. Each piece is secured in position on an anchor by piercing, lancing or hooking the piece onto a projecting anchor on surface 104, or by depositing (e.g., by manually pressing) each piece at least partially into an anchor that is a depression, recess or anchor in surface 104. To use a tissue support that has only adhesive locations as anchors, the cartilage adhesive is applied, e.g. by manually "dotting" or "spotting" the cartilage adhesive onto surface 104 in selected locations, applying a population of tissue pieces to surface 104, waiting for a period of time sufficient for a subset of the tissue pieces to bind or adhere to the selected locations, and then removing all unbound or non-adhered tissue pieces, e.g. by washing or rinsing the unbound pieces way.

A cartilage adhesive is optionally used to further secure each tissue piece in position on the tissue support, for example by the applying cartilage adhesive to an interface between each tissue piece and a tissue support surface. Depending on the configuration of the tissue support, e.g. the type of anchors being used, a cartilage adhesive may be applied to tissue anchor surfaces, or to inter-anchor regions of the tissue support, or to both. Use of a cartilage adhesive may be desired for example when the support has anchors that do not otherwise secure the tissue pieces to the support through physical means such as piercing or hooking, e.g. depressions or apertures. For avoidance of doubt, cartilage adhesive may be used with any of the anchor forms described herein. A cartilage adhesive may be any biologically compatible composition capable of adhering to both biocompatible material 102 and the tissue pieces. For example, a cartilage adhesive may be, but is not limited to, a fibrin-based adhesive, a collagen-based adhesive or a combination thereof. A cartilage adhesive can comprise for example tissue trans-glutaminase, hyaluronic acid, collagen type I, collagen type II, a chemically cross-linked collagen, fibrin, albumin, gelatin, elastin, silk, demineralized bone matrix, polyethylene oxide, polyethylene glycol, polyvinyl alcohol, polypropylene fumarate or a combination thereof as described elsewhere, or a hydrogel. (See, e.g., Jurgensen et al., J. Bone and Joint Surg. 79A: 185-193, 1997; U.S. Pat. No. 6,893,466 to Trieu; U.S. Pat. No. 6,835,277 to Goldberg et al). In various aspects, a vertebrate-derived component of a cartilage adhesive, such as tissue trans-glutaminase, hyaluronic acid, collagen type I, collagen type II, fibrin, albumin, gelatin, or elastin, or demineralized bone matrix, can be autologous, allogeneic, or xenogeneic to a mammalian recipient of an implant, such as a human patient in need of treatment. Furthermore, a protein or polypeptide component of a cartilage adhesive such as tissue trans-glutaminase, hyaluronic acid, collagen type I, collagen type II, fibrin, albumin, gelatin, or elastin, can be obtained from a naturally-occurring source such as an animal or human donor, or can be produced using molecular biological methods well known to skilled artisans, such as expression of a gene or cDNA encoding the protein in transformed or transfected cells (see, e.g., Sambrook, J., et al., Molecular Cloning: A Laboratory Manual, 3rd ed. Cold Spring Harbor Laboratory Press, Cold Spring Harbor, N.Y., 2001). A cartilage adhesive may also comprise one or more cell-attachment factors, such as collagen I or collagen IV, fibronectin, laminin, or polylysine, or another commercially available cell attachment factor, inasmuch as chondrocytes are exposed at a surface of a tissue piece.

The cartilage adhesive may be applied for example to a plurality of predetermined locations on the surface of tissue anchors, in such manner as to confine the cartilage adhesive to the predetermined locations. The cartilage adhesive may be applied for example directly to any projecting anchor such as a pin, hook or barb, to complement the physical coupling of each tissue piece to such an anchor. Alternatively, the cartilage adhesive may be applied to the surface of the support surrounding an anchor that is a depression, recess or aperture through the support, or to the depression or recess itself, or to the internal walls of an aperture, or any combination thereof.

Biocompatible material 102 may comprise any of a number of materials suitable for use in tissue culture and may comprise a material or materials that enhance cell migration, cell attachment and the formation of extracellular matrix of the cells. Such materials include for example a metal, either a single metal or a combination of metals. Accordingly, titanium, cobalt, chromium, platinum, iridium, niobium or tantalum may be used, or any alloy thereof, and also stainless steel. Any metal may be a trabecular metal. Ceramics may be used, such as but not limited to calcium hydroxylapatite (dense or porous), bioactive glass (e.g., BIO-GLASS®, CERAVITAL®), bioactive glass-ceramics (A/W glass-ceramic such as CERABONE®, or dense or porous hydroxyapatite), and workable glass-ceramics and phosphates glasses such as BIOVERIT® I, II and III. Alternatively, suitable biocompatible materials also include biopolymers such as poly-lactic acid (PLA), poly-glycolic acid (PGA), DACRON®, collagen, PET (poly-ethylene terephthalate), poly-carbonate, poly-tetrafluoroethylene, and co-polymers of PLA and PGA. Alternatively, the biocompatible material may comprise a semi-solid material such as for example a gel, such as a hydrogel, or a wax. A biocompatible material may include any combination of any of the above, for example but not limited to a layered configuration with one or more core layers of certain material(s) covered by a surface layer of a different material. Alternatively, protein layers may be attached to the surface of any material to promote cell attachment.

It will be appreciated that the tissue support, though illustrated in the accompanying drawings as a substantially flat surface with tissue anchors projecting therefrom, may alternatively be configured in any shape such as one specially adapted for implantation into a particular defect, provided only that the shape includes at least one surface capable of bearing multiple tissue anchors. It should be further recognized that certain biocompatible materials suitable as the support material and also having some amount of flexibility, such as gels, waxes and any composite material containing a gel or wax, may be especially suitable for in vitro applications.

Methods for manufacturing a tissue support as described will depend on the material(s) selected and desired shape of the support, and are well known in the art. Precision manufacturing services are provided by many contract manufacturing organizations specializing in the manufacture of medical devices which provide manufacturing services including casting, extrusion, molding, and precision machining including milling and micromachining techniques such as microfinishing (deburring and polishing).

C. Methods

The present disclosure encompasses methods for preparing a cartilage composition by dividing cartilage tissue into a plurality of tissue pieces, each having an initial volume of less than 1 mm$^3$, and maintaining the tissue pieces in a culture medium for a time and under conditions sufficient for each tissue piece to attain an expanded volume of at least 1 mm$^3$ or more, e.g. at least 1.5 mm$^3$ or at least 2 mm$^3$. The present disclosure also provides a method for repair of a cartilage defect by implanting and fixing into the cartilage defect a cartilage composition including a plurality of expanded cartilage tissue pieces having an average expanded volume of at least 1 mm$^3$, at least 1.5 mm$^3$ or at least 2 mm$^3$.

In the methods, sufficient time for each tissue piece to attain an expanded volume of at least 1 mm$^3$ or more is at least about 4 days, and can be for example as long as 14 days. While each piece may not actually attain an expanded volume of at least 1 mm$^3$ or more in the time period, it is contemplated that a minimum time of about 4 days under appropriate culture conditions is sufficient for at least 10%, 20%, 30%, 40%, 50%, 60, 70%, 80%, 90% or 100% of the tissue pieces to attain an expanded volume of at least 1 mm$^3$ or more. It should be understood that due to variation among pieces including differences in the microclimate, not all pieces will expand and integrate with neighboring pieces at the same rate. Longer periods of time will result in more pieces attaining a minimum expanded volume, and also more pieces that attain an expanded volume greater the minimum expanded volume.

Tissue culture conditions suitable for expanding and maintaining cartilage tissue as described herein are well known in the art. Generally, tissue including actively dividing cells is grown and maintained at an appropriate temperature which for mammalian cells, is at or about 37° C., and using a gas mixture of 5% $CO_2$. To help accurately control conditions, tissue may be maintained for example in an incubator, in a growth medium. It will be appreciated that the formulation for a suitable growth medium may be varied along several factors: pH, glucose concentration, number and amount of growth factors, and presence of other nutrients. Growth factors derived from a number of sources may be used, including whole animal serum such as bovine calf serum. A suitable growth medium is, in non-limiting example, DMEM/F12 medium supplemented with fetal bovine serum (FBS). Alternatively, a serum-free medium or a chemically defined medium may be used, which may be supplemented with ascorbate and/or glutamine. A suitable such growth medium is, in non-limiting example, HL-1 serum-free medium (Lonza Walkersville, Inc., Walkersville, Md.) supplemented with at least about 2 mM or more of glutamine, and about 50 to about 100 µg/ml ascorbate. A culture medium may include at least one additive from a class of agents selected from the group consisting of: chondrocytes, progenitor cells, stem cells, hormones, growth factors and cytokines, or any composition containing such an additive or additives such as platelet rich plasma (PRP). Progenitor cells and stem cells include for example cartilage progenitor cells or bone marrow cells. Growth factors and cytokines may be any from among the many known such agents, including but not limited to ECGF (Endothelial Cell Growth Factor), VEGF 168, VEGF 145, VEGF 121, aFGF (Fibroblast Growth Factor, acidic), bFGF (Fibroblast Growth Factor, basic), EGF (epidermal growth factor), PDGF (platelet derived growth factor), FGF-10, FGF-4, FGF-5, FGF-6, FGF-8b, FGF-9, IGF (insulin-like growth factor), KGF (Keratinocyte Growth Factor), TGF-β (transforming growth factor β), collagen, hypothemycin, interleukin-8 (IL-8), and IL-13. The hormones may be chosen from hydrocortisone, insulin, triiodothyronine, thyroxine, Retinyl acetate, Activin A, (2-Hydroxypropyl)-β-cyclodextrin, Methyl-β-cyclodextrin, and Hydrocortisone 21-hemisuccinate.

The cell culture conditions may include for example maintaining the tissue pieces at an inter-piece distance of 1 mm or less. This may be accomplished for example by securing each tissue piece to a tissue support as described herein. In use, as shown in FIGS. 3 and 4, tissue support 100 has a plurality of cartilage tissue pieces coupled to its surface via the tissue anchors on support 100, such that the tissue pieces are separated by an inter-piece distance of 1 mm or less. It should be understood however that other means for maintaining the inter-piece distance are encompassed by the present disclosure.

The methods further encompass methods for repairing a cartilage defect, for example in a subject. The cartilage expansion methods as described herein may be applied for example to methods to prepare a cartilage composition in vitro for subsequent implantation into a subject for repair of a cartilage tissue defect in the subject. Alternatively, the approach can be adapted to methods to generate a cartilage composition in vivo in the subject.

A method for repair of a cartilage defect may include for example producing in vitro a cartilage composition on a support, from cartilage pieces each having an initial volume of less than 1 mm$^3$ as described herein, by expanding the initial cartilage pieces in vitro to an expanded volume of at least 1 mm$^3$, followed by removing the resulting cartilage composition from the support, and then implanting and fixing the cartilage composition into the cartilage defect. Alternatively, a method for repair of a cartilage defect may include producing in vitro a cartilage composition on a support as described herein, and then implanting the cartilage composition together with the solid support into the cartilage defect, and closing the surgical opening such that the tissue pieces expand in vivo to an expanded volume of at least 1 mm$^3$ or more. It will be appreciated that the latter alternative favors the use of a tissue support that is either prepared from a flexible material or materials, or is configured in a shape that fits closely with the defect being repaired.

Alternatively, a method for preparing a cartilage composition for repair of a cartilage tissue defect may involve a population of tissue pieces, wherein a) an amount of cartilage tissue is divided into a plurality of tissue pieces defining a population, each portion having an initial volume of less than 1 mm³, and b) the tissue pieces are maintained in a culture medium for a time and under conditions sufficient for each tissue piece to expand so that the average volume of tissue pieces in the population is at least 1 mm³. The tissue pieces may be maintained for a time and under conditions sufficient for each tissue piece to expand such that the average volume of tissue pieces in the population is greater than 1 mm³, for example at least 1.5 mm³, or at least 2.0 mm³. This approach may include positioning each tissue piece on a culture surface, such as a tissue support as described herein, at an inter-piece distance of 1 mm or less before the expansion step (b). Each such tissue piece may be secured to such a support by means of an anchor or a cartilage adhesive, both as described herein, or a combination thereof.

In any of the methods, the tissue pieces, which may be a population of tissue pieces, may be maintained for a time and under conditions sufficient for at least one, or more, of the tissue pieces to expand and thereby attain an expanded volume that is sufficient for the tissue piece(s) to contact at least one neighboring tissue piece that has also expanded. In an exemplary method, a starting population of tissue pieces is maintained for a time and under conditions sufficient for a simple majority if tissue pieces in the population, or for as many as all tissue pieces in the population, or for any number of tissue pieces in between a simple majority and the entire population, to expand and thereby attain an expanded volume that is sufficient for the tissue piece(s) to contact at least one neighboring tissue.

By repair is meant a surgical repair such as an open surgical procedure (arthrotomy) or an arthroscopic procedure by which the in vitro prepared cartilage composition is implanted into the defect, with or without the tissue support. The cartilage composition, or cartilage composition together with the support, may be fixed in the defect using a mechanical fastener such as a staple, screw, pin or the like, or a tissue adhesive such as for example any adhesive described elsewhere herein.

In any of the methods, cartilage tissue pieces or pieces may, without limitation, be prepared from donor or engineered cartilage tissue such as neocartilage, or a combination thereof. Source tissue may be allogeneic to, autologous to, and/or xenogeneic to a mammalian recipient such as a human patient. Cartilage tissue pieces may comprise for example, hyaline cartilage or any tissue including chondrocytes having the potential to generate hyaline cartilage, but not necessarily organized into histologically recognizable cartilage. Such tissue includes, for example, articular joint cartilage including knee joint and hip joint cartilage, tracheal cartilage, laryngeal cartilage, costal cartilage, epiphyseal plate cartilage, and any combination thereof. It will be understood that the methods and devices can be utilized to produce cartilage composition of various sources to meet the needs for treating cartilage defects of any origin. Donor cartilage tissue may be obtained from a live or a deceased donor. Donor cartilage tissue may be obtained for example from a juvenile donor, for example a donor less than fifteen years of age, preferably fourteen years of age or younger, and more preferably two years of age or younger. Donor cartilage tissue may be obtained for example from a prenatal or neonatal donor no older than about one (1) week of age. Donor cartilage tissue may be obtained from a cadaver of an individual of juvenile age at time of death.

Tissue pieces may be prepared from any donor or engineered source tissue by dividing the tissue into cuboids each having a volume less than 1 mm³, e.g cuboids of approximately 1 mm on each side. Dividing may be accomplished for example using a microcutter as known in the art. Multiple such tissue pieces may then be placed in culture, at an edge-to-edge distance of no more than 1 mm from at least one adjacent tissue piece.

Cartilage defects that may be treated with a cartilage composition as described herein encompass any cartilage defect caused by injury or disease including any acute, partial, or full-thickness chondral injury, osteochondral injuries, and defects resulting from degenerative diseases or processes. The cartilage defect can be, for example and without limitation, the result of osteochondritis dissecans (OCD), osteoarthritis, rheumatoid arthritis, or osteonecrosis.

D. Kits and Tissue Culture Systems

Also provided is a kit including a tissue support as described herein, and a first container holding a plurality of the pre-expansion cartilage tissue pieces as also described herein. The kit may be suitably used for investigative or therapeutic purposes to prepare a cartilage composition as described herein from tissue pieces. The kit may further contain, for example, instructions for securing the plurality of cartilage tissue pieces to the tissue anchors on the support. The kit may further comprise a cartilage adhesive, which may be supplied for example in a separate container together with instructions for applying the cartilage adhesive to the surface defining the plurality of tissue anchors on the support. Alternatively, the cartilage adhesive may be applied to the surface defining the plurality of tissue anchors on the support. The cartilage adhesive may be applied for example to a plurality of predetermined locations on the surface of tissue anchors such that the cartilage adhesive is confined to the predetermined locations.

A tissue culture system for preparing a cartilage composition for repair of a cartilage tissue defect may comprise a tissue support as described herein, and a plurality of cartilage tissue pieces, each cartilage tissue piece secured to a tissue anchor as also described herein. In the tissue culture system, each cartilage tissue piece has an initial volume of less than 1 mm³, and may reach an expanded volume of at least 1 mm³, at least 1.5 mm³ or at least 2 mm³. The cartilage tissue pieces in the system may comprise cartilage tissue pieces prepared from any donor or engineered source as described herein. The tissue culture medium may further any growth medium as described herein.

E. Adaptations of the Methods of the Present Disclosure

Various embodiments of the present teachings can be illustrated by the following non-limiting examples. The following examples are illustrative, and are not intended to limit the scope of the claims.

Example 1: Integration of Cultured Cartilage Explants

Cartilage explants were obtained from calf and human juvenile donor tissue and prepared using a microcutter to a substantially cuboid shape of about 1.5 mm on a side. Four 1.5 mm diameter cartilage pieces were placed on a regular tissue culture plate at varying distances relative to each other: at 0, 0.5, 1.0, 2.0 and 3.0 mm and maintained in an incubator at 37° C., 5% $CO_2$, in a growth medium as follows: all cultures were started with DMEM/F-12/FBS medium and switched to HL-1 serum-free medium after two weeks of culture. DMEM/F-12/FBS medium was prepared by supplementing DMEM/F12 medium with 10% (v/v) fetal bovine serum (FBS, Invitrogen) supplemented with ascorbate and L-glutamine as described above, 10,000 U/ml penicillin G, 10,000 U/ml streptomycin sulphate and 25 µg/ml amphotericin B (Invitrogen). Serum free HL-1 medium was prepared from HL-1 serum-free medium (Lonza Walkersville, Inc., Walkersville, Md.) supplemented with 1:100 diluted HL-1 supplement (Lonza Walkersille, Inc.) supplemented with ascorbate and L-glutamine as described above 10,000 U/ml penicillin G, 10,000 U/ml streptomycin sulphate and 25 µg/ml amphotericin B.

Figure 5C:
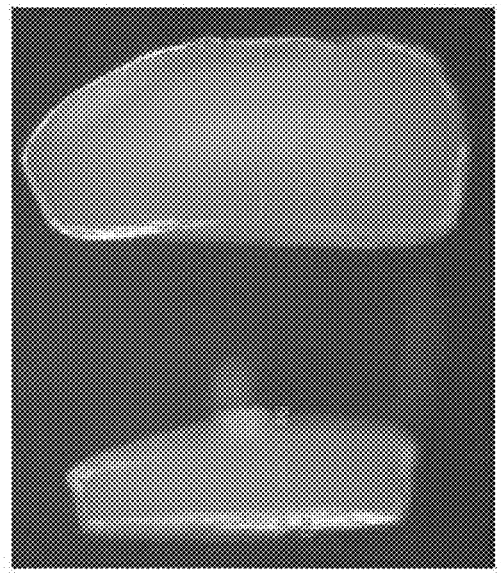
FIGS. 5A-5C are a series of photomicrographs showing expansion of calf and human juvenile cartilage explants in culture.
Figure 5B:
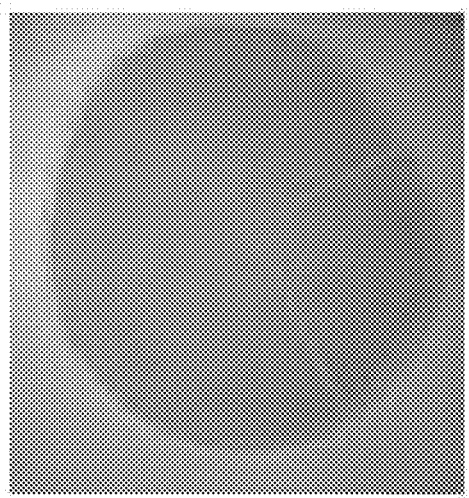
Figure 5A:
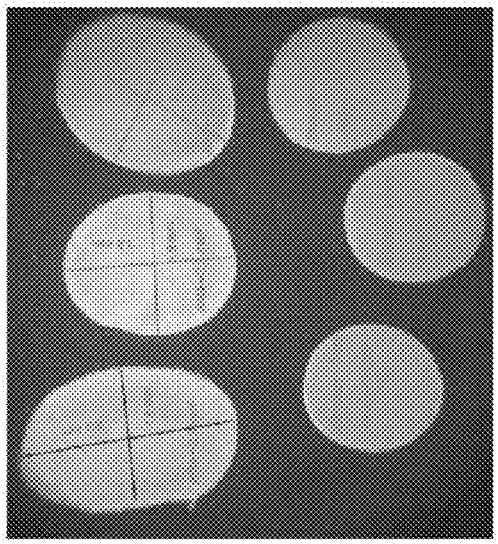
Figures 6A, 6B, 6C:
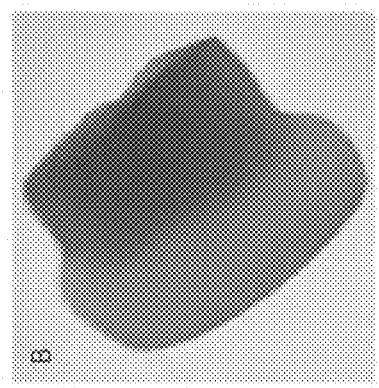
FIGS. 6A-6G are a series of photomicrographs showing non-uniform expansion of cultured cartilage explants.
Figures 6D, 6E, 6F, 6G:
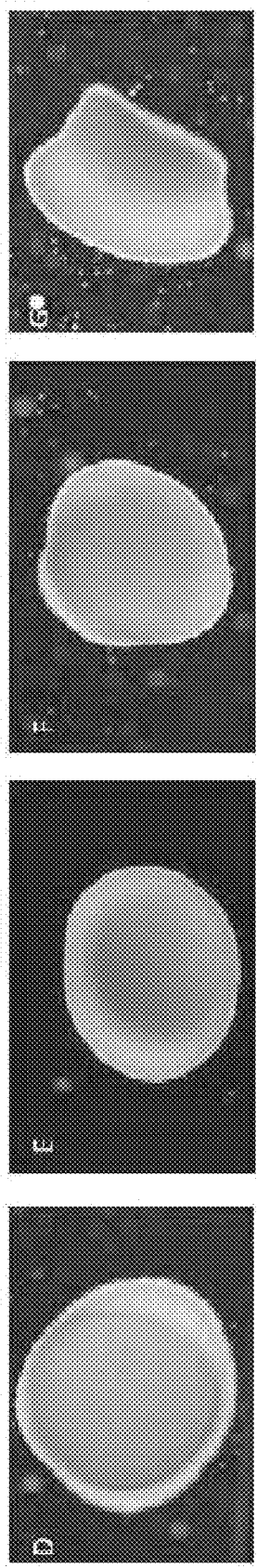

Both calf and human juvenile cartilage explants became bigger and thicker over time. On average, a calf cartilage piece with a 1.5 mm diameter and 1 mm thickness increased 0.6 mm to 1 mm in diameter, and 0.5 to 0.8 mm in thickness over eight weeks of culture (FIG. 5). The cultured cartilage explants did not expand uniformly (FIG. 6). At the surface of the explant adjacent to the surface of the culture plate ("bottom surface" of the explant), the explant expanded more rapidly than at the upper surface, resulting in an asymmetric, generally cylindrical shape with a smaller upper surface relative to a bigger bottom surface, resulting in newly formed tissue appearing as a ring-like structure surrounding the original piece. Spatial reorientation of an explant piece in culture resulted in the same effect on the former upper surface reoriented as the bottom surface. An explant piece flipped over following faster expansion of the initial bottom surface, resulted in comparably rapid expansion of the new bottom surface, so that the resulting explant ended up with two "bigger" surfaces on both sides. Spatial reorientation thus may provide a method of controlling/directing the orientation and shape of cartilage explant expansion.

Figure 7A:
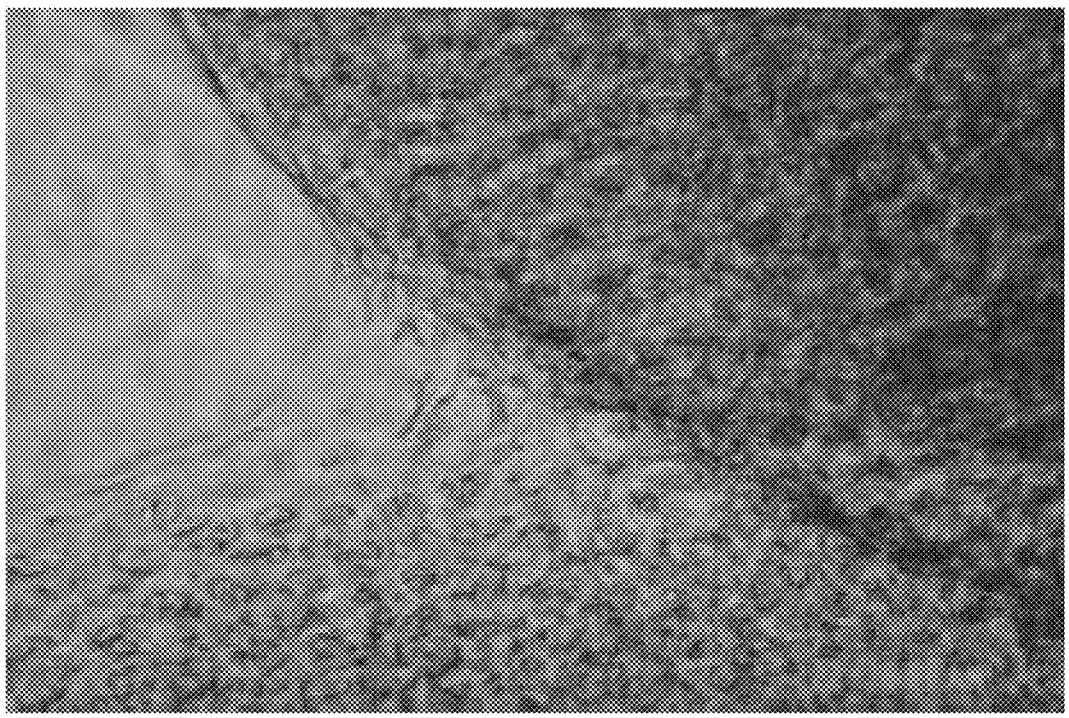
FIGS. 7A and 7B are a photomicrograph showing the structural interactions observed between cultured calf cartilage pieces at day 5 of culture (20×), when maintained at an inter-piece distance of 1 mm.
Figure 7B:
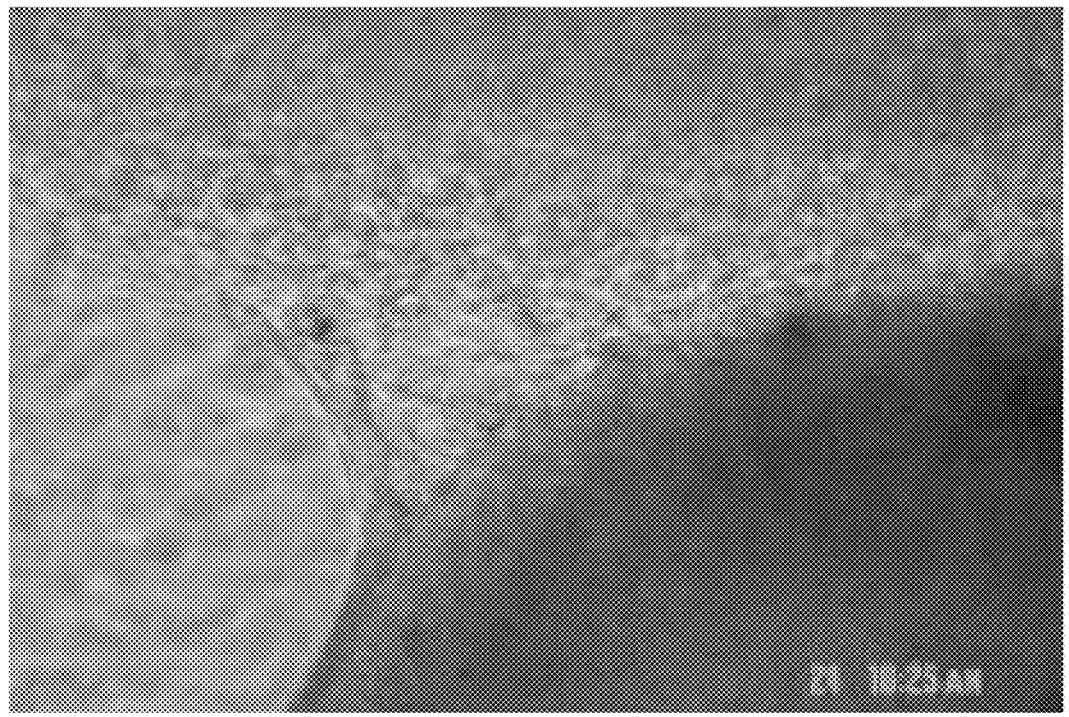
Figure 8:
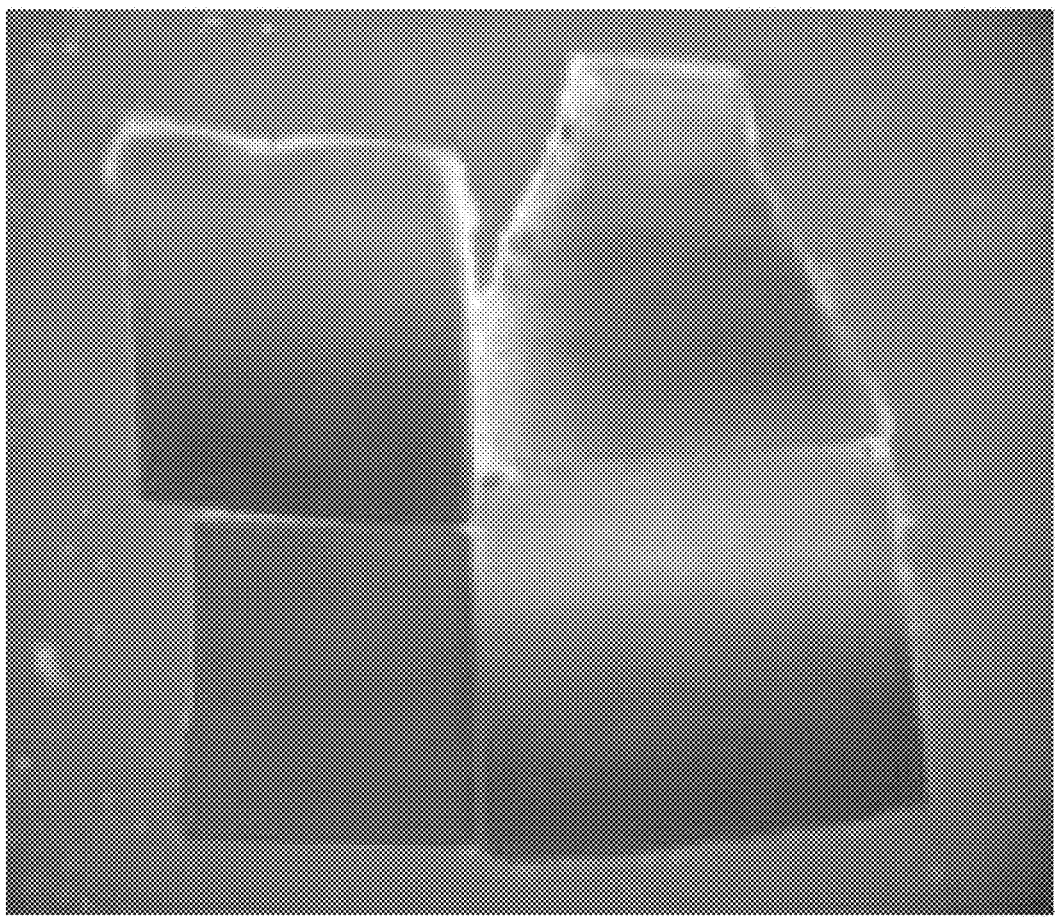
FIG. 8 is a photomicrograph showing the structural interactions observed between cultured human juvenile cartilage pieces at day 5 of culture (5×), when maintained at an inter-piece distance of 1 mm.
Figure 9:
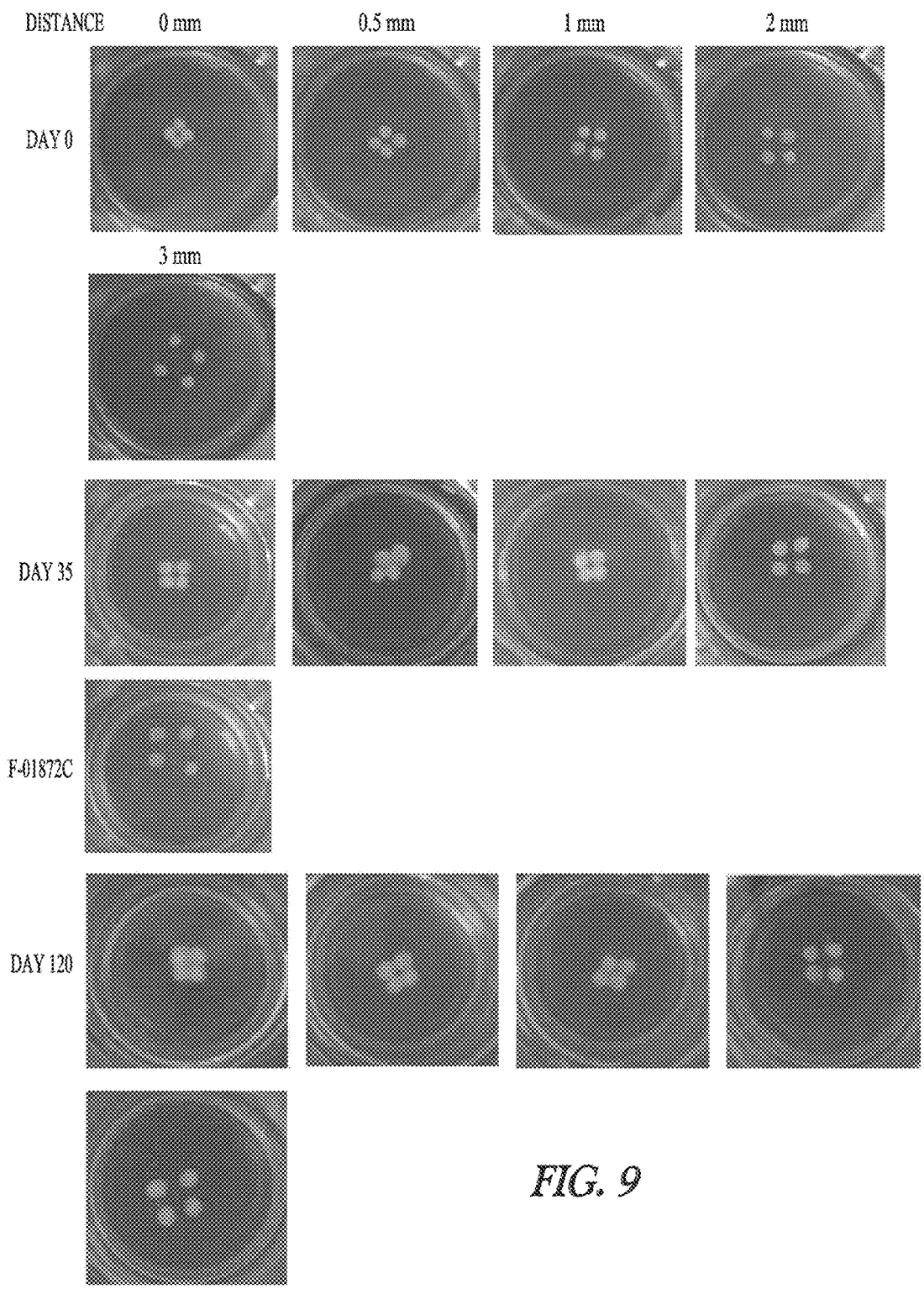
FIG. 9 is a photomicrograph showing results obtained with calf cartilage explants that were cultured with different inter-piece distances, showing structural integration of two neighboring pieces only when they the inter-piece distance was no greater than 1 mm.
Figure 10A:
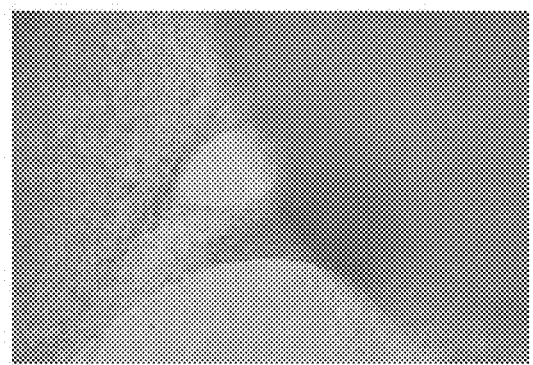
FIGS. 10A-10D are a photomicrograph showing results obtained with calf cartilage explants during an initial culture phase in which inter-piece interactions including simultaneous cell migration into the inter-piece area and production of ECM. Newly formed ECM along with the cells embedded inside can be seen as a bridge between the two neighboring pieces which "glues" the cells together.
Figure 10B:
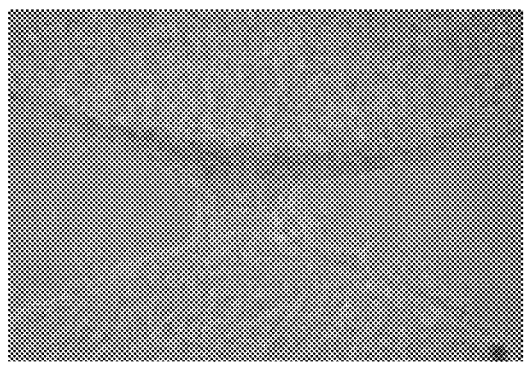
Figure 10C:
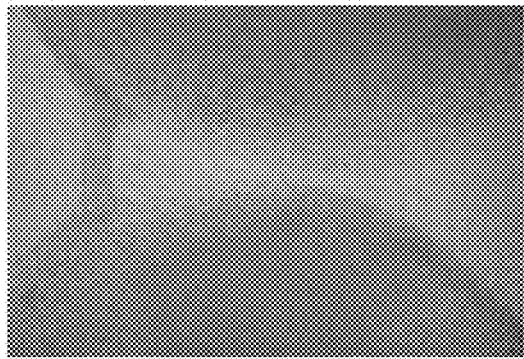
Figure 10D:
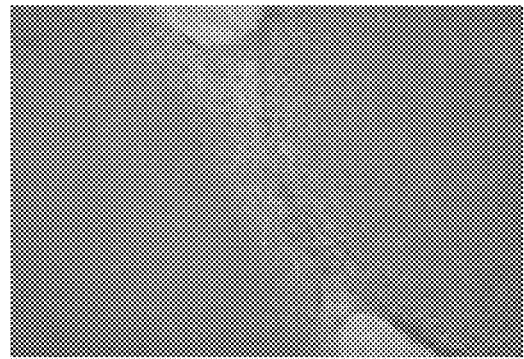
Figure 11A:
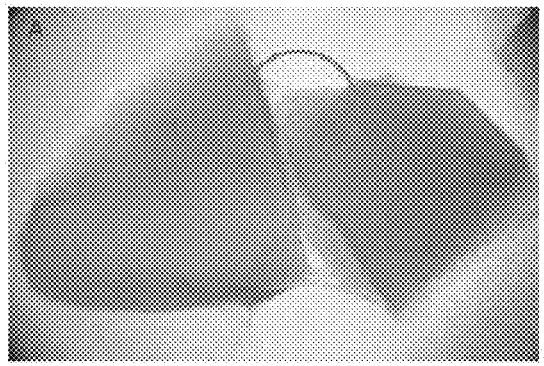
FIGS. 11A-11E are a series of photomicrographs showing the formation of inter-piece interactions of human juvenile cartilage explants. The cells migrated into the inter-piece area and produce ECM simultaneously. The newly formed ECM along, with the embedded cells, can be seen as a bridge between the two pieces which "glues" the cells together. Inter-piece interactions enclosed by the red circle in A (5×) are shown in B (20×). Inter-piece interactions enclosed by the red circles in C (5×) are shown in D and E (20×).
Figure 11B:
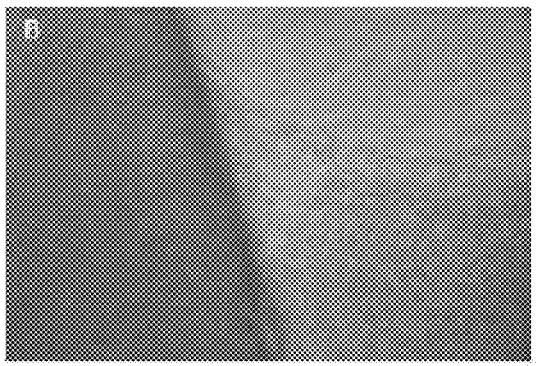
Figure 11C:
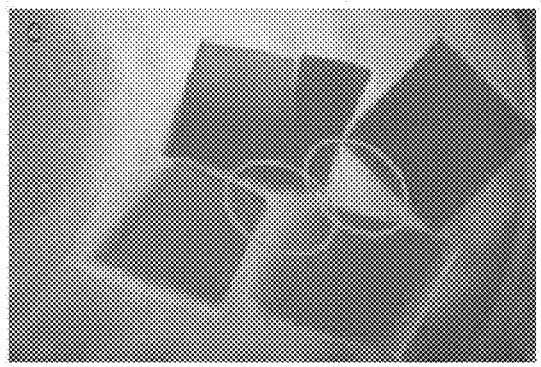
Figure 11D:
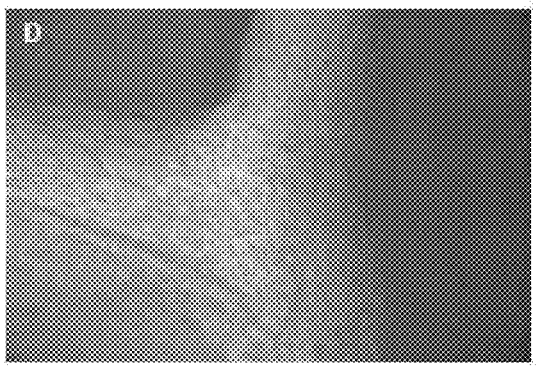
Figure 11E:
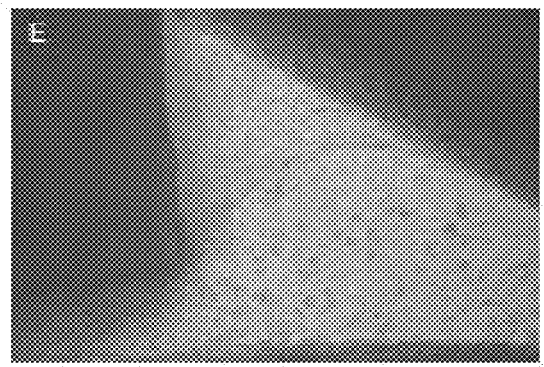

Interactions among the cartilage pieces were generated as early as day 5 of calf cartilage culture (FIG. 7) or day 7 of human juvenile cartilage culture (FIG. 8). These tissue cultures demonstrated that two cartilage pieces were able to structurally integrate to each other only when they were in close proximity, 1 mm or less than 1 mm apart. This occurred in one of two ways: (a) the pieces were placed in contact with each other at the beginning, or (b) the pieces were placed no more than 1 mm apart and the newly formed tissue by the migrated cells integrated with both explants to form a larger piece of tissue over time (FIG. 9).

Figure 12A:
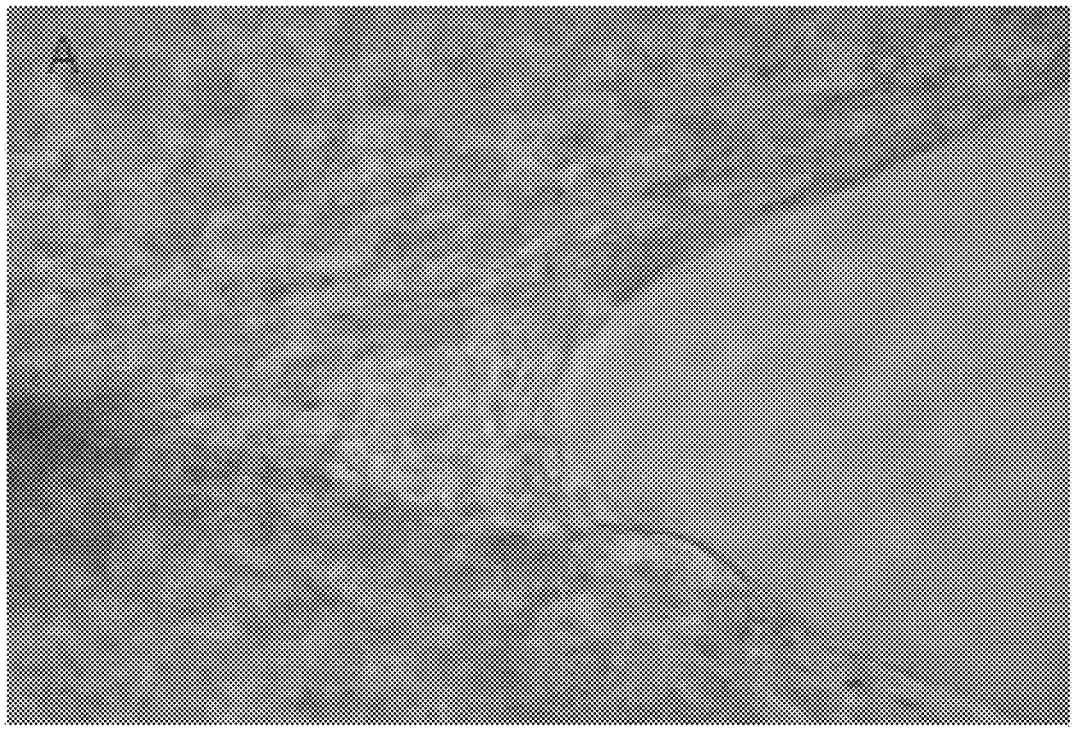
FIGS. 12A and 12B are a pair of photomicrographs of calf cartilage explants showing structural inter-piece interactions over time, which became denser and stringer over time. The newly formed interactions contain both cells and ECM. A: day 24 of culture (20×), B: day 38 of culture (20×).
Figure 12B:
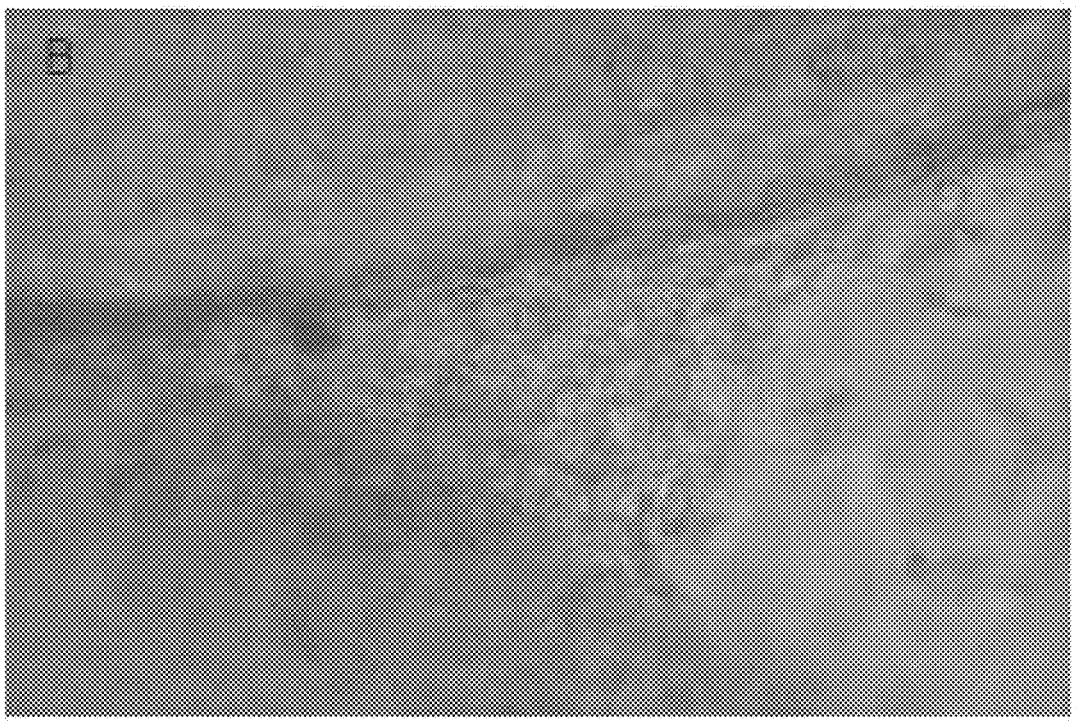
Figure 13A:
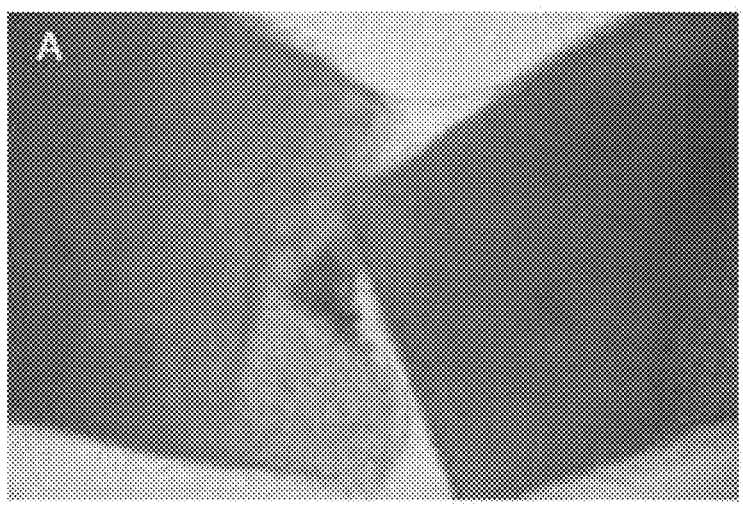
FIGS. 13A-13C are a series of photomicrographs of human juvenile cartilage explants showing the inter-piece interactions over time, which became denser and stronger over time. The newly formed interactions contain both cells and ECM. A: day 26 of culture (10×), B: day 64 of culture (10×). C: the newly formed inter-piece interactions on day 64 of culture (20×).
Figure 13B:
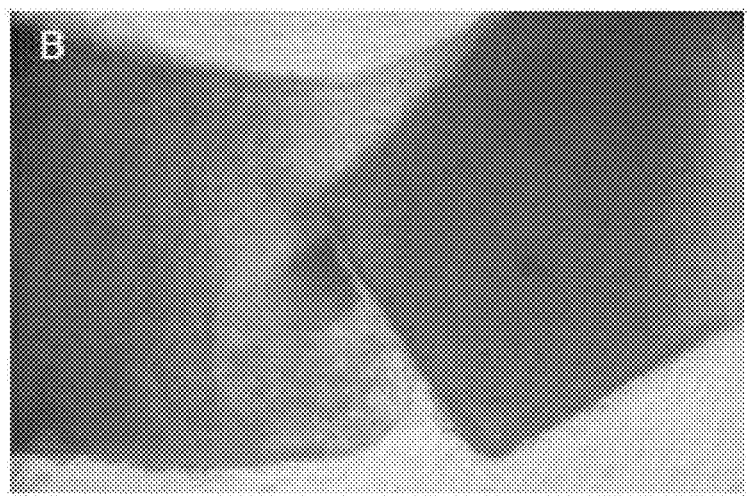
Figure 13C:
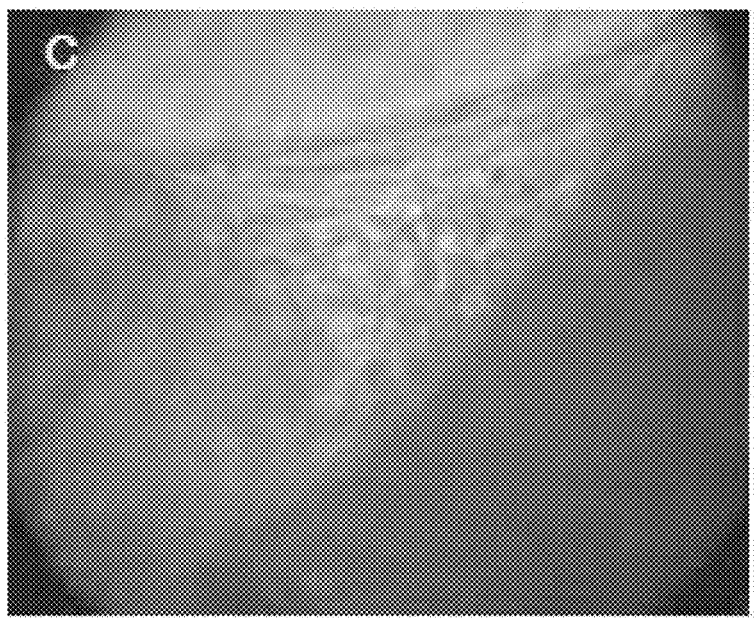
Figure 14A:
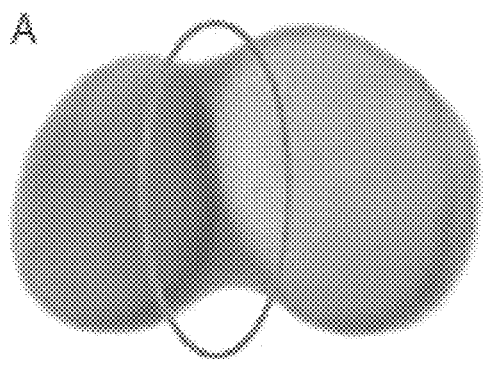
FIGS. 14A and 14B are a pair of photomicrographs of calf cartilage explants showing structural inter-piece interactions over time, which became thicker and wider over time. Inter-piece interactions are highlighted by the red circle. A: day 42 of culture (5×), B: day 120 of culture (5×).
Figure 14B:
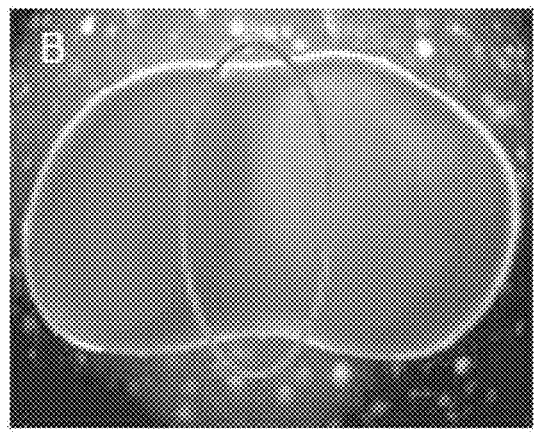
Figure 15A:
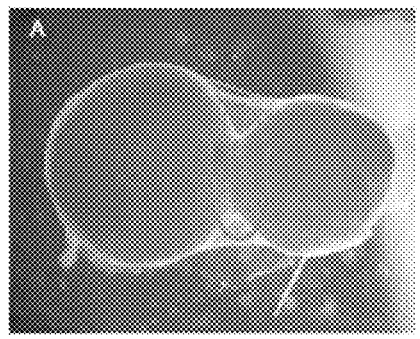
FIGS. 15A-15G are a series of photomicrographs of histologically stained cultured calf cartilage explants at 10 weeks of culture, in which newly formed inter-piece interaction areas are enclosed by the red circles. A: the two calf cartilage pieces at 10 weeks of culture before histology staining B: and C: Masson's trichrome staining, D: and E: H:-E: staining, F: Alcian blue staining and G: Safranin O Staining C: and E: show the cell migration out of the edges of the original calf cartilage pieces.
Figure 15B:
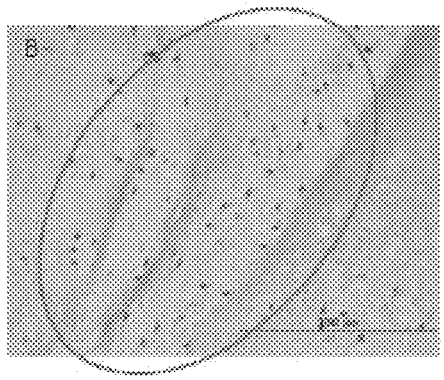
Figure 15C:
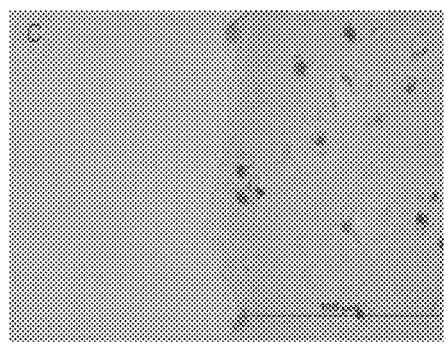
Figure 15D:
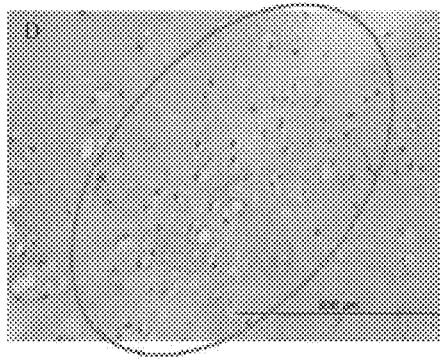
Figure 15E:
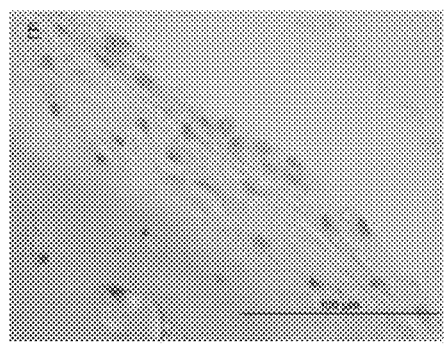
Figure 15F:
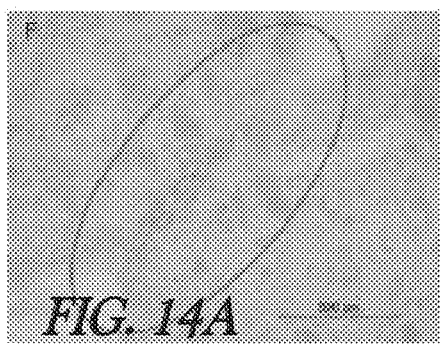
Figure 15G:
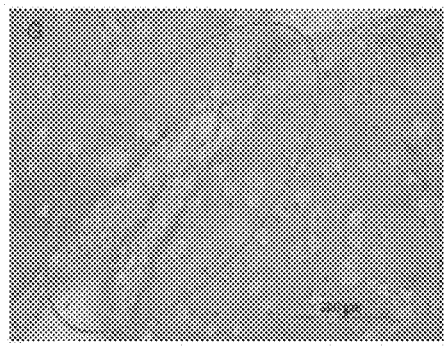
Figure 16A:
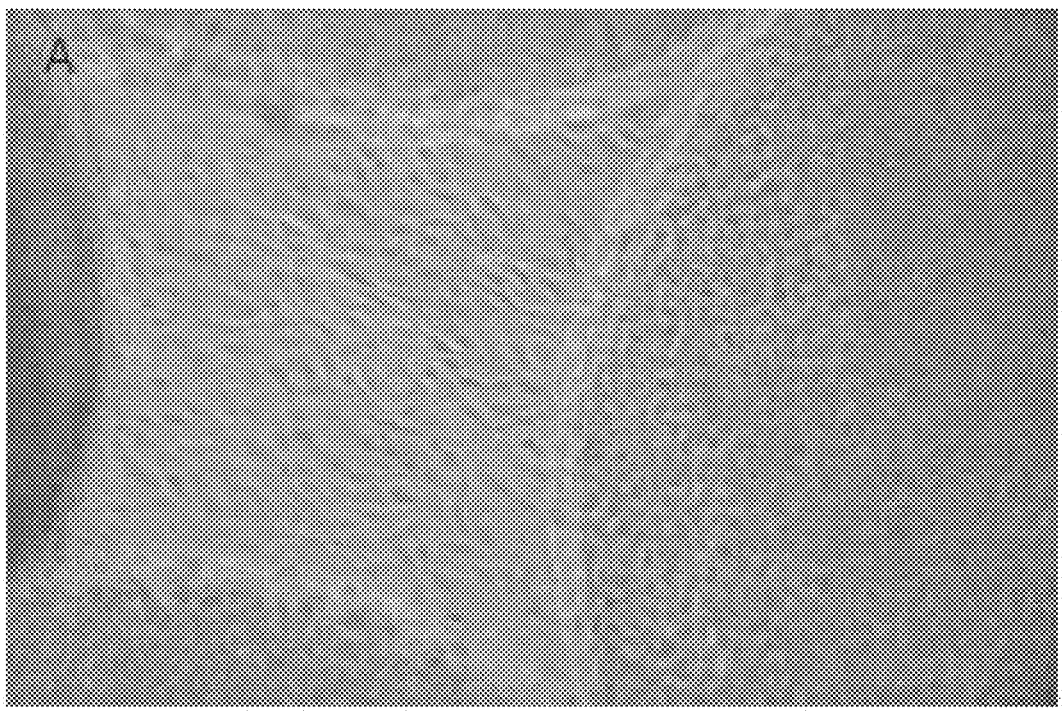
FIGS. 16A and 16B are a pair of photomicrographs showing cultured cartilage pieces positioned at an inter-piece distance of greater than 1 mm were mainly surrounded by the migrated cells. A: calf cartilage explants (10×), B: human juvenile cartilage explants (10×).
Figure 16B:
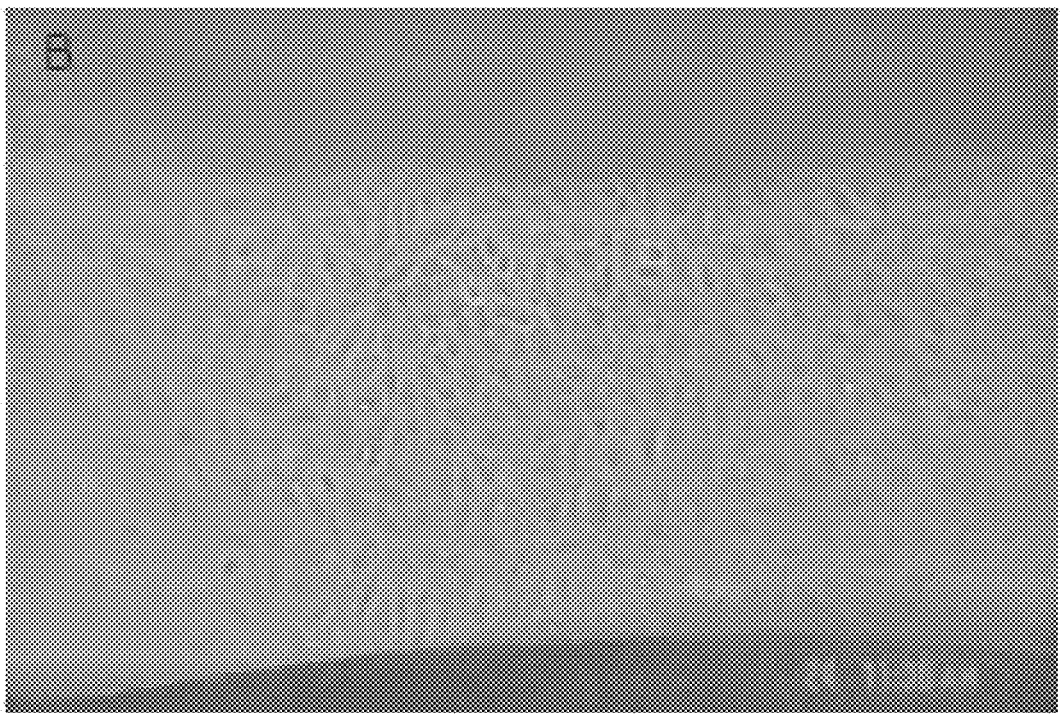
Figure 17A:
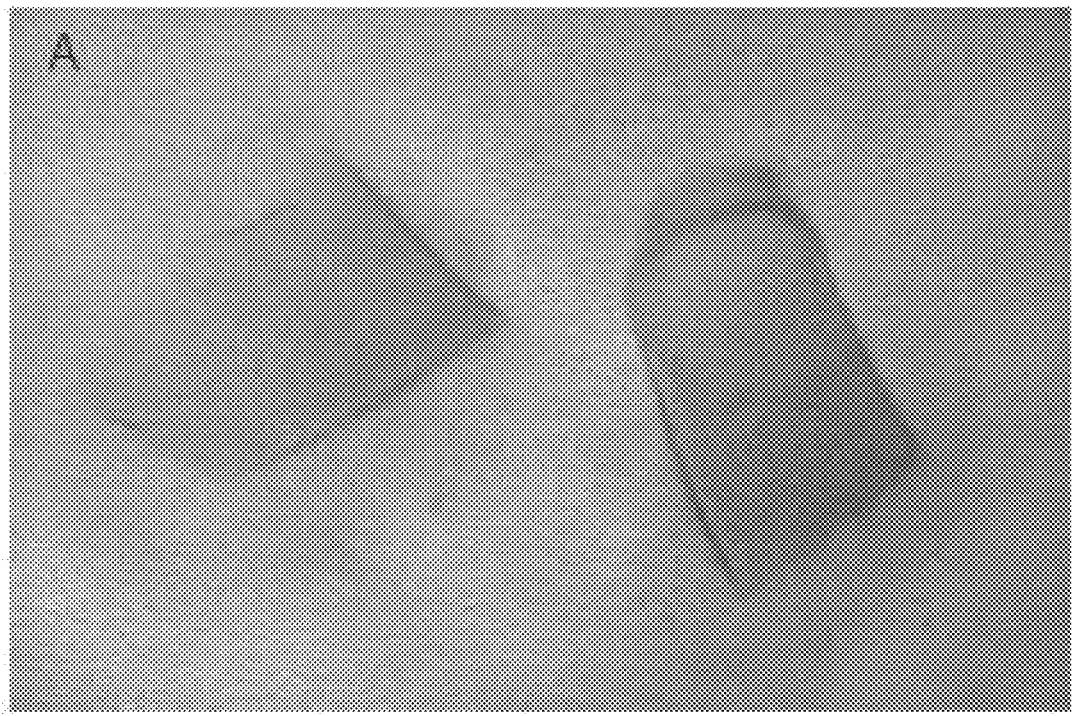
FIGS. 17A and 17B are a pair of photomicrographs of results after 10 weeks of culture, showing cells that migrated out of human juvenile cartilage explant proliferated and accumulated next to the original tissue pieces, where they piled up as multiple layers and reached approximately the same height of the cartilage pieces. A: 5×, B: 10×.
Figure 17B:
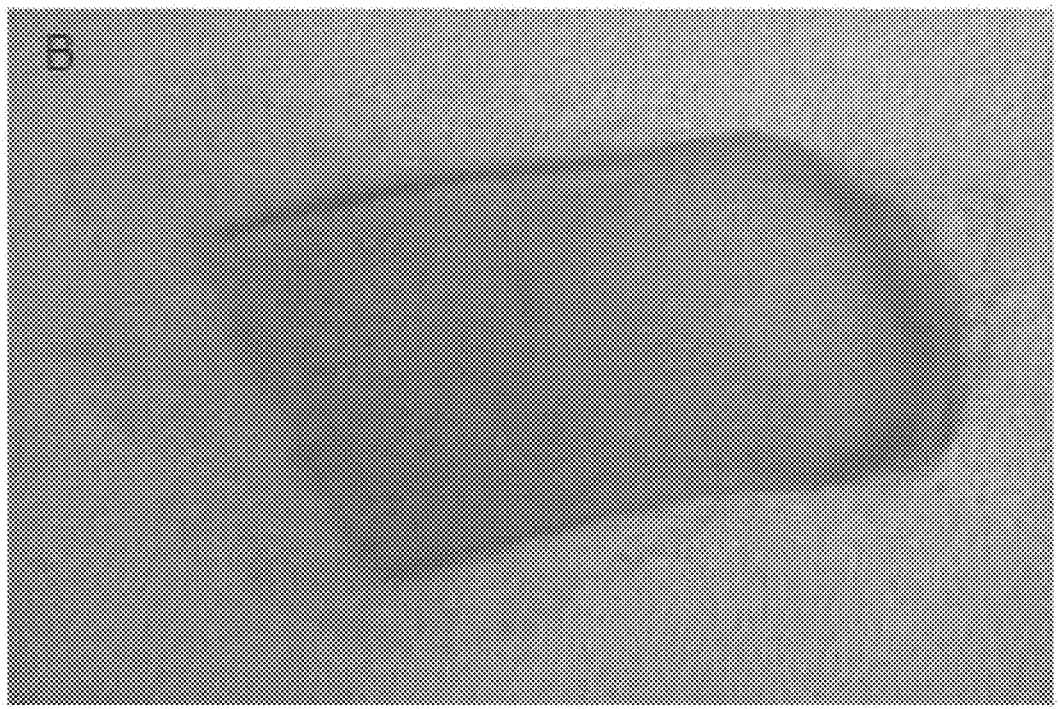

Initiation of Inter-Piece Interactions:

During cell migration, some cells migrated into the area between two cartilage pieces and produced extracellular matrix (ECM) simultaneously. The newly formed ECM along with the embedded cells generated the new inter-piece interactions which bind, adhere or "glue" these two pieces together (FIGS. 10 and 11). Over time, more and more cells migrated onto the bridge area between these two pieces. In addition, the cells that were already embedded inside the ECM continued to proliferated. As a result, the ECM became denser and the inter-piece interactions became thicker and wider, containing multiple layers of ECM and cells embedded therein (FIGS. 12, 13 and 14), and structurally integrated with the surrounding explanted tissue. The structure of the newly formed inter-piece interaction was found to be similar to the original cartilage tissue, based on the gross and histological observation (FIG. 15). In contrast, those cartilage explant pieces that were placed more than 1 mm apart were unable to integrate together. Instead, they were surrounded by the migrating and proliferating cells (FIG. 16). The cells accumulated next to the cartilage piece, where they piled up as multiple layers and reached almost the same height of the original piece at 10 weeks of culture (FIG. 17).

Example 2: Effect of Cartilage Harvesting Location and Implant Size

Figure 19:
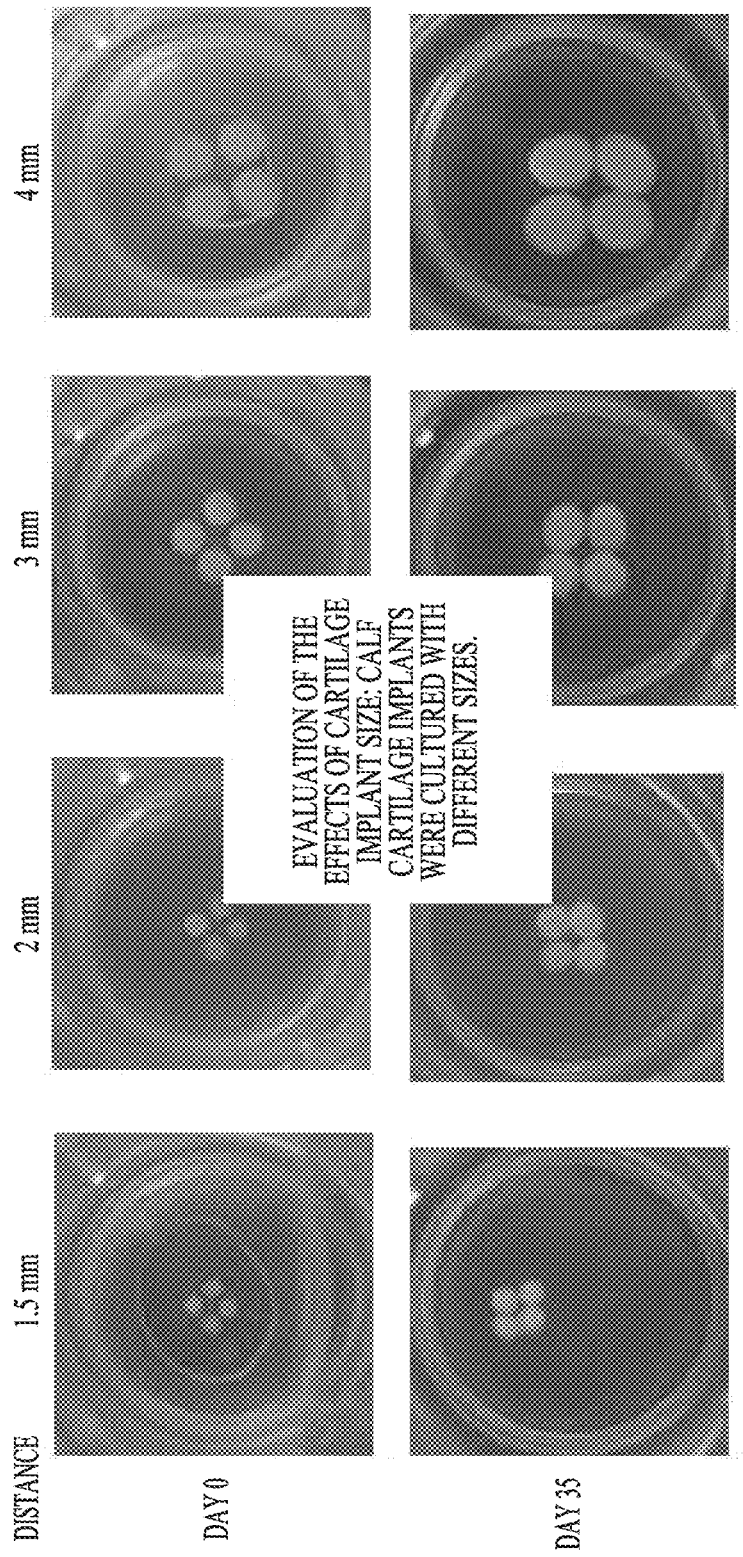
FIG. 19 is a photomicrograph showing results obtained with calf cartilage explants of different sizes.

Calf cartilage explants were harvested from five different locations of knee joint: trochlea, trochlea groove, femoral condyle, central tibial plateau and peripheral tibial plateau. The pieces of calf cartilage from different sources were placed according to methods in Example 1. No significant difference was observed on cell migration, cartilage explant expansion and integration among the calf cartilage explants harvested from different locations of knee joint (FIG. 18). Further evaluation was carried out with different sizes of calf cartilage explants. Calf cartilage explants of 1.5 mm, 2 mm, 3 mm and 4 mm in diameter were prepared and cultured according to methods as otherwise described in Example 1. No significant difference was observed on cell migration, cartilage explant expansion and integration among different sizes of calf cartilage explants (FIG. 19).

Figure 20:
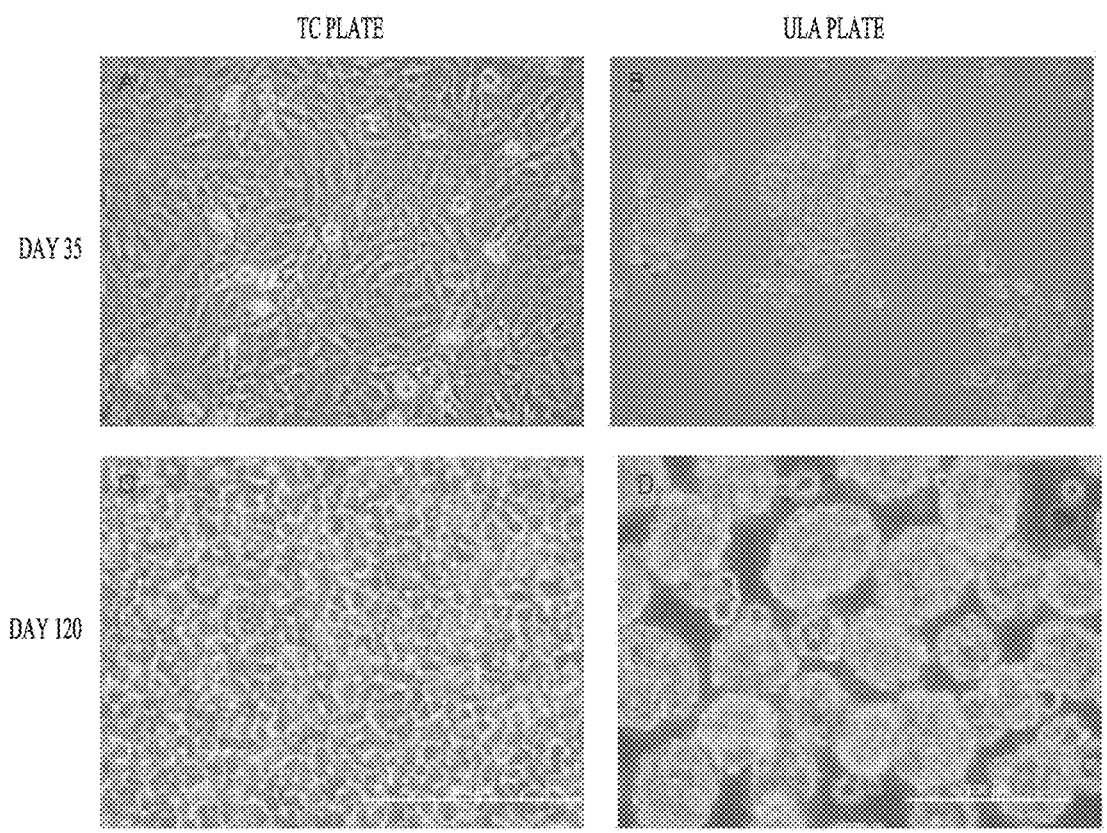
FIG. 20 is a series of photomicrographs showing migrated cells from calf cartilage explants having different phenotypes, on TC and ULA plates. A: the bottom layers of cell attached to the bottom area of TC plates on day 35 of culture (10×). B: The initial formation of cell cluster from individual cells on ULA plates on day 35 of culture (10×). C: Multiple layers of cells formed on the bottom of TC plates on day 120 of culture. The top layer of cells showed un-stretched round shape (10×). D: More and bigger cell clusters were formed on ULA plates on day 120 of culture, the majority of cells inside the cluster showed round shape (20×).

While there was no significant difference between ULA (ultra low attachment) and TC (regular tissue culture) plates on cell migration, cartilage explant growth and integration, significant differences were observed between these two plates on the phenotype of the migrated cells: on TC plates, the migrated cells proliferated and attached to the bottom areas of the plates. The over confluent cells formed multiple layers. The cells on the bottom layers became stretched showing fibroblast-like phenotype, whereas the cells on the top layer still maintained their original round shape showing the typical phenotype of chondrocytes. On ULA plates, instead of attaching to the bottom of the plates, the migrated cells attached to each other and formed cell clusters. Even though some cells on the bottom of the clusters became stretched and attached to the plates, the majority of the cells in the cluster still maintain their original round shapes (FIG. 20).

One skilled in the art would readily appreciate that the methods described in the present disclosure are well adapted to carry out the objects and obtain the ends and advantages mentioned, as well as those inherent therein. The methods, procedures, treatments, described herein are merely representative and exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. A method of making a cartilage tissue construct, the method comprising:
    placing a first surface of a first cartilage tissue piece and a first surface of a second cartilage tissue piece adjacent to an exposed surface of a solid or semi-solid support, wherein at least one of the first cartilage tissue piece and the second cartilage tissue piece comprises a cartilage explant;
    culturing, in vitro, the first cartilage tissue piece and the second cartilage tissue piece on the exposed surface of the support, including reorienting at least one of the first cartilage tissue piece and the second cartilage tissue piece, relative to the support, to direct the expansion or shape of the reoriented cartilage tissue piece.

2. The method of claim 1, wherein reorienting includes placing a second surface of the reoriented cartilage tissue piece adjacent to the exposed surface of the support.

3. The method of claim 1, wherein opposing surfaces of the reoriented cartilage tissue piece are directed to expand such that the reoriented cartilage tissue piece is substantially symmetrical on the opposing surfaces.

4. The method of claim 1, wherein the first cartilage tissue piece is spaced 1 mm or less from the second cartilage tissue piece, and wherein culturing is under conditions and for a period of time such that the first cartilage tissue piece and the second cartilage tissue piece expand and integrate to form a larger cartilage tissue piece.

5. The method of claim 4, wherein the first cartilage tissue piece and the second cartilage tissue piece become integrated in about 42 days or less.

* * * * *